US005646026A

United States Patent [19]

Walsh et al.

[11] Patent Number: 5,646,026

[45] Date of Patent: *Jul. 8, 1997

[54] RIBOSOME-INACTIVATING PROTEINS, INACTIVE PRECURSOR FORMS THEREOF, A PROCESS FOR MAKING AND A METHOD OF USING

[75] Inventors: Terence A. Walsh; Timothy D. Hey, both of Zionsville, Ind.; Alice E. R. Morgan, Midland, Mich.

[73] Assignee: DowElanco, Indianapolis, Ind.

[*] Notice: The term of this patent shall not extend beyond the expiration date of Pat. No. 5,248,606.

[21] Appl. No.: 485,286

[22] Filed: Jun. 7, 1995

Related U.S. Application Data

[62] Division of Ser. No. 378,761, Jan. 26, 1995, which is a continuation of Ser. No. 987,927, Dec. 9, 1992, abandoned, which is a continuation-in-part of Ser. No. 535,636, Jun. 11, 1990, Pat. No. 5,248,606.

[51] Int. Cl.$^6$ ............................... C12N 9/22; C12P 21/06
[52] U.S. Cl. ................ 435/199; 435/69.1; 435/252.3; 435/254.21; 435/320.1; 435/412; 435/325; 536/23.2; 536/23.6; 530/376
[58] Field of Search ............................... 435/69.1, 240.2, 435/240.4, 252.3, 254.21, 320.1; 536/23.6, 23.2; 530/376

*Primary Examiner*—Robert A. Wax
*Assistant Examiner*—Nashaat T. Nashed
*Attorney, Agent, or Firm*—Andrea T. Borucki

[57] ABSTRACT

The present invention is directed to a ribosome inactivating proteins. The proteins are characterized by being in a single chain proRIP inactive form that can be converted into an active form by cleavage with proteases.

9 Claims, 53 Drawing Sheets

FIG. 1A

| | | | | | | | | | | | | | | | | |
|---|---|---|---|---|---|---|---|---|---|---|---|---|---|---|---|---|
| 1<br>1 | GAA<br>  | TTC<br>  | GGC<br>  | ACG<br>  | AGC<br>  | AAA<br>  | GAG<br>  | AAG<br>  | GGA<br>  | ATG<br>Met | GCC<br>Ala | GAG<br>Glu | ATA<br>Ile | ACC<br>Thr | CTA<br>Leu | GAG<br>Glu | CCG<br>Pro |
| 52<br>9 | AGT<br>Ser | GAT<br>Asp | CTT<br>Leu | ATG<br>Met | GCG<br>Ala | CAA<br>Gln | ACA<br>Thr | AAC<br>Asn | AAA<br>Lys | AGA<br>Arg | ATA<br>Ile | GTG<br>Val | CCA<br>Pro | AAG<br>Lys | TTC<br>Phe | ACT<br>Thr | GAA<br>Glu |
| 103<br>26 | ATC<br>Ile | TTC<br>Phe | CCC<br>Pro | GTG<br>Val | GAG<br>Glu | GAC<br>Asp | GCG<br>Ala | AAC<br>Asn | TAC<br>Tyr | CCT<br>Pro | TAC<br>Tyr | AGC<br>Ser | GCC<br>Ala | TTC<br>Phe | ATC<br>Ile | GCG<br>Ala | TCG<br>Ser |
| 154<br>43 | GTC<br>Val | CGG<br>Arg | AAA<br>Lys | GAC<br>Asp | ATC<br>Ile | AAA<br>Lys | CAC<br>His | TGC<br>Cys | ACC<br>Thr | GAC<br>Asp | CAT<br>His | AAA<br>Lys | GGG<br>Gly | ATC<br>Ile | TTC<br>Phe | CAG<br>Gln |   |
| 205<br>60 | CCC<br>Pro | GTG<br>Val | CTG<br>Leu | CCA<br>Pro | CCG<br>Pro | GAG<br>Glu | AAG<br>Lys | GTC<br>Val | AAG<br>Lys | CCG<br>Pro | GAG<br>Glu | CTA<br>Leu | TGG<br>Trp | TTC<br>Phe | TAC<br>Tyr | ACA<br>Thr | GAG<br>Glu |
| 256<br>77 | CTC<br>Leu | AAA<br>Lys | ACT<br>Thr | AGG<br>Arg | ACC<br>Thr | AGC<br>Ser | TCC<br>Ser | ATC<br>Ile | ACG<br>Thr | CTC<br>Leu | GCC<br>Ala | ATA<br>Ile | CGC<br>Arg | ATG<br>Met | GAC<br>Asp | AAC<br>Asn | CTG<br>Leu |
| 307<br>94 | TAC<br>Tyr | CTC<br>Leu | GTG<br>Val | GGC<br>Gly | TTC<br>Phe | AGG<br>Arg | ACC<br>Thr | CCG<br>Pro | GGG<br>Gly | GTG<br>Val | TGG<br>Trp | TGG<br>Trp | GAG<br>Glu | TTC<br>Phe | GGC<br>Gly | AAG<br>Lys |   |

FIG. 1B

```
358  GAC GGC GAC ACC CAC CTC CTC GGC GAC AAC CCC AGG TGG CTC GGC TTC GGC
111  Asp Gly Asp Thr His Leu Leu Gly Asp Asn Pro Arg Trp Leu Gly Phe Gly

409  GGC AGG TAC CAG GAC CTC ATC GGC AAC AAG GGT CTG GAG ACC GTC ACC ATG
128  Gly Arg Tyr Gln Asp Leu Ile Gly Asn Lys Gly Leu Glu Thr Val Thr Met

460  GGC CGC GCC GAA ATG ACC AGG GCC GTC AAC GAC CTG GCG AAG CTG CCG AAG
145  Gly Arg Ala Glu Met Thr Arg Ala Val Asn Asp Leu Ala Lys Leu Pro Lys

511  ATG GCG ACA CTG GAG GAG GTG AAG ATG CAG ATG CAG ATG CCG GAG
162  Met Ala Thr Leu Glu Glu Val Lys Met Gln Met Gln Met Pro Glu

562  GCC GCT GAT CTG GCG GCA GCG GCT GAC CCA CAG CAG GCC GAC ACG AAG
179  Ala Ala Asp Leu Ala Ala Ala Ala Asp Pro Gln Gln Ala Asp Thr Lys

613  AGC AAG CTG GTG CTG GTC ATG GTG TGC GGG GAG GGG CTG CGG TTC AAC
196  Ser Lys Leu Val Leu Val Val Met Val Cys Gly Glu Gly Leu Arg Phe Asn

664  ACC GTG TCC CGC ACG GTG GAC GTG GCG GGG TTC AAC AGC CAG CAC GGG GTG ACC
213  Thr Val Ser Arg Thr Val Asp Val Ala Gly Phe Asn Ser Gln His Gly Val Thr
```

FIG. 1C

```
715  TTG ACC GTG ACG CAG GGG AAG CAG GTG CAG AAG TGG GAC AGG ATC TCC AAG
230  Leu Thr Val Thr Gln Gly Lys Gln Val Gln Lys Trp Asp Arg Ile Ser Lys

766  GCG GCC TTC GAG TGG GCT GAC CAC CCC ACC CCC ATC GTG ATC CCC GAC ATG CAG
247  Ala Ala Phe Glu Trp Ala Asp His Pro Thr Ala Val Ile Pro Asp Met Gln

817  AAG CTT GGC ATC AAG GAT AAG AAC GAA GCA GCG AGG ATC GTT GCG CTC GTT
264  Lys Leu Gly Ile Lys Asp Lys Asn Glu Ala Ala Arg Ile Val Ala Leu Val

868  AAG AAT CAA ACT ACT GCC GCT GCT ACT GCC AGT GCT GAC AAC GAC
281  Lys Asn Gln Thr Thr Ala Ala Ala Thr Ala Ser Ala Asp Asn Asp

919  GAC GAG GCC TGA TCA ATG CAA CGA CAC ATC ATG TGC TGC ACT
298  Asp Asp Glu Ala End

970  TAA TTA CTA TGT TCG TAT ACA AAT AAA TAC ACC CGG CGT ACG CGG TGT TCC

1021 TTA TAT GGT CTA AAA TGT AGC CAG TAA ATT TTA AAC TAC TTT CTC GTG CCG

1072 AAT TC
```

FIG. 3

```
Maize RIP    1  MAEITLEPSDLMAQTNKRIVPKFTEIFPVEDANYPYSAFIASVRKDVIKHCTDHKGIFQPV
                                : ::   ::  :  ::  :  ::  :::   :
Barley RIP   1  ------------AAKMAKNVDKPLFTATFNVQASSADYATFIAGIRNKLRNPA--HFSHNEPV 61  LPP-EKKVPEL-WFYTELKTR-TSS--ITLAIRMDNLYLVGFRTPGGVWWEFGKDGDTHLLG
                |||   :  :  ||:  |:   |:|   |||||:||:|  ||::|| ||| | |
            50  LPPVEPNVPPSRWFHVLKASPTSAGLTLAIRADNIYLEGFKSSDGTWWELTPGLIPGAT- 119  DNPRWLGFGGRYQDLIGNKGLET--VTMGRAEMTRAVNDLAKKKKMATLEEEVKMQMPE
                     :|||| | ||  :   |   :||| :: : |  |
           110  ----YVGFGGTYRDLLGDTDKLTNVALGRQQLEDAVTALHGRTK------

187  AADLAAAAAADPQADTKSKLVKLVVMVCEGLRFNTVSRTVDAGFNSQHGVTLT----VTQG
                  :|    : :  || ::: | ::: | :|| ||::|  |:   :
           150  ----ADKASGPKQQQAREAVTTLLLMVNEATRFQTVSGFVAGLLHPKAVEKKSGKIGNEMK

236  KQVQKWDRISKAAFEWADHPTAVIPDMQKLGIKDKNEAARIVALVKNQTTAAAATAASADN
                 || :||  :  |::|      ||  :   ::                :|||| ::
           207  AQVNGWQDLS-AALLK----TDVKPPPGKSPAKFTPIEKMGVRTAEQ----AAATLGILLF

297  DDDEA
                  :
           259  VEVPGGLTVAKALELFHASGGK
```

FIG. 4

```
Maize RIP      1    --------MAEITLEPSDLMAQTNKRIVPKFTEIFPVEDANYPYSAFIASVRKDVIKHCT
                       :  :        ||   ||                  ||   ||
Ricin A chain -24   MYAVATWLCFGSTSGWSFTLEDNNIFPKQYPIINFTTAGATVQSYTNFIRAVRGRLTTGAD 62    DHKGIFQPVLPP-EKKVPELWF--YTELKTR-TSSITLAIRMDNLYLYVGFRTPGGVWWEFGK
                    ||||                       |||||     :  :   |:|:|
              38    VR---HEIPVLPNRVGLPINQRFILVELSNHAELSVTLALDVTNAYVVVGYRAGNSAYFFHPD 110    DGDTHLLGDNPR------WLGFGGRYQDLIGNKGL--ETVTMGRAEMTRAVNDLAKKKKM
                      :                 |||                :  :
              97    NQEDAEAITHLFTDVQNRYTFAFGGNYDRLEQLAGNLRENIELGNGPLEEAISALYYYST- 164    ATLEEEVKMQMQMPEAADLAAAAADPQADTKSKLVKLVVMVCEGLRFNTVSRTVDAGFN
                                    :                       :  :  :
             157    --------------------GGTQLPTLARSFIICIQMISEAARFQYIEGEMRTRIR 224    SQHGVTLTVTQGKQVQKWDRISKAAFEWADHPTAVIPDMQKLGI-KDKNEAARIVALVKNQ
                      :  |:|:  :  :                   |:|               :  :
             194    YNRRSAPDPSVITLENSWGRLSTAIQESNQGAFASPIQLQRRNGSKFSVYDVSILIPIIAL 284    TTAAAATAAASADNDDDEA
                                 —
             255    MVYRCAPPPSQF
```

FIG. 5A

```
Maize RIP       AQTNKRIVPKFTEIF--PVEDANYPYSAFIASVRKDVIK
Barley RIP      AAKMAKNVDKPLFTATF--NVQASSADYATFIAGIRNKLRN
Ricin A         IFPKQYPIINFTTAGATVQSYTNFIRAVRGRLTT
Trichosanthin                     DVSFRLSGATSSSYGVFISNLRKALPN
Momordin                          DVSFRLSGADPRSYGMFIKDLRNALPF
Bryodin                           DVSFRLSGATTTSYGVFIKNLREALPY
Gelonin                           GLDTVSFSTKGATYITYVNFLNELRVKLKP
Dodecandrin                       VNTIIYNVGSTTISNYATFMDNLRNEAKD
Pokeweed AP2                      N-IVFDYENATPETYSNFLTSLREAVKD
Saporin 5                         VTSITLDLVNPTAGQYSSFVDKIRNNVKD
Saporin 4                         VIIYELNLQGTTKAQYSTILKQLRDDIKD
SLT-1A                            KEFTLDFSTAKTYDSLNV-IRSAIGT
```

FIG. 5B

| | | | | | | |
|---|---|---|---|---|---|---|
| Maize RIP | 84 | ITLAIRMDNLYLVGF | 201 | LVVMVCEGLRFNTVS | 237 | QVQK-WDRISKA |
| Barley RIP | 76 | LTLAIRADNIYLEGF | 168 | LLLMVNEATRFQTVS | 208 | QVNG-WQDLSAA |
| Ricin A-chain | 70 | VTLALDVTNAYVVGY | 171 | CIQMISEAARFQYIE | 207 | LENS-WGRLSTA |
| Saporin-6 | 62 | VSLGLKRDNLYVVAY | 170 | AIQMTAEAARFRYIQ | 205 | EVN--WKKISTA |
| Abrin A-chain | 64 | IEVGIDVTNAYVVAY | 159 | IIQVASEAARFRYIS | 194 | LENN-WDNLRGV |
| SLT-1A | 62 | MIDSGSGDNLFAVDV | 183 | FVTVTAEALRFQIQR | 222 | TLN--WGRLSSV |
| Trichosanthin | 58 | DEVALDVTNV. . . | 161 | LIQSTSEAARYKFIE | 196 | LENSLWLALSKQ |
| | 77 | YLMGY | | | | |

FIG. 7A

```
  1  GCTTAATTAA TTAAGCTTAA AAGGAGGAAA AAAATTATGG CCGAGATAAC CCTAGAGCCG
 61  AGTGATCTTA TGGCGCAAAC AAACAAAAGA ATAGTGCCAA AGTTCACTGA AATCTTCCCC
121  GTGGAGGACG CGAACTACCC TTACAGCGCC TTCATCGCGT CGGTCCGGAA AGACGTGATC
181  AAACACTGCA CCGACCATAA AGGGATCTTC CAGCCCGTGC TGCCACCGGA GAAGAAGGTC
241  CCGGAGCTAT GGTTCTACAC AGAGCTCAAA ACTAGGACCA GCTCCATCAC GCTCGCCATA
301  CGCATGGACA ACCTGTACCT CGTGGGCTTC AGGACCCCCG GCGGGGTGTG GTGGGAGTTC
361  GGCAAGGACG GCGACACCCA CCTCCTCGGC GACAACCCCA GGTGGCTCGG CTTCGGCGGC
421  AGGTACCAGG ACCTCATCGG CAACAAGGGT CTGGAGACCG TCACCATGGG CCGCGCCGAA
481  ATGACCAGGG CCGTCAACGA CCTGGGCGAA AAGAAGAAGA TGGCGACACT GGAGGAGGAG
541  GAGGTGAAGA TGCAGATGCA GATGCCGGAG GCCGCTGATC TGGCGGGCGC GGCAGCGGCT
601  GACCCACAGG CCGACACGAA GAGCAAGCTG GTGAAGCTGG TGGTCATGGT GTGCGAGGGG
661  CTGCGGTTCA ACACCGTGTC CCGCACGGTG GACGCGGGGT TCAACAGCCA GCACGGGGTG
```

FIG. 7B

```
721   ACCTTGACCG TGACGCAGGG GAAGCAGGTG CAGAAGTGGG ACAGGATCTC CAAGGCGGCC
781   TTCGAGTGGG CTGACCACCC CACCGCTGTG ATCCCCGACA TGCAGAAGCT TGGCATCAAG
841   GATAAGAACG AAGCAGGCGAG GATCGTTGCG CTCGTTAAGA ATCAAACTAC TGCCGCTGCC
901   GCTACTGCTG CCAGTGCTGA CAACGACGAC GACGAGGCCT GATCAATGCA ACGACACATC
961   ATGATCTGCT GCTGCACTTA ATTACTATGT TCGTATACAA ATAAATACAC CCGGGCGTACG
1021  CGGTGTTCCT TATATGGTCT AAAATGTAGC CAGTAAATTT TAAACTACTT TCTCGTGCCG
1081  AATTCACTGG CCGGCATGCT ATATA
```

FIG. 8A

```
                TCCCTCTAGATGCGGGCCTAATTAATTAAGCTTAAAAGGAGGAAAAAATT ATG AAA AGA
  1                                                               Met Lys Arg>

60             ATA GTG CCA AAG TTC ACT GAA ATC TTC CCC GTG GAG GAC GCG AAC TAC
  4             Ile Val Pro Lys Phe Thr Glu Ile Phe Pro Val Glu Asp Ala Asn Tyr>

108             CCT TAC AGC GCC TTC ATC GCG TCG GTC CGG AAA GAC GTG ATC AAA CAC
 20             Pro Tyr Ser Ala Phe Ile Ala Ser Val Arg Lys Asp Val Ile Lys His>

156             TGC ACC GAC CAT AAA GGG ATC TTC CAG CCC GTG CTG CCA CCG GAG AAG
 36             Cys Thr Asp His Lys Gly Ile Phe Gln Pro Val Leu Pro Pro Glu Lys>

204             AAG GTC CCG GAG CTA TGG TTC TAC ACA GAG CTC AAA ACT AGG ACC AGC
 52             Lys Val Pro Glu Leu Trp Phe Tyr Thr Glu Leu Lys Thr Arg Thr Ser>

252             TCC ATC ACG CTC GCC ATA CGC ATG GAC AAC CTG TAC CTC GTG GGC TTC
 68             Ser Ile Thr Leu Ala Ile Arg Met Asp Asn Leu Tyr Leu Val Gly Phe>

300             AGG ACC CCG GGC GGG GTG TGG TGG GAG TTC GGC AAG GAC GGC GAC ACC
 84             Arg Thr Pro Gly Gly Val Trp Trp Glu Phe Gly Lys Asp Gly Asp Thr>

348             CAC CTC CTC GGC GAC AAC CCC AGG TGG CTC GGC TTC GGC GGC AGG TAC
100             His Leu Leu Gly Asp Asn Pro Arg Trp Leu Gly Phe Gly Gly Arg Tyr>
```

FIG. 8B

```
396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg>

444  GCC GAA ATG ACC AGG GCC GTC AAC GAC CTG GCG AAG AAG ATG
132  Ala Glu Met Thr Arg Ala Val Asn Asp Leu Ala Lys Lys Met>

492  GCG ACA CTG GAG GAG GTG AAG ATG CAG ATG CCG GAG ACG
148  Ala Thr Leu Glu Glu Val Lys Met Gln Met Pro Glu Thr>

540  GCC GCT GAT CTG GCG GCA GCG GCT GAC CCA CAG GCC GAC ACG
164  Ala Ala Asp Leu Ala Ala Ala Ala Asp Pro Gln Ala Asp Thr>

588  AAG AGC AAG CTG GTG AAG CTG GTC ATG GTG TGC GAG GGG CTG CGG
180  Lys Ser Lys Leu Val Lys Leu Val Met Val Cys Glu Gly Leu Arg>

636  TTC AAC ACC GTG TCC CGC ACG GTG GAC GCG GGG TTC AAC AGC CAG CAC
196  Phe Asn Thr Val Ser Arg Thr Val Asp Ala Gly Phe Asn Ser Gln His>

684  GGG GTG ACC TTG ACC GTG ACG CAG GGG AAG CAG GTG CAG AAG TGG GAC
212  Gly Val Thr Leu Thr Val Thr Gln Gly Lys Gln Val Gln Lys Trp Asp>

732  AGG ATC TCC AAG GCG GCC TTC GAG TGG GCT GAC CAC CCC ACC GCT GTG
228  Arg Ile Ser Lys Ala Ala Phe Glu Trp Ala Asp His Pro Thr Ala Val>
```

FIG. 8C

```
780   ATC CCC GAC ATG CAG AAG CTT GGC ATC AAG GAT AAG AAC GAA GCA GCG
244   Ile Pro Asp Met Gln Lys Leu Gly Ile Lys Asp Lys Asn Glu Ala Ala>

828   AGG ATC GTT GCG CTC GTT AAG AAT CAA ACT ACT GCC GCT GCT ACT
260   Arg Ile Val Ala Leu Val Lys Asn Gln Thr Thr Ala Ala Ala Thr>

876   GCT GCC AGT GCT GAC AAC GAC GAC GAG GCC TGA TCAATGCAACGACAC
276   Ala Ala Ser Ala Asp Asn Asp Asp Glu Ala END

927   ATCATGATCTGCTGCTGCACTTAATTACTATGTTCGTATACAAATAAATACACCCGGCGTACG

990   CGGTGTTCCTTATATGGTCTAAAATGTAGCCAGTAAATTTAAACTACTTTCTCGTGCCGAAT

1053  TCACTGGCCCGGGCATGCTATATA
```

FIG. 10A

```
1     GCTAATTAATTAAGCTTAAAGGAGGAAAAATT ATG GCC GAG ATA ACC CTA GAG
1                                      Met Ala Glu Ile Thr Leu Glu>

57    CCG AGT GAT CTT ATG GCG CAA ACA AAC AAA AGA ATA GTG CCA AAG TTC
8     Pro Ser Asp Leu Met Ala Gln Thr Asn Lys Arg Ile Val Pro Lys Phe>

105   ACT GAA ATC TTC CCC GTG GAG GAC GCG AAC TAC CCT TAC AGC GCC TTC
24    Thr Glu Ile Phe Pro Val Glu Asp Ala Asn Tyr Pro Tyr Ser Ala Phe>

153   ATC GCG TCG GTC CGG AAA GAC GTG ATC AAA CAC TGC ACC GAC CAT AAA
40    Ile Ala Ser Val Arg Lys Asp Val Ile Lys His Cys Thr Asp His Lys>

201   GGG ATC TTC CAG CCC GTG CTG CCA CCG GAG AAG GTC CCG GAG CTA
56    Gly Ile Phe Gln Pro Val Leu Pro Pro Glu Lys Lys Val Pro Glu Leu>

249   TGG TTC TAC ACA GAG CTC AAA ACT AGG ACC AGC TCC ATC ACG CTC GCC
72    Trp Phe Tyr Thr Glu Leu Lys Thr Arg Thr Ser Ser Ile Thr Leu Ala>

297   ATA CGC ATG GAC AAC CTG TAC CTC GTG GGC TTC AGG ACC CCG GGC GGG
88    Ile Arg Met Asp Asn Leu Tyr Leu Val Gly Phe Arg Thr Pro Gly Gly>

345   GTG TGG TGG GAG TTC GGC AAG GAC GGC GAC ACC CAC CTC CTC GGC GAC
104   Val Trp Trp Glu Phe Gly Lys Asp Gly Asp Thr His Leu Leu Gly Asp>
```

FIG. 10B

```
393  AAC CCC AGG TGG CTC GGC TTC GGC AGG TAC CAG GAC CTC ATC GGC
120  Asn Pro Arg Trp Leu Gly Phe Gly Arg Tyr Gln Asp Leu Ile Gly>

441  AAC AAG GGT CTG GAG ACC ATG GGC CGC GCC GAA ATG ACC AGG
136  Asn Lys Gly Leu Glu Thr Met Gly Arg Ala Glu Met Thr Arg>

489  GCC GTC AAC GAC CTG GCG AAG AAG CTG GCT GAC CCA CAG GCC
152  Ala Val Asn Asp Leu Ala Lys Lys Leu Ala Asp Pro Gln Ala>

537  GAC ACG AAG AGC AAG CTG GTG AAG CTG GTC ATG GTG TGC GAG GGG
168  Asp Thr Lys Ser Lys Leu Val Lys Leu Val Met Val Cys Glu Gly>

585  CTG CGG TTC AAC ACC GTG TCC CGC ACG GTG GAC GCG GGG TTC AAC AGC
184  Leu Arg Phe Asn Thr Val Ser Arg Thr Val Asp Ala Gly Phe Asn Ser>

633  CAG CAC GGG GTG ACC ACG GTG ACG CAG GGG AAG CAG GTG CAG AAG
200  Gln His Gly Val Thr Val Thr Val Gln Gly Lys Gln Val Gln Lys>

681  TGG GAC AGG ATC TCC AAG GCG GCC TTC GAG TGG GCT GAC CAC CCC ACC
216  Trp Asp Arg Ile Ser Lys Ala Ala Phe Glu Trp Ala Asp His Pro Thr>

729  GCT GTG ATC CCC GAC ATG CAG AAG CTT GGC ATC AAG GAT AAG AAC GAA
232  Ala Val Ile Pro Asp Met Gln Lys Leu Gly Ile Lys Asp Lys Asn Glu>
```

FIG. 10C

```
777  GCA GCG AGG ATC GTT GCG CTC GTT AAG AAT CAA ACT ACT GCC GCT GCC
248  Ala Ala Arg Ile Val Ala Leu Val Lys Asn Gln Thr Thr Ala Ala Ala>

825  GCT ACT GCT GCC AGT GCT GAC AAC GAC GAC GAG GCC TGA TCAATGC
264  Ala Thr Ala Ala Ser Ala Asp Asn Asp Asp Glu Ala END

874  AACGACACATCATGATCTGCTGCTGCACTTAATTACTATGTTCGTATACAAATAAATACACCC
937  GGCGTACGCGGTGTTCCTTATATGGTCTAAAATGTAGCCAGTAAATTTAAACTACTTTCTCG
1000 TGCCGAATTCACTGGGCCCGGCATGCTATATA
```

FIG. 11A

```
1         GCTTAATTAATTAAGCTTAAAAGGAGGAAAAAATT ATG AAA AGA ATA GTG CCA
1                                             Met Lys Arg Ile Val Pro>

55        AAG TTC ACT GAA ATC TTC CCC GTG GAG GAC GCG AAC TAC CCT TAC AGC
7         Lys Phe Thr Glu Ile Phe Pro Val Glu Asp Ala Asn Tyr Pro Tyr Ser>

103       GCC TTC ATC GCG TCG GTC CGG AAA GAC GTG ATC AAA CAC TGC ACC GAC
23        Ala Phe Ile Ala Ser Val Arg Lys Asp Val Ile Lys His Cys Thr Asp>

151       CAT AAA GGG ATC TTC CAG CCC CTG CCA CCG GAG AAG GTC CCG
39        His Lys Gly Ile Phe Gln Pro Leu Pro Pro Glu Lys Lys Val Pro>

199       GAG CTA TGG TTC TAC ACA GAG CTC AAA ACT AGG ACC AGC ATC ACG
55        Glu Leu Trp Phe Tyr Thr Glu Leu Lys Thr Arg Thr Ser Ile Thr>

247       CTC GCC ATA CGC ATG GAC AAC CTG TAC CTC GTG GGC TTC AGG ACC CCG
71        Leu Ala Ile Arg Met Asp Asn Leu Tyr Leu Val Gly Phe Arg Thr Pro>

295       GGC GGG GTG TGG TGG GAG TTC GGC AAG GAC GGC GAC ACC CAC CTC CTC
87        Gly Gly Val Trp Trp Glu Phe Gly Lys Asp Gly Asp Thr His Leu Leu>

343       GGC GAC AAC CCC AGG TGG CTC GGC TTC GGC AGG TAC CAG GAC CTC
103       Gly Asp Asn Pro Arg Trp Leu Gly Phe Gly Gly Arg Tyr Gln Asp Leu>
```

FIG. 11B

```
391  ATC GGC AAC AAG GGT CTG GAG ACC GTC ACC ATG GGC CGC GCC GAA ATG
119  Ile Gly Asn Lys Gly Leu Glu Thr Val Thr Met Gly Arg Ala Glu Met>

439  ACC AGG GCC GTC AAC GAC CTG GCG AAG AAG AAG GCG GCT GAC CCA
135  Thr Arg Ala Val Asn Asp Leu Ala Lys Lys Lys Ala Ala Asp Pro>

487  CAG GCC GAC ACG AAG AGC AAG CTG GTG AAG CTG GTC ATG GTG TGC
151  Gln Ala Asp Thr Lys Ser Lys Leu Val Lys Leu Val Met Val Cys>

535  GAG GGG CTG CGG TTC AAC ACC GTG TCC CGC ACG GCG GGG TTC
167  Glu Gly Leu Arg Phe Asn Thr Val Ser Arg Thr Val Asp Ala Gly Phe>

583  AAC AGC CAG CAC GGG GTG GAC AGG ATC TCC AAG GCG GTG ACG CAG GTG
183  Asn Ser Gln His Gly Val Asp Arg Ile Ser Lys Ala Val Thr Gln Val>

631  CAG AAG TGG GAC AGG ATC TCC AAG GCG GCC TTC GAG TGG GCT GAC CAC
199  Gln Lys Trp Asp Arg Ile Ser Lys Ala Ala Phe Glu Trp Ala Asp His>

679  CCC ACC GCT GTG ATC CCC GAC ATG CAG AAG CTT GGC ATC AAG GAT AAG
215  Pro Thr Ala Val Ile Pro Asp Met Gln Lys Leu Gly Ile Lys Asp Lys>

727  AAC GAA GCA GCG AGG ATC GTT GCG CTC GTT AAG AAT CAA ACT ACT GCC
231  Asn Glu Ala Ala Arg Ile Val Ala Leu Val Lys Asn Gln Thr Thr Ala>
```

FIG. 11C

```
775  GCT GCC GCT ACT GCT GCC AGT GCT GAC AAC GAC GAC GAG GCC TGA
247  Ala Ala Ala Thr Ala Ala Ser Ala Asp Asn Asp Asp Glu Ala END

823  TCAATGCAACGACACATCATGATCTGCTGCTGCACTTAATTACTATGTTCGTATACAAATAAA

886  TACACCCGGGTACGCGGGTGTTCCTTATATGGTCTAAAAATGTAGCCAGTAAATTTTAAACTAC

949  TTTCTCGTGCCCGAATTCACTGGCCCGGGCATGCTATATA
```

FIG. 12A

```
1    TCCCTCTAGATGCGGCCTAATTAAGCTTAAAAGGAGGAAAAAATT ATG
1                                                  Met

54   AAA AGA ATA GTG CCA AAG TTC ACT GAA ATC TTC CCC GTG GAG GAC GCG AAC
1    Lys Arg Ile Val Pro Lys Phe Thr Glu Ile Phe Pro Val Glu Asp Ala Asn

105  TAC CCT TAC AGC GCC TTC ATC GCG TCG GTC CGG AAA GAC GTG ATC AAA CAC
19   Tyr Pro Tyr Ser Ala Phe Ile Ala Ser Val Arg Lys Asp Val Ile Lys His

156  TGC ACC GAC CAT AAA GGG ATC TTC CAG CCC GTG CTG CCA CCG GAG AAG AAG
36   Cys Thr Asp His Lys Gly Ile Phe Gln Pro Val Leu Pro Pro Glu Lys Lys

207  GTC CCG GAG CTA TGG TTC TAC ACA GAG CTC AAA ACT AGG ACC AGC TCC ATC
53   Val Pro Glu Leu Trp Phe Tyr Thr Glu Leu Lys Thr Arg Thr Ser Ser Ile

258  ACG CTC GCC ATA CGC ATG GAC AAC CTG TAC CTC GTG GGC TTC AGG ACC CCG
70   Thr Leu Ala Ile Arg Met Asp Asn Leu Tyr Leu Val Gly Phe Arg Thr Pro

309  GGC GGG GTG TGG GAG TTC TGG GAG AAG GAC ACC CAC CTC CTC GGC
87   Gly Gly Val Trp Trp Glu Gly Lys Phe Asp Gly Asp Thr His Leu Leu Gly

360  GAC AAC CCC AGG TGG CTC GGC TTC GGC AGG TAC CAG GAC CTC ATC GGC
104  Asp Asn Pro Arg Trp Leu Gly Phe Gly Gly Arg Tyr Gln Asp Leu Ile Gly
```

FIG. 12B

| | | | | | | | | | | | | | | | | |
|---|---|---|---|---|---|---|---|---|---|---|---|---|---|---|---|---|
| 411 | AAC | AAG | GGT | CTG | GAG | ACC | GTC | ACC | ATG | GGC | CGC | GCC | GAA | ATG | ACC | AGG | GCC |
| 121 | Asn | Lys | Gly | Leu | Glu | Thr | Val | Thr | Met | Gly | Arg | Ala | Glu | Met | Thr | Arg | Ala |
| 462 | GTC | AAC | GAC | CTG | GCG | AAG | AAG | AAG | CTG | GCG | GCT | GCC | CCA | CAG | GCC | GAC | ACG |
| 138 | Val | Asn | Asp | Leu | Ala | Lys | Lys | Lys | Leu | Ala | Ala | Ala | Pro | Gln | Ala | Asp | Thr |
| 513 | AAG | AGC | AAG | CTG | GTG | AAG | CTG | GTG | ATG | GTG | TGC | GAG | GGG | CTG | CGG | TTC |
| 155 | Lys | Ser | Lys | Leu | Val | Lys | Leu | Val | Met | Val | Cys | Glu | Gly | Leu | Arg | Phe |
| 564 | AAC | ACC | GTG | TCC | CGC | ACG | GTG | GAC | GCG | GGG | TTC | AAC | AGC | CAG | CAC | GGG | GTG |
| 172 | Asn | Thr | Val | Ser | Arg | Thr | Val | Asp | Ala | Gly | Phe | Asn | Ser | Gln | His | Gly | Val |
| 615 | ACC | TTG | ACC | GTG | ACG | CAG | AAG | CAG | GTG | CCC | ACC | AAG | TGG | GAC | AGG | ATC | TCC |
| 189 | Thr | Leu | Thr | Val | Thr | Gln | Gly | Lys | Gln | Val | Pro | Thr | Trp | Asp | Arg | Ile | Ser |
| 666 | AAG | GCG | GCC | TTC | GAG | TGG | GCT | GAC | CAC | CCC | ACC | GCT | GTG | ATC | CCC | GAC | ATG |
| 206 | Lys | Ala | Ala | Phe | Glu | Trp | Ala | Asp | His | Pro | Thr | Ala | Val | Ile | Pro | Asp | Met |
| 717 | CAG | AAG | CTT | GGC | ATC | AAG | GAT | AAG | AAC | GAA | GCA | GCG | AGG | ATC | GTT | GCG | CTC |
| 223 | Gln | Lys | Leu | Gly | Ile | Lys | Asp | Lys | Asn | Glu | Ala | Ala | Arg | Ile | Val | Ala | Leu |
| 768 | GTT | AAG | AAT | CAA | ACT | ACT | GCC | GCT | GCC | GCT | ACT | GCT | GGA | TCC | GCC | TGA | TCA |
| 240 | Val | Lys | Asn | Gln | Thr | Thr | Ala | Ala | Ala | Ala | Thr | Ala | Gly | Ser | Ala | End | |

FIG. 12C

819 ATGCAACGACACATCATGATCTGCTGCTGCACTTAATTACTATGTTCGTATACAAATAAATACACCC

886 GGCGTACGCGGTGTTCCTTATATGGTCTAAAAATGTAGCCAGTAAATTTAAACTACTTTCTCGTGCC

953 GAATTCACTGGGCCCGGGCATGCTATATA

FIG. 13A

```
  1    TCCCTCTAGATGCGGGCCTAATTAATTAAGCTTAAAAGGAGGAAAAAAATT ATG AAA
  1                                                       Met Lys>

57    AGA ATA GTG CCA AAG TTC ACT GAA ATC TTC CCC GTG GAG GAC GCG
  3    Arg Ile Val Pro Lys Phe Thr Glu Ile Phe Pro Val Glu Asp Ala>

102    AAC TAC CCT TAC AGC GCC TTC ATC GCG TCG GTC CGG AAA GAC GTG
 18    Asn Tyr Pro Tyr Ser Ala Phe Ile Ala Ser Val Arg Lys Asp Val>

147    ATC AAA CAC TGC ACC GAC CAT AAA GGG ATC TTC CAG CCC GTG CTG
 33    Ile Lys His Cys Thr Asp His Lys Gly Ile Phe Gln Pro Val Leu>

192    CCA CCG GAG AAG AAG GTC CCG GAG CTA TGG TTC TAC ACA GAG CTC
 48    Pro Pro Glu Lys Lys Val Pro Glu Leu Trp Phe Tyr Thr Glu Leu>

237    AAA ACT AGG ACC AGC TCC ATC ACG CTC GCC ATA CGC ATG GAC AAC
 63    Lys Thr Arg Thr Ser Ser Ile Thr Leu Ala Ile Arg Met Asp Asn>

282    CTG TAC CTC GTG GGC TTC AGG ACC CCG GGC GGG GTG TGG TGG GAG
 78    Leu Tyr Leu Val Gly Phe Arg Thr Pro Gly Gly Val Trp Trp Glu>

327    TTC GGC AAG GAC GGC AAG GAC ACC CAC CTC CTC GGC GAC AAC CCC AGG
 93    Phe Gly Lys Asp Gly Lys Asp Thr His Leu Leu Gly Asp Asn Pro Arg>
```

FIG. 13B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC CGC GCC GAA ATG ACC AGG GCC
123  Gly Leu Glu Thr Val Thr Met Gly Arg Ala Glu Met Thr Arg Ala>
                                              Not1        Pst1
                                              ——          ——
462  GTC AAC GAC CTG GCG AAG AAG AAG GCG GCC GCC GCT GCA GAC
138  Val Asn Asp Leu Ala Lys Lys Lys Ala Ala Ala Ala Ala Asp>

507  CCA CAG GCC GAC ACG AAG AGC AAG CTG GTG AAG CTG GTC ATG
153  Pro Gln Ala Asp Thr Lys Ser Lys Leu Val Lys Leu Val Met>

552  GTG TGC GAG GGG CTG CGG TTC AAC ACC GTG TCC CGC ACG GTG GAC
168  Val Cys Glu Gly Leu Arg Phe Asn Thr Val Ser Arg Thr Val Asp>

597  GCG GGG TTC AAC AGC CAG CAC GGG GTG ACC TTG ACC GTG ACG CAG
183  Ala Gly Phe Asn Ser Gln His Gly Val Thr Leu Thr Val Thr Gln>

642  GGG AAG CAG GTG CAG AAG TGG GAC AGG ATC TCC AAG GCC GCC TTC
198  Gly Lys Gln Val Gln Lys Trp Asp Arg Ile Ser Lys Ala Ala Phe>
```

FIG. 13C

```
687  GAG TGG GCT GAC CAC CCC ACC GCT GTG ATC CCC GAC ATG CAG AAG
213  Glu Trp Ala Asp His Pro Thr Ala Val Ile Pro Asp Met Gln Lys>

732  CTT GGC ATC AAG GAT AAG AAC GAA GCA GCG AGG ATC GTT GCG CTC
228  Leu Gly Ile Lys Asp Lys Asn Glu Ala Ala Arg Ile Val Ala Leu>

777  GTT AAG AAT CAA ACT ACT GCC GCT GCC GCT ACT GCT GGA TCC GCC
243  Val Lys Asn Gln Thr Thr Ala Ala Ala Ala Thr Ala Gly Ser Ala>

822  TGATCAATGCAACGACACACATCATGATCTGCTGCACTTAATTACTATGTTCGTATACA
     End<

882  AATAAATACACCCGGGCGTACGCGGGTGTTCCTTATATGGTCTAAAATGTAGCCAGTAAATT

942  TTAAACTACTTTCTCGTGCCGAATTCACTGGCCGGGCATGCTATATA
```

FIG. 14A

```
      TCCCTCTAGATGCGGCCTAATTAATTAAGCTTAAAGGAGGAAAAAATT ATG AAA
                                                       Met Lys>

57   AGA ATA GTG CCA AAG TTC ACT GAA ATC TTC CCC GTG GAG GAC GCG
  3   Arg Ile Val Pro Lys Phe Thr Glu Ile Phe Pro Val Glu Asp Ala>

102   AAC TAC CCT TAC AGC GCC TTC ATC GCG TCG GTC CGG AAA GAC GTG
 18   Asn Tyr Pro Tyr Ser Ala Phe Ile Ala Ser Val Arg Lys Asp Val>

147   ATC AAA CAC TGC ACC GAC CAT AAA GGG ATC TTC CAG CCC GTG CTG
 33   Ile Lys His Cys Thr Asp His Lys Gly Ile Phe Gln Pro Val Leu>

192   CCA CCG GAG AAG AAG GTC CCG GAG CTA TGG TTC TAC ACA GAG CTC
 48   Pro Pro Glu Lys Lys Val Pro Glu Leu Trp Phe Tyr Thr Glu Leu>

237   AAA ACT AGG ACC AGC TCC ATC ACG CTC GCC ATA CGC ATG GAC AAC
 63   Lys Thr Arg Thr Ser Ser Ile Thr Leu Ala Ile Arg Met Asp Asn>

282   CTG TAC CTC GTG GGC TTC AGG ACC CCG GGC GTG TGG GAG
 78   Leu Tyr Leu Val Gly Phe Arg Thr Pro Gly Val Trp Glu>
```

FIG. 14B

```
327  TTC GGC AAG GAC GGC GAC ACC CAC CTC CTC GGC GAC AAC CCC AGG
 93  Phe Gly Lys Asp Gly Asp Thr His Leu Leu Gly Asp Asn Pro Arg>

372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC CGC GCC GAA ATG ACC AGG GCC
123  Gly Leu Glu Thr Val Thr Met Gly Arg Ala Glu Met Thr Arg Ala>

462  GTC AAC GAC CTG GCG AAG AAG AAG GCG GCT GAC CCA CAG GCC
138  Val Asn Asp Leu Ala Lys Lys Lys Ala Ala Asp Pro Gln Ala>

507  GAC ACG AAG AGC AAG CTG GTG AAG CTG GTC ATG GTG TGC GAG
153  Asp Thr Lys Ser Lys Leu Val Lys Leu Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>
```

FIG. 14C

```
642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>

732  AAG GAT AAG AAC GAA GCA GCG AGG ATC GTT GCG CTC GTT AAG AAT
228  Lys Asp Lys Asn Glu Ala Ala Arg Ile Val Ala Leu Val Lys Asn>

777  CAA ACT ACT GCC GCT GCC GCT ACT GCT GGA TCC GCT GAT AAC AAT
243  Gln Thr Thr Ala Ala Ala Ala Thr Ala Gly Ser Ala Asp Asn Asn>

822  TTC AAC AAA GAA CAA CAA AAT GCT TTC TAT GAA ATC TTG AAT ATG
258  Phe Asn Lys Glu Gln Gln Asn Ala Phe Tyr Glu Ile Leu Asn Met>

867  CCT AAC TTA AAC GAA GAA CAA CGC AAT GGT TTC ATC CAA AGC TTA
273  Pro Asn Leu Asn Glu Glu Gln Arg Asn Gly Phe Ile Gln Ser Leu>

912  AAA GAT GAC CCA AGT CAA AGT GCT AAC CTA TTG TCA GAA GCT AAA
288  Lys Asp Asp Pro Ser Gln Ser Ala Asn Leu Leu Ser Glu Ala Lys>
```

FIG. 14D

```
957   AAG TTA AAT GAA TCT CAA GCA CCG AAA GAT CGA TCC GCC TGATCAA
303   Lys Leu Asn Glu Ser Gln Ala Pro Lys Asp Arg Ser Ala End<

1003  TGCAACGACACACATCATGATCATCTGCTCTGCACTTAATTACTATGTTCGTATACAAATAAA
1062  TACACCCGGGCGTACGCGGGTGTTCCTTATATGGTCTAAAATGTAGCCAGTAAATTTTAAA
1121  CTACTTTCTCGTGCCGAATTCACTGGCCCGGGCATGCTATATA
```

FIG. 15A

```
                  TCCCTCTAGATGCGGGCCTAATTAATTAAGCTTAAAAGGAGGAAAAAATT ATG AAA
                                                                    Met Lys>

57  AGA ATA GTG CCA AAG TTC ACT GAA ATC TTC CCC GTG GAG GAC GCG
  3  Arg Ile Val Pro Lys Phe Thr Glu Ile Phe Pro Val Glu Asp Ala>

102  AAC TAC CCT TAC AGC GCC TTC ATC GCG TCG GTC CGG AAA GAC GTG
 18  Asn Tyr Pro Tyr Ser Ala Phe Ile Ala Ser Val Arg Lys Asp Val>

147  ATC AAA CAC TGC ACC GAC CAT AAA GGG ATC TTC CAG CCC GTG CTG
 33  Ile Lys His Cys Thr Asp His Lys Gly Ile Phe Gln Pro Val Leu>

192  CCA CCG GAG AAG AAG GTC CCG GAG CTA TGG TTC TAC ACA GAG CTC
 48  Pro Pro Glu Lys Lys Val Pro Glu Leu Trp Phe Tyr Thr Glu Leu>

237  AAA ACT AGG ACC AGC TCC ATC ACG CTC GCC ATA CGC ATG GAC AAC
 63  Lys Thr Arg Thr Ser Ser Ile Thr Leu Ala Ile Arg Met Asp Asn>

282  CTG TAC CTC GTG GGC TTC AGG ACC CCG GGC GGG GTG TGG TGG GAG
 78  Leu Tyr Leu Val Gly Phe Arg Thr Pro Gly Gly Val Trp Trp Glu>

327  TTC GGC AAG GAC GGC GAC ACC CAC CTC CTC GGC GAC AAC CCC AGG
 93  Phe Gly Lys Asp Gly Asp Thr His Leu Leu Gly Asp Asn Pro Arg>
```

FIG. 15B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC GCC GAA ATG ACC AGG GCC
123  Gly Leu Glu Thr Val Thr Met Gly Ala Glu Met Thr Arg Ala>

462  GTC AAC GAC CTG GCG AAG AAG AAG GCG GCT GAC CCA CAG GCC
138  Val Asn Asp Leu Ala Lys Lys Lys Ala Ala Asp Pro Gln Ala>

507  GAC ACG AAG AGC AAG CTG GTG AAG CTG GTG ATG GTG TGC GAG
153  Asp Thr Lys Ser Lys Leu Val Lys Leu Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>

642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>
```

FIG. 15C

| | | | | | | | | | | | | | | |
|---|---|---|---|---|---|---|---|---|---|---|---|---|---|---|
|732|AAG|GAT|AAG|AAC|GAA|GCA|GCG|AGG|ATC|GTT|GCG|CTC|GTT|AAG|AAT|
|228|Lys|Asp|Lys|Asn|Glu|Ala|Ala|Arg|Ile|Val|Ala|Leu|Val|Lys|Asn>|
|777|CAA|ACT|ACT|GCC|GCT|GCC|GCT|ACT|GCT|GGA|TCC|AAA|CCA|GAA|GTG|
|243|Gln|Thr|Thr|Ala|Ala|Ala|Ala|Thr|Ala|Gly|Ser|Lys|Pro|Glu|Val>|
|822|ATC|GAT|GCG|TCT|GAA|TTA|ACA|CCA|GCC|GTG|ACA|ACT|TAC|AAA|CTT|
|258|Ile|Asp|Ala|Ser|Glu|Leu|Thr|Pro|Ala|Val|Thr|Thr|Tyr|Lys|Leu>|
|867|GTT|ATT|AAT|GGT|AAA|ACA|TTG|AAA|GGC|GAA|ACA|ACT|ACT|GAA|GCT|
|273|Val|Ile|Asn|Gly|Lys|Thr|Leu|Lys|Gly|Glu|Thr|Thr|Thr|Glu|Ala>|
|912|GTT|GAT|GCT|GCT|ACT|GCA|GAA|AAA|GTC|TTC|AAA|CAA|TAC|GCT|AAC|
|288|Val|Asp|Ala|Ala|Thr|Ala|Glu|Lys|Val|Phe|Lys|Gln|Tyr|Ala|Asn>|
|957|GAC|AAC|GGT|GTT|GAC|GGT|GAA|TGG|ACT|TAC|GAC|GAT|GCG|ACT|AAG|
|303|Asp|Asn|Gly|Val|Asp|Gly|Glu|Trp|Thr|Tyr|Asp|Asp|Ala|Thr|Lys>|
|1002|ACC|TTT|ACA|GTT|ACT|GAA|AAA|CCA|GAA|GTG|ATC|GAT|GCG|TCT|GAA|
|318|Thr|Phe|Thr|Val|Thr|Glu|Lys|Pro|Glu|Val|Ile|Asp|Ala|Ser|Glu>|
|1047|TTA|ACA|CCA|GCC|GTG|ACA|AGA|TCC|GCT|GAT|AAC|AAT|TTC|AAC|AAA|
|333|Leu|Thr|Pro|Ala|Val|Thr|Arg|Ser|Ala|Asp|Asn|Asn|Phe|Asn|Lys>|

FIG. 15D

```
1092  GAA CAA CAA AAT GCT TTC TAT GAA ATC TTG AAT ATG CCT AAC TTA
348   Glu Gln Gln Asn Ala Phe Tyr Glu Ile Leu Asn Met Pro Asn Leu>

1137  AAC GAA GAA CAA CGC AAT GGT TTC ATC CAA AGC TTA AAA GAT GAC
363   Asn Glu Glu Gln Arg Asn Gly Phe Ile Gln Ser Leu Lys Asp Asp>

1182  CCA AGC CAA AGT GCT AAC CTA TTG TCA GAA GCT AAA AAG TTA AAT
378   Pro Ser Gln Ser Ala Asn Leu Leu Ser Glu Ala Lys Lys Leu Asn>

1227  GAA TCT CAA GCA CCG AAA GAT CGA TCC GCC TGATCAATGCAACGACACA
393   Glu Ser Gln Ala Pro Lys Asp Arg Ser Ala End<

1276  TCATGATCTGCTGCACTTAATTACTATGTTCGTATACAAATAAATACACCCGGGCGT

1335  ACGCGGGTGTTCCTTATATGGTCTAAAATGTAGCCAGTAAATTTTAAACTACTTTCTCGT

1394  GCCGAATTCACTGGCCCGGCATGCTATATA
```

FIG. 16A

```
                    TCCCTCTAGATGCGGGCCTAATTAATTAAGCTTAAAGGAGGAAAAAATT ATG AAA
  1                                                                  Met Lys>
  1

57   AGA ATA GTG CCA AAG TTC ACT GAA ATC TTC CCC GTG GAG GAC GCG
  3   Arg Ile Val Pro Lys Phe Thr Glu Ile Phe Pro Val Glu Asp Ala>

102   AAC TAC CCT TAC AGC GCC TTC ATC GCG TCG GTC CGG AAA GAC GTG
 18   Asn Tyr Pro Tyr Ser Ala Phe Ile Ala Ser Val Arg Lys Asp Val>

147   ATC AAA CAC TGC ACC GAC CAT AAA GGG ATC TTC CAG CCC GTG CTG
 33   Ile Lys His Cys Thr Asp His Lys Gly Ile Phe Gln Pro Val Leu>

192   CCA CCG GAG AAG AAG GTC CCG GAG CTA TGG TTC TAC ACA GAG CTC
 48   Pro Pro Glu Lys Lys Val Pro Glu Leu Trp Phe Tyr Thr Glu Leu>

237   AAA ACT AGG ACC AGC TCC ATC ACG CTC GCC ATA CGC ATG GAC AAC
 63   Lys Thr Arg Thr Ser Ser Ile Thr Leu Ala Ile Arg Met Asp Asn>

282   CTG TAC CTC GTG GGC TTC AGG ACC CCG GGC GGG GTG TGG TGG GAG
 78   Leu Tyr Leu Val Gly Phe Arg Thr Pro Gly Gly Val Trp Trp Glu>

327   TTC GGC AAG GAC GGC GAC ACC CAC CTC CTC GGC GAC AAC CCC AGG
 93   Phe Gly Lys Asp Gly Asp Thr His Leu Leu Gly Asp Asn Pro Arg>
```

FIG. 16B

```
372  TGG CTC GGC TTC GGC AGG TAC CAG GAC CTC ATC GGC AAC AAG
108  Trp Leu Gly Phe Gly Arg Tyr Gln Asp Leu Ile Gly Asn Lys>

417  GGT CTG GAG ACC GTC ACC ATG GGC CGC GAA ATG GCC ACC AGG GCC
123  Gly Leu Glu Thr Val Thr Met Gly Arg Glu Met Ala Thr Arg Ala>

462  GTC AAC GAC CTG GCG AAG AAG AAG GCG GCT GAC CCA CAG GCC
138  Val Asn Asp Leu Ala Lys Lys Lys Ala Ala Asp Pro Gln Ala>

507  GAC ACG AAG AGC AAG CTG GTG AAG CTG GTC ATG GTG TGC GAG
153  Asp Thr Lys Ser Lys Leu Val Lys Leu Val Met Val Cys Glu>

552  GGG CTG CGG TTC AAC ACC GTG TCC CGC ACG GTG GAC GCG GGG TTC
168  Gly Leu Arg Phe Asn Thr Val Ser Arg Thr Val Asp Ala Gly Phe>

597  AAC AGC CAG CAC GGG GTG ACC TTG ACC GTG ACG CAG GGG AAG CAG
183  Asn Ser Gln His Gly Val Thr Leu Thr Val Thr Gln Gly Lys Gln>

642  GTG CAG AAG TGG GAC AGG ATC TCC AAG GCG GCC TTC GAG TGG GCT
198  Val Gln Lys Trp Asp Arg Ile Ser Lys Ala Ala Phe Glu Trp Ala>

687  GAC CAC CCC ACC GCT GTG ATC CCC GAC ATG CAG AAG CTT GGC ATC
213  Asp His Pro Thr Ala Val Ile Pro Asp Met Gln Lys Leu Gly Ile>
```

FIG. 16C

```
732  AAG GAT AAG AAC GAA GCA GCG AGG ATC GTT GCG CTC GTT AAG AAT
228  Lys Asp Lys Asn Glu Ala Ala Arg Ile Val Ala Leu Val Lys Asn>

777  CAA ACT ACT GCC GCT GCC GCT ACT GCT GGA TCC AAA CCA GAA GTG
243  Gln Thr Thr Ala Ala Ala Ala Thr Ala Gly Ser Lys Pro Glu Val>

822  ATC GAT GCG TCT GAA TTA ACA CCA GCC GTG ACA ACT TAC AAA CTT
258  Ile Asp Ala Ser Glu Leu Thr Pro Ala Val Thr Thr Tyr Lys Leu>

867  GTT ATT AAT GGT AAA ACA TTG AAA GGC GAA ACA ACT ACT GAA GCT
273  Val Ile Asn Gly Lys Thr Leu Lys Gly Glu Thr Thr Thr Glu Ala>

912  GTT GAT GCT GCT ACT GCA GAA AAA GTC TTC AAA CAA TAC GCT AAC
288  Val Asp Ala Ala Thr Ala Glu Lys Val Phe Lys Gln Tyr Ala Asn>

957  GAC AAC GGT GTT GAC GGT GAA TGG ACT TAC GAT GCG ACT AAG
303  Asp Asn Gly Val Asp Gly Glu Trp Thr Tyr Asp Ala Thr Lys>

1002 ACC TTT ACA GTT ACT GAA AAA CCA GAA GTG ATC GAT GCG TCT GAA
318  Thr Phe Thr Val Thr Glu Lys Pro Glu Val Ile Asp Ala Ser Glu>

1047 TTA ACA CCA GCC GTG ACA AGA TCC AAA CCA GAA GTG ATC GAT GCG
333  Leu Thr Pro Ala Val Thr Arg Ser Lys Pro Glu Val Ile Asp Ala>
```

FIG. 16D

```
1092  TCT GAA TTA ACA CCA GCC GTG ACA ACT TAC AAA CTT GTT ATT AAT
 348  Ser Glu Leu Thr Pro Ala Val Thr Thr Tyr Lys Leu Val Ile Asn>

1137  GGT AAA ACA TTG AAA GGC GAA ACA ACT ACT GAA GCT GTT GAT GCT
 363  Gly Lys Thr Leu Lys Gly Glu Thr Thr Thr Glu Ala Val Asp Ala>

1182  GCT ACT GCA GAA AAA GTC TTC AAA CAA TAC GCT AAC GAC AAC GGT
 378  Ala Thr Ala Glu Lys Val Phe Lys Gln Tyr Ala Asn Asp Asn Gly>

1227  GTT GAC GGT GAA TGG ACT TAC GAT GCG ACT AAG ACC TTT ACA
 393  Val Asp Gly Glu Trp Thr Tyr Asp Ala Thr Lys Thr Phe Thr>

1272  GTT ACT GAA AAA CCA GAA GTG ATC GAT GCG TCT GAA TTA ACA CCA
 408  Val Thr Glu Lys Pro Glu Val Ile Asp Ala Ser Glu Leu Thr Pro>

1317  GCC GTG ACA AGA TCC GCT GAT AAC AAT TTC AAC AAA GAA CAA CAA
 423  Ala Val Thr Arg Ser Ala Asp Asn Asn Phe Asn Lys Glu Gln Gln>

1362  AAT GCT TTC TAT GAA ATC TTG AAT ATG CCT AAC TTA AAC GAA GAA
 438  Asn Ala Phe Tyr Glu Ile Leu Asn Met Pro Asn Leu Asn Glu Glu>

1407  CAA CGC AAT GGT TTC ATC CAA AGC TTA AAA GAT GAC CCA AGC CAA
 453  Gln Arg Asn Gly Phe Ile Gln Ser Leu Lys Asp Asp Pro Ser Gln>
```

FIG. 16E

```
1452  AGT GCT AAC CTA TTG TCA GAA GCT AAA AAG TTA AAT GAA TCT CAA
468   Ser Ala Asn Leu Leu Ser Glu Ala Lys Lys Leu Asn Glu Ser Gln>

1497  GCA CCG AAA GAT CGA TCC GCC TGATCAATGCAACGACACATCATGATCTGCT
483   Ala Pro Lys Asp Arg Ser Ala End<

1549  GCTGCACTTAATTACTATGTTCGTATACAAATAAATACACCCGGCGTACGCGGGTGTTCC

1608  TTATATGGTCTAAAAATGTAGCCAGTAAATTTAAACTACTTTCTCGTGCCGAATTCACT

1667  GGCCGGCATGCTATATA
```

FIG. 17A

```
  1      TCCCTCTAGATGCGGGCCTAATTAATTAAGCTTAAAAGGAGGAAAAAAATT ATG AAA AGA
  1                                                         Met Lys Arg

60      ATA GTG CCA AAG TTC ACT GAA ATC TTC CCC GTG GAG GAC GCG AAC TAC
  4      Ile Val Pro Lys Phe Thr Glu Ile Phe Pro Val Glu Asp Ala Asn Tyr

108      CCT TAC AGC GCC TTC ATC GCG TCG GTC CGG AAA GAC GTG ATC AAA CAC
 20      Pro Tyr Ser Ala Phe Ile Ala Ser Val Arg Lys Asp Val Ile Lys His

156      TGC ACC GAC CAT AAA GGG ATC TTC CAG CCC GTG CTG CCA CCG GAG AAG
 36      Cys Thr Asp His Lys Gly Ile Phe Gln Pro Val Leu Pro Pro Glu Lys

204      AAG GTC CCG GAG CTA TGG TTC TAC ACA GAG CTC AAA ACT AGG ACC AGC
 52      Lys Val Pro Glu Leu Trp Phe Tyr Thr Glu Leu Lys Thr Arg Thr Ser

252      TCC ATC ACG CTC GCC ATA CGC ATG GAC AAC CTG TAC CTC GTG GGC TTC
 68      Ser Ile Thr Leu Ala Ile Arg Met Asp Asn Leu Tyr Leu Val Gly Phe

300      AGG ACC CCG GGC GGG GTG TGG GAG TTC GGC AAG GAC GGC GAC ACC
 84      Arg Thr Pro Gly Gly Val Trp Glu Phe Gly Lys Asp Gly Asp Thr
```

FIG. 17B

```
348  CAC CTC CTC GGC GAC AAC CCC AGG TGG CTC GGC TTC GGC AGG TAC
100  His Leu Leu Gly Asp Asn Pro Arg Trp Leu Gly Phe Gly Arg Tyr

396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg

444  GCC GAA ATG ACC AGG GCC GTC AAC GAC CTG GCG AAG AAG AAG GCG
132  Ala Glu Met Thr Arg Ala Val Asn Asp Leu Ala Lys Lys Lys Ala

492  GCT GAC CCA CAG GCC GAC ACG AAG AGC AAG CTG GTG AAG CTG GTG GTC
148  Ala Asp Pro Gln Ala Asp Thr Lys Ser Lys Leu Val Lys Leu Val Val

540  ATG GTG TGC GAG GGG TTC AAC ACC GTG TCC CGC ACG GTG GAC
164  Met Val Cys Glu Gly Phe Asn Thr Val Ser Arg Thr Val Asp

588  GCG GGG TTC AAC AGC CAG CAC GGG GTG ACC TTG ACC GTG ACG CAG GGG
180  Ala Gly Phe Asn Ser Gln His Gly Val Thr Leu Thr Val Thr Gln Gly

636  AAG CAG GTG CAG AAG TGG GAC AGG ATC TCC AAG GCG GCC TTC GAG TGG
196  Lys Gln Val Gln Lys Trp Asp Arg Ile Ser Lys Ala Ala Phe Glu Trp
```

FIG. 17C

```
684  GCT GAC CAC CCC ACC GCT GTG ATC CCC GAC ATG CAG AAG CTT GGC ATC
212  Ala Asp His Pro Thr Ala Val Ile Pro Asp Met Gln Lys Leu Gly Ile

732  AAG GAT AAG AAC GAA GCA GCG AGG ATC GTT GCG CTC GTT AAG AAT CAA
228  Lys Asp Lys Asn Glu Ala Ala Arg Ile Val Ala Leu Val Lys Asn Gln

Bam HI   Hpa I   Sal I   Eco RI
780  ACT ACT GCC GCT GCC GCT GGA TCC GTT AAC GTC GAC GAA TTC
244  Thr Thr Ala Ala Ala Ala Gly Ser Val Asn Val Asp Glu Phe

828  ACT GGC CGG CAT GCT ATA TA
260  Thr Gly Arg His Ala Ile Xxx
```

FIG. 18A

```
                        TCCCTCTAGATGCGGCCTAATTAATTAAGCTTAAAAGGAGGAAAAAATT ATG AAA AGA
1                                                                         Met Lys Arg

60   ATA GTG CCA AAG TTC ACT GAA ATC TTC CCC GTG GAG GAC GCG AAC TAC
1    Ile Val Pro Lys Phe Thr Glu Ile Phe Pro Val Glu Asp Ala Asn Tyr

108  CCT TAC AGC GCC TTC ATC GCG TCG CGG AAA GAC GTG ATC AAA CAC
4    Pro Tyr Ser Ala Phe Ile Ala Ser Val Arg Lys Asp Val Ile Lys His

156  TGC ACC GAC CAT AAA GGG ATC TTC CAG CCC GTG CTG CCA CCG GAG AAG
20   Cys Thr Asp His Lys Gly Ile Phe Gln Pro Val Leu Pro Pro Glu Lys

204  AAG GTC CCG GAG CTA TGG TTC TAC ACA GAG CTC AAA ACT AGG ACC AGC
36   Lys Val Pro Glu Leu Trp Phe Tyr Thr Glu Leu Lys Thr Arg Thr Ser

252  TCC ATC ACG CTC GCC ATA CGC ATG GAC AAC CTG TAC CTC GGC TTC
52   Ser Ile Thr Leu Ala Ile Arg Met Asp Asn Leu Tyr Leu Val Gly Phe

300  AGG ACC CCG GGC GGG GTG TGG GAG TTC GGC AAG GAC GGC GAC ACC
68   Arg Thr Pro Gly Gly Val Trp Trp Glu Phe Gly Lys Asp Gly Asp Thr

```
348  CAC CTC CTC GGC GAC AAC CCC AGG TGG CTC GGC TTC GGC AGG TAC
100  His Leu Leu Gly Asp Asn Pro Arg Trp Leu Gly Phe Gly Arg Tyr

396  CAG GAC CTC ATC GGC AAC AAG GGT CTG GAG ACC GTC ACC ATG GGC CGC
116  Gln Asp Leu Ile Gly Asn Lys Gly Leu Glu Thr Val Thr Met Gly Arg

444  GCC GAA ATG ACC AGG GCC GTC AAC GAC CTG GCG AAG AAG AAG GCG
132  Ala Glu Met Thr Arg Ala Val Asn Asp Leu Ala Lys Lys Lys Ala

492  GCT GAC CCA CAG GCC GAC ACG AAG AGC AAG CTG GTG AAG CTG GTC
148  Ala Asp Pro Gln Ala Asp Thr Lys Ser Lys Leu Val Lys Leu Val Val

540  ATG GTG TGC GAG GGG CTG CGG TTC AAC ACC GTG TCC CGC ACG GTG GAC
164  Met Val Cys Glu Gly Leu Arg Phe Asn Thr Val Ser Arg Thr Val Asp

588  GCG GGG TTC AAC AGC CAG CAC GGG GTG ACC TTG ACC GTG ACG CAG GGG
180  Ala Gly Phe Asn Ser Gln His Gly Val Thr Leu Thr Val Thr Gln Gly

636  AAG CAG GTG CAG AAG TGG GAC AGG ATC TCC AAG GCC TTC GAG TGG
196  Lys Gln Val Gln Lys Trp Asp Arg Ile Ser Lys Ala Phe Glu Trp
```

FIG. 18C

```
684  GCT GAC CAC CCC ACC GCT GTG ATC CCC GAC ATG CAG AAG CTT GGC ATC
212  Ala Asp His Pro Thr Ala Val Ile Pro Asp Met Gln Lys Leu Gly Ile

732  AAG GAT AAG AAC GAA GCA GCG AGG ATC GTT GCG CTC GTT AAG AAT CAA
228  Lys Asp Lys Asn Glu Ala Ala Arg Ile Val Ala Leu Val Lys Asn Gln
                                          Bam HI  Hpa I   Sal I
780  ACT ACT GCC GCT GCC ACT GCT GGA TCC GTT AAC GTC GAC AAA CCA
244  Thr Thr Ala Ala Ala Thr Ala Gly Ser Val Asn Val Asp Lys Pro

828  GAA GTG ATC GAT GCG TCT GAA TTA ACA CCA GCC GTG ACA ACT TAC AAA
260  Glu Val Ile Asp Ala Ser Glu Leu Thr Pro Ala Val Thr Thr Tyr Lys

876  CTT GTT ATT AAT GGT AAA ACA TTG AAA GGC GAA ACA ACT ACT GAA GCT
276  Leu Val Ile Asn Gly Lys Thr Leu Lys Gly Glu Thr Thr Thr Glu Ala

924  GTT GAT GCT GCT ACT GCA GAA AAA GTC TTC AAA CAA TAC GCT AAC GAC
292  Val Asp Ala Ala Thr Ala Glu Lys Val Phe Lys Gln Tyr Ala Asn Asp

972  AAC GGT GTT GAC GGT GAA TGG ACT TAC GAC GAT GCG ACT AAG ACC TTT
308  Asn Gly Val Asp Gly Glu Trp Thr Tyr Asp Asp Ala Thr Lys Thr Phe
```

FIG. 18D

```
1020  ACA GTT ACT GAA AAA CCA GAA GTG ATC GAT GCG TCT GAA TTA ACA CCA
 324  Thr Val Thr Glu Lys Pro Glu Val Ile Asp Ala Ser Glu Leu Thr Pro

1068  GCC GTG ACA AGA TCC AAA CCA GAA GTG ATC GAT GCG TCT GAA TTA ACA
 340  Ala Val Thr Arg Ser Lys Pro Glu Val Ile Asp Ala Ser Glu Leu Thr

1116  CCA GCC GTG ACA ACT TAC AAA CTT GTT ATT AAT GGT AAA ACA TTG AAA
 356  Pro Ala Val Thr Thr Tyr Lys Leu Val Ile Asn Gly Lys Thr Leu Lys

1164  GGC GAA ACA ACT ACT GAA GCT GTT GAT GCT GCA GAA AAA GTC
 372  Gly Glu Thr Thr Thr Glu Ala Val Asp Ala Ala Thr Ala Glu Lys Val

1212  TTC AAA CAA TAC GCT AAC GAC AAC GGT GTT GAC GGT GAA TGG ACT TAC
 388  Phe Lys Gln Tyr Ala Asn Asp Asn Gly Val Asp Gly Glu Trp Thr Tyr

1260  GAC GAT GCG ACT AAG ACC TTT ACA GTT ACT GAA AAA CCA GAA GTG ATC
 404  Asp Asp Ala Thr Lys Thr Phe Thr Val Thr Glu Lys Pro Glu Val Ile

1308  GAT GCG TCT GAA TTA ACA CCA GCC GTG ACA AGA TCC GCT GAT AAC AAT
 420  Asp Ala Ser Glu Leu Thr Pro Ala Val Thr Arg Ser Ala Asp Asn Asn

1356  TTC AAC AAA GAA CAA CAA AAT GCT TTC TAT GAA ATC TTG AAT ATG CCT
 436  Phe Asn Lys Glu Gln Gln Asn Ala Phe Tyr Glu Ile Leu Asn Met Pro
```

FIG. 18E

```
1404 AAC TTA AAC GAA GAA CAA CGC AAT GGT TTC ATC CAA AGC TTA AAA GAT
 452 Asn Leu Asn Glu Glu Gln Arg Asn Gly Phe Ile Gln Ser Leu Lys Asp

1452 GAC CCA AGC CAA AGT GCT AAC CTA TTG TCA GAA GCT AAA AAG TTA AAT
 468 Asp Pro Ser Gln Ser Ala Asn Leu Leu Ser Glu Ala Lys Lys Leu Asn

1500 GAA TCT CAA GCA CCG AAA GAT CGA TCC GCC TGA TCAATGCAACGACACATCA
 484 Glu Ser Gln Ala Pro Lys Asp Arg Ser Ala End

1552 TGATCTGCTGCTGCACTTAATTACTATGTTCGTATACAAATAAATACACCCGGGTACGCGGT

1615 GTTCCTTATATGGTCTAAAATGTAGCCAGTAAATTTTAAACTACTTTCTCGTGCCGAATTCAC

1678 TGGCCGGGCATGCTATATA
```

FIG. 19A

```
1     TCCCTCTAGATGCGGGCCTAATTAATTAAGCTTAAAAGGAGGAAAAAATT ATG AAA AGA
1                                                      Met Lys Arg

60    ATA GTG CCA AAG TTC ACT GAA ATC TTC CCC GTG GAG GAC GCG AAC TAC
4     Ile Val Pro Lys Phe Thr Glu Ile Phe Pro Val Glu Asp Ala Asn Tyr

108   CCT TAC AGC GCC TTC ATC GCG TCG GTC CGG AAA GAC GTG ATC AAA CAC
20    Pro Tyr Ser Ala Phe Ile Ala Ser Val Arg Lys Asp Val Ile Lys His

156   TGC ACC GAC CAT AAA GGG ATC TTC CAG CCC GTG CTG CCA CCG GAG AAG
36    Cys Thr Asp His Lys Gly Ile Phe Gln Pro Val Leu Pro Pro Glu Lys

204   AAG GTC CCG GAG CTA TGG TTC TAC ACA GAG CTC AAA ACT AGG ACC AGC
52    Lys Val Pro Glu Leu Trp Phe Tyr Thr Glu Leu Lys Thr Arg Thr Ser

252   TCC ATC ACG CTC GCC ATA CGC ATG GAC AAC CTG TAC CTC GTG GGC TTC
68    Ser Ile Thr Leu Ala Ile Arg Met Asp Asn Leu Tyr Leu Val Gly Phe

300   AGG ACC CCG GGC GTG TGG GAG TTC GGC GTG AAG GAC GGC GAC ACC
84    Arg Thr Pro Gly Val Trp Glu Phe Gly Val Lys Asp Gly Asp Thr

348   CAC CTC CTC GGC GAC AAC CCC AGG TGG CTC GGC TTC GGC AGG TAC
100   His Leu Leu Gly Asp Asn Pro Arg Trp Leu Gly Phe Gly Arg Tyr
```

FIG. 19B

```
396   CAG GAC CTC ATC GGC AAC AAG GGT CTG GAG ACC ATG GGC CGC
116   Gln Asp Leu Ile Gly Asn Lys Gly Leu Glu Thr Met Gly Arg

444   GCC GAA ATG ACC AGG GCC GTC AAC GAC CTG GCG AAG AAG GCG
132   Ala Glu Met Thr Arg Ala Val Asn Asp Leu Ala Lys Lys Ala

492   GCT GAC CCA CAG GCC GAC ACG AAG AGC AAG CTG GTG AAG CTG GTC
148   Ala Asp Pro Gln Ala Asp Thr Lys Ser Lys Leu Val Lys Leu Val

540   ATG GTG TGC GAG GGG CTG CGG TTC AAC ACC GTG TCC CGC ACG GTG GAC
164   Met Val Cys Glu Gly Leu Arg Phe Asn Thr Val Ser Arg Thr Val Asp

588   GCG GGG TTC AAC AGC CAG CAC GGG GTG ACC TTG ACC GTG ACG CAG GGG
180   Ala Gly Phe Asn Ser Gln His Gly Val Thr Leu Thr Val Thr Gln Gly

636   AAG CAG GTG CAG AAG TGG GAC AGG ATC TCC AAG GCC TTC GAG TGG
196   Lys Gln Val Gln Lys Trp Asp Arg Ile Ser Lys Ala Phe Glu Trp

684   GCT GAC CAC CCC ACC GCT GTG ATC CCC GAC ATG CAG AAG CTT GGC ATC
212   Ala Asp His Pro Thr Ala Val Ile Pro Asp Met Gln Lys Leu Gly Ile

732   AAG GAT AAG AAC GAA GCA GCG AGG ATC GTT GCG CTC GTT AAG AAT CAA
228   Lys Asp Lys Asn Glu Ala Ala Arg Ile Val Ala Leu Val Lys Asn Gln
```

FIG. 19C

```
                                                                        Bam HI
                                                                          |
780   ACT ACT GCC GCT GCC GCT ACT GCT GGA TCC TCT TGC GCT CGT GTC CGT
244   Thr Thr Ala Ala Ala Ala Thr Ala Gly Ser Ser Cys Ala Arg Val Arg

Sal I
                         |
828   CGT TCG AGC TGC GGT GTC GAC AAA CCA GAA GTG ATC GAT GCG TCT GAA
260   Arg Ser Ser Cys Gly Val Asp Lys Pro Glu Val Ile Asp Ala Ser Glu

876   TTA ACA CCA GCC GTG ACA ACT TAC AAA CTT GTT ATT AAT GGT AAA ACA
276   Leu Thr Pro Ala Val Thr Thr Tyr Lys Leu Val Ile Asn Gly Lys Thr

924   TTG AAA GGC GAA ACA GAA ACT ACT GAA GTT GAT GCT GCT ACT GCA GAA
292   Leu Lys Gly Glu Thr Glu Thr Thr Glu Val Asp Ala Ala Thr Ala Glu

972   AAA GTC TTC AAA CAA TAC GCT AAC GAC GGT GTT GAC GGT GAA TGG
308   Lys Val Phe Lys Gln Tyr Ala Asn Asp Gly Val Asp Gly Glu Trp

1020  ACT TAC GAC GAT GCG ACT AAG ACC TTT ACA GTT ACT GAA AAA CCA GAA
324   Thr Tyr Asp Asp Ala Thr Lys Thr Phe Thr Val Thr Glu Lys Pro Glu

1068  GTG ATC GAT GCG TCT GAA TTA ACA CCA GCC GTG ACA AGA TCC AAA CCA
340   Val Ile Asp Ala Ser Glu Leu Thr Pro Ala Val Thr Arg Ser Lys Pro
```

FIG. 19D

```
1116  GAA GTG ATC GAT GCG TCT GAA TTA ACA CCA GCC GTG ACA ACT TAC AAA
356   Glu Val Ile Asp Ala Ser Glu Leu Thr Pro Ala Val Thr Thr Tyr Lys

1164  CTT GTT ATT AAT GGT AAA ACA TTG AAA GGC GAA ACA ACT ACT GAA GCT
372   Leu Val Ile Asn Gly Lys Thr Leu Lys Gly Glu Thr Thr Thr Glu Ala

1212  GTT GAT GCT GCT ACT GCA GAA AAA GTC TTC AAA CAA TAC GCT AAC GAC
388   Val Asp Ala Ala Thr Ala Glu Lys Val Phe Lys Gln Tyr Ala Asn Asp

1260  AAC GGT GTT GAC GGT GAA TGG ACT TAC GAC GAT GCG ACT AAG ACC TTT
404   Asn Gly Val Asp Gly Glu Trp Thr Tyr Asp Asp Ala Thr Lys Thr Phe

1308  ACA GTT ACT GAA AAA CCA GAA GTG ATC GAT GCG TCT GAA TTA ACA CCA
420   Thr Val Thr Glu Lys Pro Glu Val Ile Asp Ala Ser Glu Leu Thr Pro

1356  GCC GTG ACA AGA TCC GCT GAT AAC AAT TTC AAC GAA CAA CAA CAA AAT
436   Ala Val Thr Arg Ser Ala Asp Asn Asn Phe Asn Glu Gln Gln Gln Asn

1404  GCT TTC TAT GAA ATC TTG AAT ATG CCT AAC TTA AAC GAA GAA CAA CGC
452   Ala Phe Tyr Glu Ile Leu Asn Met Pro Asn Leu Asn Glu Glu Gln Arg

1452  AAT GGT TTC ATC CAA AGC TTA AAA GAT GAC CCA AGC CAA AGT GCT AAC
468   Asn Gly Phe Ile Gln Ser Leu Lys Asp Asp Pro Ser Gln Ser Ala Asn
```

FIG. 19E

```
1500   CTA TTG TCA GAA GCT AAA AAG TTA AAT GAA TCT CAA GCA CCG AAA GAT
484    Leu Leu Ser Glu Ala Lys Lys Leu Asn Glu Ser Gln Ala Pro Lys Asp

1548   CGA TCC GCC TGA  TCAATGCAACGACACATCATGATCTGCTGCACTTAATTACTATG
500    Arg Ser Ala End

1607   TTCGTATACAAATAAATACACCCGGCGTACGCGGGTGTTCCTTATATGGTCTAAAATGTAGCCA

1670   GTAAATTTTAAACTACTTTCTCGTGCCGAATTCACTGGCCCGGCATGCTATATA
```

RIBOSOME-INACTIVATING PROTEINS, INACTIVE PRECURSOR FORMS THEREOF, A PROCESS FOR MAKING AND A METHOD OF USING

This is a Divisional of U.S. Ser. No. 378,761 which was filed on Jan. 26, 1995 which was a continuation application of U.S. Ser. No. 987,927 filed Dec. 9, 1992, which is now abandoned, which was a continuation-in-part of U.S. Ser. No. 535,636 filed Jun. 11, 1990 which is now U.S. Pat. No. 5,248,606.

FIELD OF THE INVENTION

The present invention relates to recombinant biology and specifically to ribosome-inactivating proteins.

BACKGROUND OF THE INVENTION

Ribosome-inactivating proteins (RIPs) are plant proteins that are capable of catalytically inactivating eukaryotic ribosomes and are consequently extremely potent inhibitors of eukaryotic protein synthesis. RIPs have been divided into two classes: type 1 and type 2 RIPs (see Barbieri and Stirpe (1982), *Cancer Surveys*, 1:489–520). There is significant amino acid sequence homology between members of both type 1 and type 2 RIPs, and with the bacterial Shiga and Shiga-like toxins which also have the same mechanism of action (see Hovde et al. (988), *Proc. Natl. Acad. Sci. USA*, 85:2568–2572).

Type 2 RIPs consist of two polypeptides; an RIP (or A-chain) which is covalently attached via a disulfide bond to a lectin-like protein (or B-chain). The B-chain binds to ceil surface carbohydrates and facilitates subsequent cellular internalization of the RIP A-chain moiety, which results in rapid inactivation of protein synthesis and cell death. Type 2 RIPs are therefore extremely potent cytotoxins and animal poisons, the best studied example of which is ricin.

In contrast, type 1 RIPs characterized to date consist of a single polypeptide chain equivalent in activity to that of A-chain RIPs but lacking a covalently attached B-chain. Consequently, type 1 RIPs are scarcely toxic to intact cells but retain their extreme potency against cell-free protein translation systems. Typical $IC_{50}$ concentrations of type 1 RIPs are 0.5 to 10 ng/ml (0.16 to 33 pM). Until the discoveries detailed hereinbelow, reported type 1 RIPs were a remarkably homogeneous class of basic proteins with Mr values of about 30,000. Type 1 RIPs are found in a great variety of dicot and monocot plants and they may be ubiquitous. They are often abundant proteins in seeds, roots or latex for example. Their in vivo Function is unclear but it has been proposed that they may be antiviral agents (see Stevens et al. (1981), *Experientia*, 37:257–259) or antifungal agents (see Roberts and Seltrennikkoff (1986), *Bioscience Reports*, 6:19–29).

To date, one article has discussed the presence of an inhibitor of animal cell-free protein synthesis in maize, as well as other cereal crops (see Coleman and Roberts (1982), *Biochimica et Biophysica Acta*, 696:239–244). The preparation of the maize inhibitor was via ammonium sulfate precipitation and phosphocellulose column chromatography. It is generally believed that the inhibitor isolated from maize was pure. The reported molecular weight of the inhibitor was 23 kiloDaltons (kD), with a reported $IC_{50}$ of 50 to 100 ng/ml in an ascites cell-free protein synthesis assay.

Where the effect of RIPs on ribosames has been examined, both type 1 and type 2 RIPs possess a unique and highly specific N-glycosidase activity which cleaves the glycosidic bond of adenine 4324 of the rat liver ribosomal 28S RNA (see Endo (1988), In:*Immunotoxins*, Frankel (ed.), suprs).

Commercial interest in RIPs has primarily focused on their use in construction of therapeutic toxins targeted to specific cells such as tumor cells by attachment of a targeting polypeptide, most frequently a monoclonal antibody (see *Immunotoxins* (1988), supra). This mimics the binding functionality of the B-chain of type 2 RIPs but replaces the non-specific action of B chains with a highly selective ligand. Another recent potential use is in HIV therapy (see U.S. Pat. No. 4,869,903 to Lifson et al., (Gonelabs Incorporated and The Regents of the University of California)).

However, while a maize-derived protein synthesis inhibitor, like protein synthesis inhibitors from other Panicoideae, would appear to be useful for construction of cytotoxic conjugates, no artisan to date has reported to have successfully characterized a Panicoideae RIP. This is somewhat surprising in view of the success achieved with RIPs from non-Panicoideae plants, including cereals such as barley (see Lambert et al. (1988), In:*Immunotoxins*, supra). In part, the lack of success to date by skilled artisans in successfully utilizing the maize RIP described by Coleman and Roberts may be attributed to the fact that the protein synthesis inhibitor was relatively uncharacterized and reported $IC_{50}$ was relatively poor.

There is interest in expressing recombinant RIP in commonly employed host eukaryotic cells, because of the capacity to provide correct post-translational processing. However, as RIPs effectively inhibit protein synthesis in eukaryotic cells, a predictable problem is that heterologous expression of an RIP will result in host cell death. Thus, eukaryotic cells are generally not used as recombinant host cells. Although eukaryotic cells may be used in certain circumstances, the RIP must be constructed so as to be secreted prior to the cell experiencing toxicity (see EP 0 335 476 to Gelfand et al. (Cetus Corp.)). Therefore, prokaryotic host cells are generally used as hosts, notwithstanding disadvantages such as the inability to glycosylate and properly fold heterologously-expressed proteins.

It is thus an object of the invention to provide a method of preparing inactive forms of RIPs, in which an inactive RIP may be expressed by eukaryotic host cells and then converted to an active form.

It is yet another object of the invention to provide the DNA sequence of a gene encoding at least one inactive form of RIP, as well as expression vehicles, host cells and cell cultures containing such DNA sequence.

Other objects and advantages of the present invention will become apparent from the teachings presented hereinafter.

It is to these objects to which the present invention is directed.

SUMMARY OF THE INVENTION in a first aspect, the present invention is directed to a substantially pure protein having an amino acid sequence effectively homologous to the amino acid sequence set forth in FIG. 1, termed a proRIP, wherein the proRIP has a selectively removable, internal peptide linker sequence and is incapable of substantially inactivating eukaryotie ribosomes, but which can be converted by removal of the linker into a protein having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a second aspect, the present invention is directed to a substantially pure protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and α-trichosanthin RIP, Luffin-A RIP, and Mirabills antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In a third aspect, the present invention is directed to a substantially pure protein, termed an RIP, having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a fourth aspect, the present invention is directed to a fusion protein capable of substantially inactivating eukaryotic ribosomes, said protein having an amino acid sequence effectively homologous to one of the amino acid sequences set forth in FIGS. 8, 10, 11, 12, 13, 14, 15, 16, 17, 18 or 19.

In a fifth aspect, the present invention is directed to a conjugate comprising a targeting vehicle and a protein, termed a proRIP, wherein the proRIP has a selectively removable, internal peptide linker sequence and is incapable of substantially inactivating eukaryotic ribosomes, but which can be converted by removal of the linker into a protein having α and β fragments and being capable of substantially inactivating eukaryotic ribosomes, wherein the α fragment has an amino acid sequence effectively homologous to residues 17 to 161 of FIG. 1 and the β fragment has an amino acid sequence effectively homologous to residues 187 to 287 of FIG. 1.

In a sixth aspect, the present invention is directed to a conjugate comprising a targeting vehicle and a fusion protein that is capable of substantially inactivating eukaryotic ribosomes, said protein having an amino acid sequence effectively homologous to an amino acid sequence set. forth in FIGS. 8, 10, 11, 12, 13, 14, 15, 16, 17, 18 or 19.

In a seventh aspect, the present invention is directed to a conjugate comprising a targeting vehicle and a protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and a-trichosanthin RIP, Luffin-A RIP, and Mirabills antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In a eighth aspect, the present invention is directed to a method for converting a proRIP into an RIP, said method comprising the following steps:
a) providing a homogeneous protein, termed a proRIP, wherein the proRIP has a selectively removable, internal peptide linker sequence and is incapable of substantially inactiveting eukaryotic ribosomes, but which can be converted by removal of the linker into a protein having α and β fragments, termed an RIP, that is capable of substantially inactivating eukaryotic ribosomes; and
b) contacting the proRIP with a cleaving agent capable of deleting the linker to form a protein having α and β fragments, termed an RIP, that is capable of substantially inactivating eukaryotic ribosomes.

In a ninth aspect, the present invention is directed to DNA isolate encoding a protein, said protein having an amino acid sequence effectively homologous to the amino acid sequence set forth in FIG. 1, termed a proRIP, wherein the proRIP has a selectively removable, internal peptide linker sequence and is incapable of substantially inactiveting eukaryotic ribosomes, but which can be converted by removal of the linker into a protein having α and β fragments and being capable of substantially inactiveting eukaryotic ribosomes, wherein the a fragment has an amino acid sequence effectively homologous to residues 17 to 161 of FIG. 1 and the β fragment has an amino acid sequence effectively homologous to residues 187 to 287 of FIG. 1.

In a tenth aspect, the present invention is directed to a DNA sequence encoding a protein being capable of substantially inactivating eukaryotic ribosomes, said protein having an amino acid sequence effectively homologous to one of the amino acid sequences set forth in FIGS. 8, 10, 11, 12, 13, 14, 15, 16, 17, 18 or 19.

In an eleventh aspect, the present invention is directed to a DNA isolate encoding a protein, termed a proRIP, wherein the proRIP has a selectively removable, internal peptide linker sequence and is incapable of substantially inactivating eukaryotic ribosomes, but which can be converted by removal of the linker into a protein having α and β fragments, termed an RIP, that is capable of substantially inactivating eukaryotic ribosomes, said proRIP comprising (1) a Panicoideae RIP selected from barley RIP, ricin A-chain RIP, saporin RIP, abrin A-chain RIP, SLT-1 RIP, and α-trichosanthin RIP, Luffin-A RIP, and Mirabills antiviral protein RIP and (2) a removable, internal peptide linker sequence inserted between amino acid residues 152–162 of Ricinus communis agglutinin, amino acid residues 138–148 of Abrin-a A-chain, amino acid residues of 138–148 of Luffin-a, 139–149 of Luffin-b, amino acid residues of 138–148 Momordin, amino acid residues 139–149 of Trichosanthin, amino acid residues 151–161 of PAP-S, amino acid residues 145–155 of MAP, amino acid residues 153–163 of Saporin, amino acid residues 148–158 of Barley Translation Inhibitor and amino acid residues 174–184 of Dianthin 30.

In other aspects, the invention is directed to expression vehicles capable of effecting the production of such aforementioned proteins in suitable host cells. It also includes the host cells and cell cultures which result from transformation with these expression vehicles.

BRIEF DESCRIPTION OF THE DRAWINGS

A number of aspects of the present invention are further illustrated in the accompanying Drawings, in which:

FIGS. 1*a* through 1*c* collectively depicts an intact recombinant maize proRIP nucleotide sequence (SEQ. ID. NO. 1) and amino acid sequence (SEQ. ID. NO. 2) of a protein of Mr 33,327.

FIG. 3 shows a comparison of the maize proRIP amino acid sequence with that of barley RIP.

FIG. 4 shows a comparison of the maize proRIP amino acid sequence with that of ricin A-chain.

FIGS. 5A shows the comparative alignment of the N-terminal amino acid sequence of an α fragment of the maize αβ RIP α fragment with the N-terminal sequences of RIPs from other sources; and FIGS. 5B shows the alignment of maize αβ RIP with regions of homology in the amino acid sequences of other RIPs.

FIGS. 7*a* through 7*b* collectively depicts a cDNA sequence of (SEQ. ID. NO. 3) the maize pro-RIP sequence engineered for expression in *Escherichia coli.*

FIGS. 8*a* through 8*c* collectively depicts a predicted DNA sequence (SEQ. ID. NO. 4) and deduced amino acid sequence (SEQ. ID. NO. 5) of R30.

FIGS. 10*a* through 10*c* depicts a predicted DNA sequence (SEQ. ID. NO. 6) and deduced amino acid sequence (SEQ. ID. NO. 7) of R34-DL.

FIGS. 11*a* through 11*c* depicts a predicted DNA sequence (SEQ. ID. NO. 8) and deduced amino acid sequence (SEQ. ID. NO. 9) of R30-DL.

FIGS. 12*a* through 12*c* depicts the predicted DNA sequence (SEQ. ID. NO. 10) and deduced amino acid sequence (SEQ. ID. NO. 11) for RDT.

FIGS. 13*a* through 13*c* collectively depicts the predicted DNA sequence (SEQ. ID. NO. 12) and deduced amino acid sequence (SEQ. ID. NO 13) for RDT-NP.

FIGS. 14*a* through 14*d* collectively depicts the predicted DNA sequence (SEQ. ID. NO. 14) and deduced amino acid sequence (SEQ. ID. NO 15) of RDT-A.

FIGS. 15*a* through 15*d* collectively depicts the predicted DNA sequence (SEQ. ID. NO. 16) and deduced amino acid sequence (SEQ. ID. NO 17) of RDT-G-A.

FIGS. 16*a* through 16*e* collectively depicts the predicted DNA sequence (SEQ. ID. NO. 18) and deduced amino acid sequence (SEQ. ID. NO. 19) of RDT-G-G-A.

FIGS. 17*a* through 17*c* collectively depicts the predicted DNA sequence (SEQ. ID. NO. 20) and deduced amino acid sequence (SEQ. ID. NO. 21) of RDT-BHSR.

FIGS. 18*a* through 18*e* collectively depicts the predicted DNA sequence (SEQ. ID. NO. 22) and deduced amino acid sequence (SEQ. ID. NO. 23) of RDT-BHS-GGA.

FIGS. 19*a* through 19*e* collectively depicts the predicted DNA sequence (SEQ. ID. NO 24) and deduced amino acid sequence (SEQ. ID. NO. 25) of RDT-DS-GGA.

DETAILED DESCRIPTION OF THE INVENTION

Figure 2:
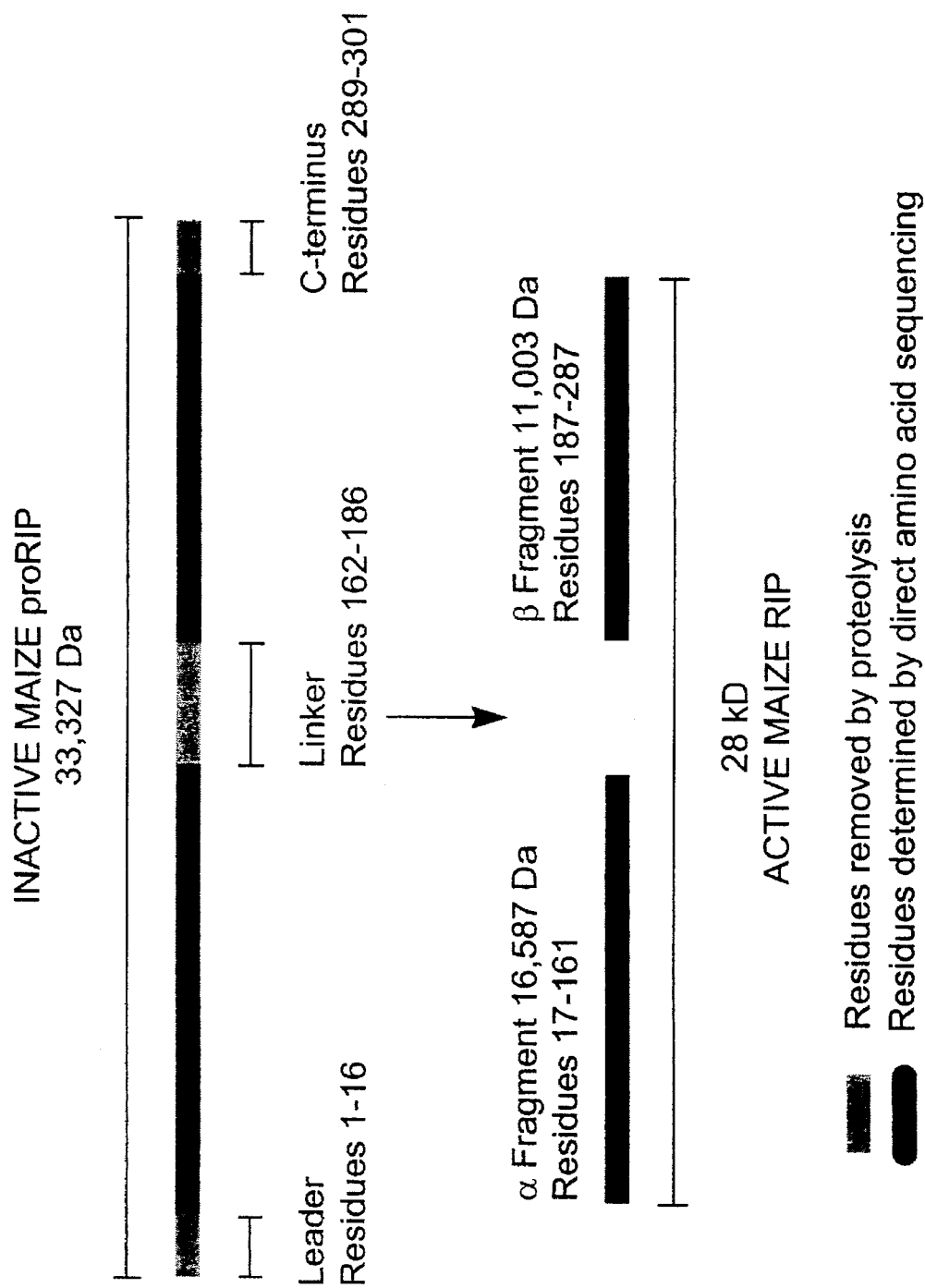
FIG. 2 shows a schematic representation of the processing of maize proRIP to an active RIP.

The entire teachings of all references cited herein are incorporated by reference.

Definitions

Nucleic acids, amino acids, peptides, protective groups, active groups and so on, when abbreviated, are abbreviated according to the IUPACIUB (Commission on Biological Nomenclature) or the practice in the fields concerned.

The term "proRIP" means a precursor protein that contains an amino-terminal segment, a linker and a carboxy-terminal segment and that is not capable of inactivating eukaryotic ribosomes.

The term "leader" refers to an N-terminal amino acid sequence of a proRIP that need not be present in the mature, fully active form of the αβ RIP.

The term "linker" refers to an internal amino acid sequence within a proRIP, whereby the linker is of a length and contains residues effective to render the proRIP incapable of catalytically inhibiting translation of a eukaryotic ribosome.

The term "RIP" means a protein that is capable of inactiveting eukaryotic ribosomes. The term "αβ RIP" means an RIP having an α fragment, which may or may not contain a leader, and a β fragment and being capable of substantially inactivating eukaryotic ribosomes.

The term "$IC_{50}$" means the concentration of a protein necessary to inhibit protein synthesis by 50 percent in a cell-free protein synthesis assay.

The term "inhibiting amount" refers to the specific ability of RIPs to cause the death or injury of cells against which they are targeted.

The term "target cells" means those cells having ribosomes which the αβ RIP of the present invention is capable of inhibiting. The target cells may be present in living organisms or they may be preserved or maintained in vitro. The cells may be individual or associated to form an organ. Exemplary target cells include any eukaryotic cell (e.g., mammalian, insect, fungal and plant cells).

The term "targeting vehicle" means a carrier moiety containing a ligand capable of binding to a receptor of a specific cell or tissue.

"Gene" refers to the entire DNA portion involved in the synthesis of a protein. A gene embodies the structural or cading portion which begins at the 5' end from a translation start codon and extends at the 3' end to a stop codon. It also contains a promoter region, usually located 5' or upstream to the structural coding portion, which initiates and regulates the expression of a structural gene and a 3' nontranslated region downstream from the translated region.

"Expression" refers to a two-part process for the transcription and translation of a gene. The DNA defining the gene is transcribed into a precursor RNA, which is processed to its mature form, messenger RNA (mRNA). During translation, the cell's ribosomes, in conjunction with transfer RNA, translate the RNA "message" into proteins.

PREFERRED EMBODIMENTS OF THE INVENTION

Surprisingly, it has been discovered that studied members of Panicoideae contain αβ RIP and proRIP. Panicoideae is a subfamily of Gramineae (order) and Graminaceae (family). The subfamily Panicoideae contains three tribes: Maydeae (e.g., Tripsacura, Coix, Euchlaena and Zea), Andropogoneae (e.g., Sorghum) and Paniceae. For further taxonomic information, see Arber ( 1934), *The Gramineae, A Study of Cereal, Bamboo and Grass*, Cambridge University Press, p 410–411.

The present invention pertains to proteins which are derived from a plant within the subfamily Panicoideae. As taught herein, proteins obtained from various plants within the subfamily Panicoidae have shown antigenic cross reactivity (i.e., showing evidence of proRIP in Panicoideae well as α and β fragments of an αβ RIP).

By "derived" from a plant within the subfamily Panicoideae means a protein that is effectively homologous, as defined below, with a proRIP or αβ RIP from Panicoideae, regardless of the manner in which the protein is produced. Given the present teachings it now becomes possible to prepare generally homogeneous proRIP and αβ RIP exclusive of irrelevant proteins and contaminants naturally associated therewith in the cellular environment or in extracellular fluids. For example, a substantially pure protein will show constant and reproducible characteristics within standard experimental deviations for parameters such as the following: molecular weight, chromatographic behavior, and such other parameters. The term, however, is not meant to exclude artificial or synthetic mixtures of a protein with other compounds. The term is not meant to exclude the presence of minor impurities which do not interfere with the biological activity of the protein and which may be present, for example, due to incomplete purification.

Both the proRIP and αβ RIP may be purified directly from mature and germinating seeds and developing kernels of plants within the subfamily. Generally, the purification of the Panicoidae αβ RIP and proRIP may be accomplished as set forth below.

Seeds or immature kernels of plants within the subfamily Panicoideae may be homogenized to disrupt the individual seeds or kernels. This can be accomplished by any type of commercially available homogenizer.

The Panicoideae proRIP and/or αβ RIP may be purified from the homogenization product by any appropriate protein purification technique. Exemplary techniques include gel filtration chromatographic techniques, such as conventional liquid chromatography, ion exchange chromatography, high performance liquid chromatography, and reverse phase chromatography.

Upon purification, the Panicoideae proRIP will have insignificant ribosome inactivating ability relative to its corresponding αβ RIP. For example, maize proRIP has an $IC_{50}$ of greater than about 10 micrograms per milliliter (μg/ml) in a cell-free protein synthesis assay, whereas the maize αβ RIP has an $IC_{50}$ of about 1 nanogram per milliliter (ng/ml) in a mammalian cell-free protein translation assay.

The maize proRIP has a molecular weight of about 34 kD, as determined by SDS-PAGE (see Laemmli (1970), supra), and will move as a single peak on ion exchange chromatography. Homogeneous maize αβ RIP will comprise two associated fragments, an α and β fragment, having molecular weights of approximately 16.5 kD and 11.0 kD, respectively (as determined by sodium dodecyl sulfate polyacrylamide-gel electrophoresis (SDS-PAGE), see Laemmli (1970), Nature, 22:680–685). The homogeneous protein will exhibit two dissociated peaks on reverse phase chromatography, and a single associated peak on ion exchange chromatography. Polyclonal anti-sera against each fragment both crossreact with a polypeptide present in maize kernels having a molecular weight of about 34 kD as determined by SDS-PAGE. This demonstrates that the two fragments of the maize αβ RIP are in fact derived from a common precursor (i.e., the maize proRIP).

The maize proRIP amino acid sequence (as set forth in FIG. 1) contains five sequence subsegments: (1) a leader sequence, from residues 1 to 16, (2) an α fragment, from residues 17 to 161, (3) an internal linker sequence, from residues 162 to 186, and (4) a β fragment, from residues 187 to 287 and a C-terminal segment from residues 288–301.

The net charges of these polypeptides are as follows: leader sequence −3; a fragment, +10; linker, −5; β fragment, +6 and C-terminal segment, −5. Removal of the leader and linker results in a dramatic change in net charge from the maize proRIP (+3) to maize αβ RIP (+16). Additionally, the proRIP isolated from maize has an observed pI of about 6.5 which agrees well with the value of about 6.1 derived from the deduced amino acid sequence. The pI of the active maize αβ RIP is ≧9, compared to the calculated value from the deduced amino acid sequence of about 9.06 (i.e., after deletion of the acidic leader, linker and C-terminal sequences). Thus, the maize αβ RIP has a basic pI, which is consistent with the pI of other RIPs.

When the internal linker sequence of the proRIP is removed (see FIG. 2), the αβ RIP has significant ribosome inactivating activity. The activity has been found to be significant regardless of whether the leader sequence has been removed (e.g., by recombinant methods). However, the proRIP is most active when the leader sequence is also removed and when up to fourteen C-terminus residues are also removed. In nature, it is thought that the linker is cleaved by endogenous proteases released by germinating seeds. Significantly, it has been discovered that the linker may also be cleaved in vitro by certain proteases, e.g., papain, subtilisin Carlberg to yield active maize αβ RIP from the precursor. While not intended to be bound by theory, it is thought that papain likely mimics the effect of endogenous endoproteinases released during germination.

It appears that, after removal of the internal linker, the two fragments of the processed polypeptide are held together by noncovalent forces. That is, the association of the two polypeptide chains does not depend upon interchain disulfide bonds or the formation of a peptide bond between the fragments.

Although not intended to be bound by theory, it is believed that the linker forms an external loop with exposed amino acid residues that are susceptible to proteolysis. Support for this suggestion comes from the alignment of the amino acid sequence of the maize proRIP with that of ricin A chain, the three dimensional structure of which is known (see Montfort et al, (1987), J. Biol. Chem., 262:5398). The Glu 177, Arg 180, Asn 209 and Trp 211 of ricin A have been implicated in the active site region of the molecule (see Robertus (1988), In:Immunotoxins, supra).

Based on this alignment, homologous residues of maize αβ RIP can be positioned within the three dimensional structure of ricin A chain. The superimposed structures indicate that the C-terminal lysine of the α fragment (at residue 162) is in corresponding alignment with an externally positioned threonine (at residue 156) of the ricin A-chain. Also, the N-terminal alanine of the β fragment (at residue 187) is in corresponding alignment with an externally positioned glycine (at residue 157) of the ricin A-chain.

Any of a variety of procedures may be used to clone proRIP-encoding gene sequence. One method for cloning the proRIP gene sequence entails determining the amino acid sequence of the proRIP molecule. To accomplish this task proRIP or αβ RIP protein may be purified (as described above), and analyzed to determine the amino acid sequence of the proRIP or αβ RIP. Any method capable of elucidating such a sequence can be employed, however, Edman degradation is preferred. The use of automated sequenators is especially preferred.

It is possible to synthesize in vitro the proRIP and αβ RIP from their constituent amino acids. A suitable technique includes the solid phase method (see Merrifield (1963), *J. Amer. Chem. Soc.*, 85:2149–2154; and *Solid Phase Peptide Synthesis* (1969), (eds.) Stewart and Young). Automated synthesizers are also available.

The peptides thus prepared may be isolated and purified by procedures well known in the art (see *Current Protocols in Molecular Biology* (1989), (eds.) Ausebel, et al., Vol. 1 and Sambrook et al. (1989), *Molecular Cloning: A Laboratory Manual*).

Using the amino acid sequence information, the DNA sequences capable of encoding them are examined in order to clone the gene encoding the proRIP. Because the genetic code is degenerate, more than one codon may be used to encode a particular amino acid.

Although it is possible to determine the entire amino acid sequence of the proRIP or αβ RIP, it is preferable to determine the sequence of peptide fragments of the molecule, and to use such sequence data to prepare oligonucleotide probes which can be used to isolate the entire proRIP gene sequence. The proRIP peptide fragments can be obtained by incubating the intact molecule with cyanogen bromide, or with proteases such as papain, chymotrypsin or trypsin.

Using the genetic code one or more different oligonueleotides can be identified. The probability that a particular oligonucleotide will, in fact, constitute the actual proRIP encoding sequence can be estimated by considering abnormal base pairing relationships and the frequency with which a particular codon is actually used (to encode a particular amino acid) in eukaryotic cells. Using these rules, a single oligonucleotide, or a set of oligonucleotides, that contains a theoretical "most probable" nucleotide sequence capable of encoding the proRIP or αβ RIP peptide sequences may be identified.

The oligonucleotide, or set of oligonucleotides, containing the theoretical "most probable" sequence capable of encoding the proRIP gone fragments may be used to identify the sequence of a complementary oligonucleotide, or set of oligonucleotides, which is capable of hybridizing to the "most probable" sequence, or set of sequences. An oligonucleotide containing such a complementary sequence can be employed as a probe to identify and isolate the toxin gene (see Sambrook et al. (1989), supra).

By hybridizing an oligonucleotide having a sequence complementary to the "most probable" gene sequence, one obtains a DNA molecule (or set of DNA molecules), capable of functioning as a probe to identify and isolate the proRIP gene.

The present invention also relates to DNA sequences that encode recombinant proRIP and αβ RIP. The recombinantly-produced proRIP and αβ RIP share the following properties with the proRIP and αβ RIP isolated from nature and characterized according to the teachings herein: (1) portions of the amino acid sequence deduced from the nucleotide sequence are equivalent to amino acid sequences obtained directly from nature; (2) the polypeptide is recognized by anti-RIP antibodies; (3) the molecular weight of the proRIP and αβ RIP polypeptides encoded corresponds with the naturally occurring proteins; (4) each proRIP protein is convertible to an αβ RIP; and (5) each proRIP and αβ RIP protein exhibits relatively equivalent ribosome inactivating activity.

The process for genetically engineering the proRIP or αβ RIP according to the invention is facilitated through the cloning of genetic sequences which are capable of encoding the proRIP or αβ RIP, or effectively homologous variants thereof as discussed below, and through the expression of such genetic sequences. As used herein, the term "genetic sequences" is intended to refer to a nucleic acid molecule (preferably DNA). Genetic sequences which are capable of encoding the toxin may be derived from a variety of sources. These sources include genomic DNA, cDNA, synthetic DNA, and combinations thereof.

Cells containing the desired sequence may be isolated, and genomic DNA fragmented by one or more restriction enzymes. The genomic DNA may or may not include naturally-occurring introns. The genomic DNA digested with selected restriction endonucleases yields fragments containing varying numbers of base pairs (bp).

Specifically comprehended as part of this invention are genomic DNA sequences encoding allelic variant forms of the proRIP gene which may or may not include naturally occurring introns. The allelic gene may be derived using a hybridization probe made from the DNA or RNA of the proRIP gene as well as its flanking regions. "Flanking regions" are meant to include those DNA sequences 5' and 3' of the proRIP encoding sequences.

The DNA isolate encoding the proRIP gene may also be obtained from a cDNA library. The mRNA may be isolated from a suitable source employing standard techniques of RNA isolation, and the use of oligo-dT cellulose chromatography to enrich for poly-A mRNA. A cDNA library is then prepared from the mixture of mRNA using a suitable primer, preferably a nucleic acid sequence which is characteristic of the desired cDNA. A single stranded DNA copy of the mRNA is produced using the enzyme reverse transcriptase. From the single stranded cDNA copy of the mRNA, a double-stranded cDNA molecule may be synthesized using either reverse transcriptase or DNA polymerase.

It is also possible to use primers to amplify the DNA from cells of appropriately prepared seeds and immature kernels by the polymerase chain reaction (PCR). PCR involves exponentially amplifying DNA in vitro using sequence specified oligonucleotides (see Mullis et al. (1987), *Meth. Enz.*, 155:335–350); Horton et al. (1989), *Gene*, 77:61; and *PCR Technology: Principles and Applications for DNA Amplification*, (ed.) Erlich (1989).

The DNA encoding the proRIP or αβ RIP may be chemically synthesized by manual procedures, e.g., the phosphotriester and phosphodiester methods (see Caruthers (1983), In:*Methodology of DNA and RNA*, (ed.) Weissman); or automated procedures, e.g., using diethylphosphoramidites are used as starting materials (see Beaucage et al. (1981), *Tetrahedron Letters*, 22:1859–1962). The DNA may be constructed by standard techniques of annealing and ligating fragments or by other methods.

Thereafter, the desired sequences may be isolated and purified by procedures well known in the art (see *Current Protocols in Molecular Biology* (1989), supra and Sambrook et al. (1989), *Molecular Cloning: A Laboratory Manual*, supra).

The nucleotide sequence of the maize proRIP cDNA and the deduced amino acid sequence of such the corresponding maize proRIP is set forth in FIG. 1. However, one need not be confined to the amino acid sequences of proRIP and αβ RIP found in nature. Thus, it is possible to selectively produce both proRIP and αβ RIP via the application of recombinant DNA technology. This in turn allows the production of sufficient quality and quantity of material to create novel forms of the protein unimpeded by the restriction necessarily inherent in the isolation methods involving production and extraction of the protein from natural sources.

A comparison of the maize proRIP (SEQ ID NO:2) with that of barley, a monocot, is set forth in FIG. 3. The upper sequence shows maize αβ RIP and the lower sequence barley RIP (SEQ. ID. NO. 26), as taught by Asano et al. (1986), *Carlsberg Res. Commun.*, 51:129. Identical residues are denoted by a solid line, conservative substitutions by a dotted line, and dashes indicate insertions to maximize homology. Residues are numbered on the left.

As set forth in in FIG. 3, there is an overall homology of about 28 percent (about 34 percent including conservative substitutions) between the maize αβ RIP and barley RIP. However, the unique nature of the linker region of maize proRIP is clearly shown by the resulting gap that has been introduced in the published barley sequence to maintain homology. A lower, but significant, degree of homology is seen when the maize proRIP (SEQ ID NO:2) sequence is compared to the sequence of ricin A-chain (as set forth in FIG. 4). The upper sequence is maize αβ RIP and the lower sequence is ricin A (SEQ. ID. NO. 27), as taught by Lamb et al. (1985), *Eur. J. Biochem.*, 148:265. Identical residues are denoted by a solid line and conservative substitutions by a dotted line, dashes indicate insertions to maximize homology. Residues are numbered on the left, the numbering of the ricin sequence corresponds to that of the mature protein.

As set forth in FIG. 4, a gap was again introduced in the published ricin A sequence to maximize homology corresponding to the linker region of the maize proRIP.

Further comparison of the maize proRIP sequence with published full-length sequences of other non-Panicoideae RIPs indicate that there are four regions of significant homology between these proteins (as set forth in FIGS. 5a and 5b).

FIG. 5A shows the first region and the comparative alignment of the N-terminal amino acid sequence of the maize αβ RIP α fragment residues 13 to 49 of SEQ ID NO: 2 with the N-terminal sequences of RIPs from other sources. The sequences are taken from: barley (residues 1 to 39 of SEQ ID NO: 26) (see Asano et al. (1986), supra); ricin A-chain (residues 25 to 58 of SEQ ID NO: 27) (see Lamb et al. (1985), supra); dodecandrin (SEQ. ID. NO. 28) (see Ready et al. (1985), *Biochem. Biophys, Acta,* 791:314); pokeweed anti-viral protein 2 (SEQ. ID. NO. 29) (see Bjorn et al. (1985), *Biochim. Biophys. Acta,* 790:154); Shiga-like toxin (SEQ. ID. NO. 30) (see Calderwood et al. (1987), *Proc. Nat. Acad. Sci. USA,* 84:4364); and α-trichosanthin (SEQ. ID. NO. 31), momordins (SEQ. ID. NO. 32), bryodin (SEQ. ID. NO. 33), gelonin (SEQ. ID. NO. 34), dodecandrin, pokeweed antiviral protein-2, saporin 5 (SEQ. ID. NO. 35) and saporin 4 (SEQ. ID. NO. 36) (see Montecucchi et al. (1989), *Int. J. Peptide Res.,* 33:263). Positions showing homology in four or more sequences are noted by solid lines (showing identical residues) or dotted lines (showing conservatively substituted residues).

FIG. 5b shows that the other three regions are internally oriented. FIG. 5b specifically shows. the alignment of maize αβ RIP residues 84 to 98; 201 to 215 and 237 to 249 of SEQ ID BIL 2 with regions of homology in the amino acid sequences of other RIPs. The sequences are available from the following references: barley (residues 76 to 91; 168 to 182 and 208 to 218 of SEQ ID NO: 26) (see Asano et al. (1986), supra and Leah et al. (1991), *J Biol. Chem.*, 266:1564–1573); ricin A-chain (residues 70 to 84; 171 to 185 and 207 to 217 of SEQ ID NO: 27) (see Lamb et al. (1985), supra); abrin A-chain (SEQ. ID. NO. residues 64 to 78 are SEQ ID NO: 47, residues 159 59 173 are SEQ ID NO: 48 and residues 194 to 204 are SEQ ID NO: 49) (see Funatsu et al. (1988), *Agric. Biol. Chem.* 52:1095); saporin-6 (SEQ. ID. NO. residues 62 to 76 are SEQ ID NO: 37, residues 170 to 184 are SEQ. ID. No. 38 and residues 205 to 214 are SEQ ID NO: 46) (see Benatti et al. (1989) *Eur. J. Biochem.,* 183:465); Shiga-like toxin 1A (residues 62 to 76 are SEQ ID NO: 50, residues 183 to 197 are SEQ ID NO: 51 and residues 222 to 231 are SEQ ID NO: 52) (see Calderwood et al. (1987), supra); and α-trichosanthin (residues 58 to 67 are SEQ ID NO: 53, residues 77 to 81, residues 161 to 175 are SEQ ID NO: 54, residues 161 to 175, residues 196 to 207 are SEQ ID NO: 55, and residues 196 to 207 are SEQ ID NO: 56) (see Montecucchi et al. (1989), supra); Xuejun and Jiahuai (1986), *Nature,* 321:477; Chow et al. (1990), *J. Biol. Chem.,* 265: 8670–8674 and Maragonore et al. (1987), *J. Biol. Chem.,* 262:11628–11633). Positions showing identity or conservative substitutions in four or more sequences are underlined, dashes indicate insertions to maximize homology. Vertical lines indicate residues that are conserved in all seven sequences. The starting amino acid of each sequence is indicated (note that trichosanthin contains an insertion sequence at residues 67 to 76).

The sequences and partial sequences of various additional Type I RIPs are set forth in the following articles: luffin-A (see Islam et al. (1990), *Agric. Biol. Chem.,* 54:2967–2978); mirabilis antiviral protein (see Habuka et al. (1989) *J. Bio. Chem.,* 264:6629–6637); trichokirin, (see Casellas et al. (1988), *Eur. J. Bioehem.,* 176:581–588); momordins (see Barbieri et al. (1980), *Biochem. J.,* 186:443–452); dianthins (see Reisbig and Bruland (1983), *Arch. Bioehem. Biophys.,* 224:700–706); saporins (see Maras et al., (1990), *Biochem. Intl.,* 21:831–838) and Lappi et al. (1985), *Biochem. Biophys. Res Commun.,* 129:934–942; and momoreoehin-S (see Bolognesi et al. (1989), *Biochim. Biophys. Acta,* 993:287–292).

As set forth in FIG. 5b, RIPs for which a full-length sequence has been determined contain regions with significant homology. Additionally, the similarities of N-terminal sequences in an even greater number of RIPs have been compared (set forth in FIGS. 5a and 5b). It is likely that these regions have particular effect upon the function of the respective RIPs. The RIPs set forth in FIG. 5a are intended for exemplification purposes only. RIPs characterized in the future that meet the above criteria are also considered to be a part of this invention.

An RIP having a known amino acid sequences may now be altered into an inactive, proRIP form by the insertion of a linker, wherein the insertion of the linker substantially reduces the ribosome inactivating ability of the RIP. By "substantially reduce" is meant that the insertion of a cleavable linker into an active RIP lowers the IC$_{50}$ value of the resultant protein by at least 10-fold, preferably 100-fold, and more preferably 1000-fold.

Based on the information deduced from the maize system set forth herein, it now becomes possible to engineer inactive forms of any RIP having a three dimensional structure similar to the three dimensional structure of ricin A chain. Cleavage of the linker will result in an αβ RIP not heretofore found in nature.

The art has discussed the methodology for modifying the three dimensional structure of proteins (see, for example, Van Brunt (1986), *Biotechnology,* 4:277–283). The first step involves selecting plausible sites on the RIP between which the linker may be inserted. One of those sites is the exposed amino acid residues surrounding residue 156 of ricin A-chain or its equivalent in other RIP sequences. Residue 156 is located in a surface loop connecting helices D and E in the three dimensional structure of Ricin A. Thus, the present invention is intended to encompass the insertion of a peptide linker within a surface loop analogous to the surface loop of connecting helices D and E in the three dimensional structure of Ricin A, provided that the insertion of the linker substantially reduces the ribosome inactiveting ability of the RIP. Specifically, in the surface loop connecting helices D and E in the three dimensional structure of Ricin A is defined by amino acids 152–162 (as published by Funatsu, et al. (1991), *Biochimie*, 73:1157–1161).

As stated previously, ricin A-chain has been shown to have sequence homology to many single chain RIPs. The present invention is intended to include the construction of αβ RIP and proRIP forms of any RIP. For example, regions in other RIPs analogous to amino acid sequence 152–162 in ricin A chain are as follows:

| RIP | Amino Acid Numbers* |
|---|---|
| Ricinus communis agglutinin | 152–162 |
| Abrin-a A-chain | 138–148 |
| Luffin-a | 138–148 |
| Luffin-b | 139–149 |
| Momordin | 138–148 |
| Trichosanthin | 139–149 |
| PAP-S | 151–161 |
| MAP | 145–155 |
| Saporin | 153–163 |
| Barley Translation Inhibitor | 148–158 |
| Dianthin 30 | 174–184 |

*All amino acid numbers are taken from Funatsu, et al. (1991), supra, except for the amino acid numbers for Dianthin 30, which are taken from Legname, et al. (1991), Biochimica et Biophysica Acta., 1090: 119–122.

Other Type I and Type II RIPs have also been purified to homogeneity and these include; momorcharins (see Yeung et al. (1986), *Int. J. Peptide Res.*, 28:518–524); tritins (see Roberts and Stewart (1979), Biochem., 18:2615–2621); rye (see Coleman and Roberts (1982), *Biochim. Biophys. Acta*, 696:239–244); agrostins and RIPs from *Hura crepitans* (see Stirpe et al. (1983), *Biochem. J.*, 216:617–625); *Asparagus officianalis* (see Stirpe et al. (1983), *Biochem. J.*, 216:617–625); *Cucumis melo* (see Ferreras et al. (1989), *Biochem Intl.*, 19:201–207); Cucurbitaceae (see Ng et al., *Int. J. Biochem.*, 21:1353–1358); Petrocoptis (see Ferreras et al., *Cell. Molec. Biol.*, 35:89–95); volkensin-a (see Barbieri et al. (1984), FEBS Lett., 171:277–279); viscumin-a (see Olsnes et al. (1982), *J. Biol. Chem.*, 257:13263–123270); modeccin-a (see Gasperi-Campani (1978), *Biochem. J.*, 174:491–496); *Momordia charantia* lectin-a (see Lin e tal. (1978), *Linn. Toxicon.*, 16:653–660 ); and *Phloraclerdron californicum* lectin-a (see Franz et al. (1989), *FEBS lett.*, 248:115–118).

Proteins from the following other plants have also been shown to possess ribosome inactivating activity: *Stellarea holostea, Lychnis flos-cuculi, Hordeum murinum, Aegylops geniculata, Euphorbia serrata, Capsella bursa-pastoris, Muscari comosum* (see Merino et al. (1990), *J. Exp Botany*, 41: 67–70); and proteins from *Croton tiglium* and *Jatropha curcas* (see Stirpe et al. ( 1976), *Biochem J.*, 156: 1–6).

Recombinant procedures make possible the production of effectively homologous proteins possessing part or all of the primary structural conformation and/or one or more of the biological properties of the αβ RIP. For purpose of this investigation, an amino acid sequence is effectively homologous to a second amino acid sequence if at least 70 percent, preferably at least 80 percent, and most preferably at least 90 percent of the active portions of the amino acid sequence are identical and retains its intended function. Thus more importantly and critical to the definition, an effectively homologous sequence to the αβ RIP retains the capacity to interact with and inactivate eukaryotic ribosomes. The effectively homologous sequence to the proRIP must retain the capacity to be converted into an αβ RIP. That is, the effectively homologous proRIP must have a linker sequence which, when cleaved, will yield a biologically functional αβ RIP.

General categories of potentially-equivalent amino acids are set forth below, wherein, amino acids within a group may be substituted for other amino acids in that group: (1) glutamic acid and aspartic acids; (2) lysine, arginine and histidine; (3) hydrophobic amino acids such as alanine, valine, leucine and isoleucine; (4) asparagine and glutamine; (5) threonine and serine; (6) phenylalanine, tyrosine and tryptophan; and (7) glycine and alanine.

It is envisioned that, compared with changes to the α and β fragments, more significant changes may be made to the proRIP in the leader and linker regions. That is, since the leader and linker sequences are to be cleaved, the length and amino acid residues in their sequences may better be tolerated and considered insignificant, because it will not alter the functionality of the final product.

Thus, the linker sequence of the proRIP need not be limited to the amino acid sequence set forth in FIG. 1. Generally, the linker may be of a length, may be of an amino acid sequence, and may be internally positioned so as to substantially reduce the ribosome inactivating activity of the RIP. Obviously, since the Panicoideae linker(s) is the only known RIP linker found in nature, it is expected that such an amino acid sequence will logically be a primary candidate for insertion into other RIPs. However the present invention is intended to encompass linkers having effectively homologous sequences to a selected maize linker. The factors to be considered in synthetically preparing effectively homologous linkers for αβ RIPs generally are the same as set forth above for selecting effectively homologous linkers for a selected maize linker. For example, the length of the linker may be modified, provided that (1) the linker is cleavable, and (2) upon cleavage of the linker the resultant protein has an $IC_{50}$ value that is at least about 10 times lower than the $IC_{50}$ value of the protein containing the linker.

Primary criteria for selecting an effectively homologous linker include altering the net charge of the αβ RIP (e.g., more acidic); creating a conformational shift in the protein or providing steric hindrance to the active site of the protein.

As noted previously, the maize αβ RIP, like other RIPs, is basic. However, the maize proRIP has a slightly acidic pI. Thus, it is preferred that any effectively homologous linker selected for the maize proRIP will be acidic.

The linker should be of a length which, while capable of altering the three-dimensional structure of the protein, when cleaved will permit the protein to retain most of the three dimensional features of the active αβ RIP molecule.

To ensure that the linker is clearable it is generally required that the conformation of the proRIP be such that the linker cleavage sites are readily accessible to a selected cleavage agent.

It is also envisioned that at least one restriction enzyme site may be engineered into the genetic sequence encoding an RIP, allowing DNA sequences encoding various polypeptide linkers to be inserted into the gene and tested for their ability to create an inactive, yet activatable RIP.

Nucleotide replacement may be achieved by the addition, deletion or substitution of various nucleotides, provided that the proper reading frame is maintained. Exemplary techniques for nucleotide replacement include polynucleotidemediated, site-directed mutagenesis, i.e., using a single strand as a template for extension of the oligonucleotide to produce a strand containing the mutation (see Zoller et al. (1982), *Nuc. Acids Res.*, 10:6487–6500); Norris et al. (1983), *Nuc. Acids Res.*, 11:5103–5112; Zoller et al. (1984), *DNA*, 3:479–488; and Kramer et al. (1982), *Nuc. Acids Res.*, 10:6475–6485) and PCR, i.e., using sequence specified oligonucleotides to incorporate selected changes by exponentially amplifying DNA in vitro (see *PCR Technology: Principles and Applications for DNA Amplification*, Erlich, (ed.) (1989), supra; and Horton et al., supra).

Most commonly, cleavage will be effected outside of the replicative environment, for example, following harvest of microbial culture. Thus, when genetically modifying the proRIP, it may be preferable, in some instances, that the internal linker domain of the proRIP be retained, or altered so as to mimic the manner in which a natural, inactive proRIP is processed to the active α and β fragments.

Any chemical or enzymatic method which recognizes a specific sequence or structure and causes an appropriate cleavage at a selected site may be utilized for the present invention. For example, it may be desirable to design carboxy termini and amino termini of the linker sequences that are subject to cleavage with selected agents. Exemplary of such sequences are Pro-Xxx-Gly-Pro (where Xxx is unspecified), which is selectively cleaved by collagenase; Ile-Glu-Gly-Arg, which is selectively cleaved by Factor Xa; and Gly-Pro-Arg, which is selectively cleaved by thrombin (see Nilsson et al. (1988), In: *Advances in Gene Technology; Protein Engineering and Production*, (ed.) Brew et al.).

A chemical or enzymetic method may not be suitable if its cleavage site occurs within the active amino acid sequences of the α and β fragments. That cleavage within the native amino acid sequence of the α and β fragments will generally have a greater likelihood of deleteriously affecting the enzymatic activity of the αβ RIP. It is possible to select a specific cleavage sequence of only one amino acid residue so long as that residue does is not accessible in the amino acid sequences of the α and β fragments. It is preferred, however, to utilize a specific cleavage sequence which contains two or more amino acid residues, i.e., an extended specific cleavage sequence. This type of sequence takes advantage of the extended active sites of various enzymes. Additionally, by utilizing an extended specific cleavage sequence, it is highly probable that cleavage will only occur at the desired site and not at other sites within the protein.

The cleavage techniques discussed here are by way of example and are but representative of the many variants which will occur to the skilled artisan in light of the specification.

In some instances it may prove desirable to effect cleavage of the proRIP within the cell. For example, an expression vehicle with an appropriate promoter may be provided with a DNA sequence coding for enzymes which convert the proRIP to the active form, operating in tandem with the other DNA sequence coding expression of the proRIP.

Further, as is well known, protein sequences may be modified by post-translation processing such as by becoming associated with other molecules, for example, glycosides, lipids, or such inorganic ions as phosphate. The ionization status will also vary depending on the pH of the medium or the pH at which crystallization or precipitation of the isolated form occurs. Further, the presence of air may cause oxidation of labile groups, such as —SH. Thus, included within the definition of the proRIP and αβ RIP, and fragments, thereof are all such modifications of a particular primary structure, e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

By appropriate choice of restriction sites, the desired DNA fragment may be positioned in a biologically functional vector which may contain appropriate control sequences not present in the selected DNA fragment. By "biologically functional" is meant that the vector provides for replication and/or expression in an appropriate host, either by maintenance as an extrachromosomal element or by integration into the host genome. A large number of vectors are available or can be readily prepared, and are well known to skilled artisans.

In general, vectors containing the appropriate promoters, which can be used by the host organism for expression of its own protein, also contain control sequences, ribosome binding sites, and transcription termination sites. Generally, the replicon and control sequences which are derived from species compatible with the host cell are used in connection with these hosts. Finally, the vectors should desirably have a marker gene that is capable of providing a phenotypical property which allows for identification of host cells containing the vector.

When expressing the αβ RIP, the DNA fragments encoding the α fragment and the β fragment may be inserted into separate vectors, or into the same vector. Specifically, when the α and β fragments are contained in separate vectors, the host cells may be transformed via either cotransformation or targeted transformation techniques.

Construction of suitable vectors containing the desired coding and control sequences may be produced by using well-known techniques (see Sambrook et al. (1989), supra). Thereafter, the vector constructions may be used in transforming an appropriate host cell. Suitable host cells include cells derived from unicellular as well as multicellular organisms which are capable of being grown in cultures or by fermentation.

Various unicellular microorganisms can be used for both cloning and expression. Prokaryotes include members of the Enterobacteriaceae, such as strains of *Escherichia coli*, and Salmonella; Bacillaceae, such as *Bacillus subtilis*; Pneumococcus, Streptococcus, and *Haemophilus influenzae*.

In addition to prokaryotes, eukaryotic cells may be employed. As previously stated, eukaryotic cells have not heretofore been used as recombinant host cells for RIPs. By providing inactive forms of RIPs, the present invention provides skilled artisans with the flexibility to use eukaryotic cells as recombinant hosts. By transforming eukaryotic cells with the proRIP gene, the protein may be expressed at high levels without being toxic to the host cell. Since the protein is lacking in bioactivity pending extra-cellular cleavage, the effect of expressing a proRIP to enhance the biosafety of the procedure. The proRIP may then be selectively chemically or enzymatically converted to the desired αβ RIP.

Exemplary eukaryotic microbes include yeast. *Saccharomyces crevisae*, or common baker's yeast, is the most commonly used among eukaryotic microorganisms, although a number of other hosts are commonly available.

In addition to eukaryotic microbes, cultures of cells derived from multicellular organisms may also be used as hosts. Examples of useful host mammalian cell lines are Sp2/O, VERO and HeLa cells, Chinese hamster ovary (CHO) cell lines, and W138, BHK, COS-7 and MDCK cell lines. Other suitable hosts and expression systems are the baculovirus systems maintained in cultured insect cells, e.g., from *Spodoptera frugiperda*.

Finally, cells from and portions of higher plants have been found useful as recombinant hosts, and appropriate control sequences are available for expression in these systems. Suitable plant cells include cells derived from, or seedlings of, tobacco, petunia, tomato, potato, rice, maize and the like.

The expression vehicle may be inserted into the host cell by any suitable method. Conventional technologies for introducing biological material into living cells include electroporation (see Shigekawa and Dower (1988), *Biotechniques*, 6:742; Miller, et al. (1988), *Proc. Natl. Acad. Sci. USA*, 85:856–860; and Powell, (1988), *Appl. Environ. Microbiol.*, 54:655–660); direct DNA uptake mechanisms (see Mandel and Higa (1972), *J. Mol. Biol.*, 53:159–162; Dityatkin, et al. (1972), *Biochimica et Biophysica Acta*, 281:319–323; Wigler, et al. (1979), *Cell*, 16:77; and Uchimiya, et al. (1982), In: *Proc. 5th Intl. Cong. Plant Tissue and Cell Culture*, A. Fujiwara (ed.), Jap. Assoc. for Plant Tissue Culture, Tokyo, pp. 507–508); fusion mechanisms (see Uchidaz, et al. (1980), in:*Introduction of Macromolecules Into Viable Mammalian Cells*, Baserga et at. (eds.) Wistar Symposium Series, 1:169–185); infectious agents (see Fraley, et al. (1986), *CRC Crit. Rev. Plant Sci.*, 4:1–46; and Anderson (1984), *Science*, 226:401–409); microinjection mechanisms (see Crossway, et al. (1986), *Mol. Gen. Genet.*, 202:179–185); and high velocity projectile mechanisms (see EPO 0 405 696 to Miller, Schuchardt, Skokut and Gould, (DowElanco). The appropriate procedure may be chosen in accordance with the plant species used.

Generally after transformation, the host cells may be grown for about 48 hours to allow for expression of marker genes. The cells are then placed in selective medium and/or screenable media, where untransformed cells are distinguished from transformed cells, either by death or a biochemical property. The transformed cells are grown under conditions appropriate to the production of the desired protein, and assayed for expression thereof. Exemplary assay techniques include enzyme-linked immunosorbent assay, radioimmunoassay, or fluorescence-activated cell sorter analysis, immunohistochemistry and the like. Selected positive cultures are subcloned in order to isolate pure transformed colonies. A suitable technique for obtaining subclones is via the limiting dilution method.

Uses

Essentially all of the uses that the prior art has envisioned for RIPs are intended for the novel αβ RIP and proRIP set forth herein (see *Immunotoxins* (1988), supra; and U.S. Pat. No. 4,869,903 to Lifson et al. (Genelabs Incorporated and the Regents of the University of California)).

By providing inactive precursor forms of the αβ RIP, it is now possible to provide protein synthesis inhibitors with uses in practical and improved ways not before possible. The inactive form of the αβ RIP offers the additional advantage, over active RIPs, of not being active until removal of the linker sequence. Although the RIP is not toxic to the majority of mammalian cells it is known that RIP may be made specifically eytotoxie by attachment to a targeting vehicle which is capable of binding to and into target cells.

Exemplary targeting vehicles include any peptide hormone, growth factor, or other polypeptide cell recognition protein for which a specific receptor exists. A few examples include: antibodies and antibody fragments, lectins, insulin, glucagon, endorphins, growth hormone, melanocyte-stimulating hormone, transferrin, bombesin, low density lipoprotein, luteinizing hormone and asialoglycoprotein that bind selectively to target cells (see *Immunotoxins (*1988), supra). It is well established that conjugates which contain RIP exhibit maximal cytotoxicity only when the RIP moiety is released from the targeting vehicle.

Since the αβ RIP and proRIP do not contain a reactive sulfhydryl group, it may be necessary to modify the proteins using chemical crosslinking reagents in order to link such proRIP and αβ RIP to targeting vehicles.

Conjugates of a monoclonal antibody and the αβ RIP and proRIP may be made using a variety of bifunctional protein coupling agents. General examples of such reagents are N-succinimidyl-3-(2-pyridyldithio)-propionate, 2-iminothiolane, bifunctional derivatives of imidoesters such as dimethyl adipimidate, active esters such as disuccinimidyl suberate, aldehydes such as glutaraldehyde, bis-azido compounds such as bis(p-diazoniumbenzoyl) ethylenediamine, diisocyanates such as toluene 2,6-diisocyanate, and bis-active fluorine compounds such as 1,5-difluoro-2,4-dinitrobenzene (see, for example, WO 86/05098). In addition, recombinant DNA methodologies may be employed to construct a cytotoxic fusion protein. For a general discussion of chimeric toxins (see, for example, Pastan and FitzGerald (1989), *The Journal of Biological Chemistry,* 264:15157–15160; and U.S. Pat. No. 4,892,827 to Pastan et al. (The United States of America as represented by the Department of Health and Human Services)).

EXAMPLES

The present invention is illustrated in further detail by the following examples. The examples are for the purposes of illustration only, and are not to be construed as limiting the scope of the present invention. All temperatures not otherwise indicated are Centigrade. All parts and percentages are by weight unless otherwise specifically noted. All DNA sequences are given in the conventional 5' to 3' direction. All amino acid sequences are given in conventional amino-terminus to carboxy-terminus direction.

Example 1

Isolation of Maize αβ RIP

All steps were performed at 4° C., except for high performance liquid chromatography (HPLC) which was performed at room temperature. Five hundred grams (500 g) of finely ground mature maize kernels were extracted for at least 2 hours and up to 24 hours (hr) with 1500 ml, 25 mM sodium phosphate, pH 7.2 (PB) +50 mM sodium chloride. After the extract was strained through several layers of cheesecloth, the protein precipitating between 55 percent and 85 percent ammonium sulfate was collected and redissolved in PB, then dialyzed overnight against the same buffer. The solution was clarified by centrifugation and applied to a 2.5×10 centimeter (cm) DE-52 cellulose column equilibrated with PB. The protein passing straight through the column was collected and applied to a Mono S 10/10 column (Pharmacia LKB Biotechnology, Piscataway, N.J.) equilibrated with PB, and eluted with a linear gradient of 0 to 200 mM sodium chloride in PB over 90 minutes at 2 milliliter/minute (ml/min). Alternatively, the protein can be precipitated with 85 percent ammonium sulfate and be dialyzed overnight before applying to the Mono S 10/10 column.

Fractions containing ribosome inactivating protein activity (as measured by rabbit reticulocyte protein synthesis assay, described below) were pooled and concentrated to 0.5 ml in Centricon-10 devices (Amicon, Danvers, Mass.), and applied to a Superose 12 column equilibrated in PB (Pharmacia LKB Biotechnology) at a flow-rate of 0.4 ml/min. Fractions containing ribosome inactivating protein activity (as measured by a rabbit reticulocyte protein synthesis assay, described below) (the first major peak) were pooled. At this stage, the αβ RIP was usually quite pure as identified by SDS-PAGE (see Laemmli (1970), supra). If necessary, further purification can be achieved by applying the protein to a Mono S 5/5 column (Pharmacia LKB Biotechnology) equilibrated with PB and eluted at 1 ml/min with 0 to 50 mM sodium chloride in PB over 5 minutes, then 50 to 200 mM sodium chloride in PB over 25 min.

Figure 6:
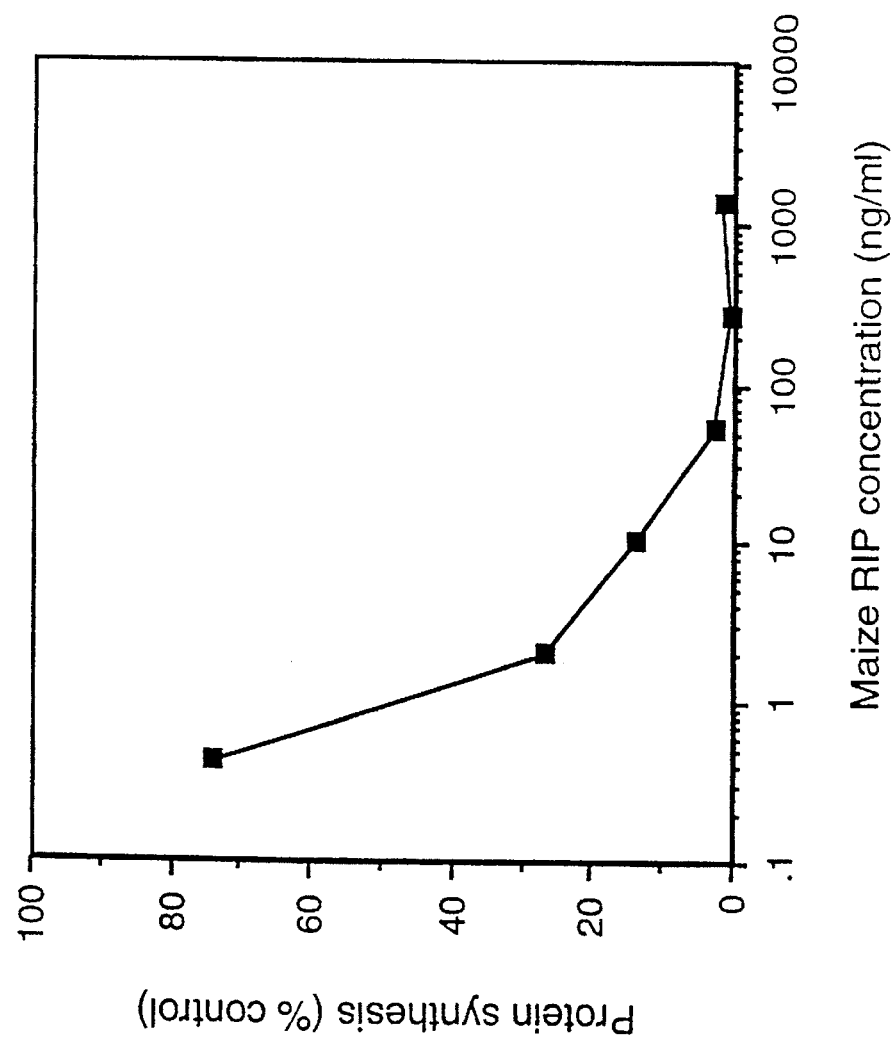
FIG. 6 shows an effect of active maize αβ RIP on mammalian cell-free protein synthesis.

Results from a typical purification are presented in Table 1. The effect of purified maize αβ RIP on mammalian protein synthesis is shown in FIG. 6.

TABLE 1

Purification of maize RIP from Mature Kernels

| Step | Protein (mg) | Total units* × 10$^6$ | Yield (%) | Fold Purification | IC$_{50}$ (ng/ml) |
|---|---|---|---|---|---|
| Crude extract | 6816 | 384 | 100 | 1.0 | 323 |
| 85% Ammonium sulfate | 1010 | 115 | 30 | 2.0 | 161 |
| post-DE52 treatment | 428 | 144 | 38 | 5.9 | 54 |
| Mono S10/10 pool | 10.2 | 58 | 15 | 102 | 3.2 |
| Superose 12 pool | 1.8 | 33 | 8.6 | 327 | 0.99 |
| Mono S 5/5 pool | 1.32 | 32.4 | 8.4 | 436 | 0.74 |

*One unit of activity is the amount of protein required to produce 50% inhibition in the rabbit reticulocyte lysate protein synthesis assay.

A. Rabbit Reticulocyte Cell-Free Protein Synthesis Assay

The inhibitory activity of the maize αβ RIP toward mammalian protein synthesis was measured in a rabbit reticulocyte lysate system following the procedures of Pelham and Jackson (see (1976), Eur. J. Biochem., 67:247–256).

A mix of the following reagents was prepared (2.5 milliliter (ml) total volume): 125 microliter (µl) 200 mM Tris-HCl, pH 7.6+40 mM magnesium acetate +1.6M potassium chloride; 12.5 µl 3 mM hemin hydrochloride in 50 percent ethylene glycol; 1.0 ml untreated rabbit reticulocyte lysate (Promega, Madison, Wis.); 1.0 ml H$_2$O; 62.5 µl amino acid mix; 125 µl 20 mM ATP +4 mM GTP; 125 µl 200 mM creatine phosphate; 50 µl 2.5 mg/ml creatine phosphokinase in 50 percent ethylene glycol. The amino acid mix contained 50 µM of each amino acid except glycine (100 µM), arginine, isoleucine, methionine and tryptophan (10 µM each) and contained no leucine. All stock solutions were previously adjusted to pH 7.5 prior to addition.

Five microliters (5 µl) of appropriate dilutions of samples to be assayed were placed in the wells of a 96-well plate and 50 µl of the mix added. After 10 minutes, 50 nanoCuries (nCi) $^{14}$C-leucine in 10 µl was added to each well. After a further 10 minutes, the reaction was quenched with 10 µl 1.5M potassium hydroxide and incubated for 45 minutes. Twenty-five microliters (25 µl) of each sample was then pipetted onto individual 2.1 cm Whatman 3 MM paper disks (Whatman, Clifton, N.J.) and after drying for 2 to 3 minutes, the disks were washed successively by swirling in a flask with 250 ml 10 percent trichloroacetic acid, 250 ml 5 percent trichloroacetic acid (twice), 125 ml ethanol, 250 ml 1:1 ethanol/acetone, and 125 ml acetone. After drying, the filters were placed into vials with 10 ml scintillation cocktail and counted.

B. Antisera and Western Blot Analysis:

The α and β polypeptide bands were cut from 3 millimeter (mm) SDS-PAGE gels after brief staining with Coomassie blue and were electroeluted using an electroelution device (Bio-Rad, Richmond Calif.) according to the manufacturer's directions. The polypeptide preparations were then used to immunize rabbits to yield polyclonal anti-sera (prepared by RIBI Immunochem, Mont.).

Western blots from Phastgels™ reagent (Pharmacia LKB Biotechnology) were performed by removing the gel from the plastic backing and then electroblotting onto Immobilon paper (Millipore Corporation, Bedford, Mass.). Blots were developed using the maize αβ RIP primary antiserum at 1:2000 dilution and alkaline phosphatase-conjugated goat anti-rabbit secondary antibody (Bio-Rad), according to the manufacturer's instructions.

Example 2

Isolation of Maize proRIP

The polyclonal antisera against the α and β fragments were used to identify a common 34 kD precursor polypeptide in crude extracts of maize kernels (maize proRIP). The presence of the maize proRIP was monitored during subsequent purification by Western blot analysis as set forth above. All steps of the purification were performed at 4° C., except for HPLC which was performed at room temperature.

Two hundred fifty grams (250 g) of immature maize kernels were homogenized in 600 ml 25 mM sodium phosphate, pH 7.2 (PB) +5 µg/ml antipapain. After the extract was strained through several layers of cheesecloth, the protein precipitating between 45 and 80 percent ammonium sulfate was collected and redissolved in 15 ml PB, then passed over a 2.5×15 cm Sephadex G-25 column (Pharmacia LKB Biotechnology) equilibrated in PB. Fractions containing protein were pooled and diluted to ~60 ml with water. The solution was applied to a Q-Sepharose (fast-flow) column packed in a 10/10 FPLC column (Pharmacia LKB Biotechnology) equilibrated with PB, and eluted with a 0 to 300 mM NaCl gradient at 2 ml/min over 75 minutes. Fractions containing the 34 kD precursor were pooled and concentrated by a Centriprep 10 device (Amicon) to 1.5 ml. This was diluted four-fold with water and applied to a Mono Q 5/5 column (Pharmacia LKB Biotechnology) equilibrated in PB. The column was eluted with a 0 to 250 mM NaCl gradient over 60 minutes. Fractions containing the 34 kD polypeptide were pooled, concentrated to 0.5 ml and applied to a Superose 12 column (Pharmacia LKB Biotechnology) equilibrated in PB. The major peak from this column contained the 34 kD maize RIP precursor and appropriate fractions were pooled and stored at –20° C.

Example 3

PAGE Analysis of Maize αβ RIP and proRIP

SDS-PAGE was performed with a Phastsystem™ reagent (Pharmacia LKB Biotechnology) using 20 percent Phastgels™ reagent and following the manufacturer's instructions. Native PAGE was performed at pH 4.2 as described in the Phastsystem™ reagent application file no. 300, method 1 (Pharmacia LKB Biotechnology).

SDS-PAGE of highly purified, active maize αβ RIP exhibited two polypeptides: an α fragment (16.5 kD) and a β fragment (11.0 kD) under both reducing and non-reducing conditions. A single band was seen in native PAGE analysis of purified, active maize αβ RIP. The minimal Mr value of the associated, native maize αβ RIP was therefore 27.5 kD.

By SDS-PAGE, highly purified maize proRIP migrated with a value of 34 kD.

Example 4

In vitro Activation of Maize proRIP by Papain

A purified sample of proRIP was incubated at 0.5 mg/ml with papain, a plant thiol protease, at 0.01 mg/ml in sodium acetate buffer, pH 6 containing 2 mM dithiothreitol. After 1 to 2 hours at room temperature, the 34 kD proRIP was digested to a stable product exhibiting a polypeptide pattern almost identical to that of native, active maize αβ RIP. There was a concomitant increase in ribosome inactivating activity in the incubation; the undigested proRIP had no ribosome inactivating activity up to 2 μg/ml, whereas papain-treated proRIP had an $IC_{50}$ of <80 ng/ml. in contrast trypsin had no effect on maize proRIP.

Example 5

Chemically-Determined Amino Acid Sequences

A. N-Terminal Amino Acid Sequences of Maize αβ RIP α Fragment and β Fragment.

A sample of maize αβ RIP was electrophoresced by the method of Laemmli (1970), supra) in 1.5 mm thick gels and the gel electroblotted onto immobilon PVDF paper (Millipore) using a Transphor™ apparatus (Pharmacia LKB Biotechnology). The paper was stained briefly with Coomassie blue and the bands corresponding to the α and β kD polypeptides were cut out. These were N-terminal sequenced directly from the PVDF paper using a 470A gas phase sequencer (Applied Biosystems, Foster City, Calif.). The following data was obtained (bracketed residues denote lower confidence assignments):

N-Terminal sequence of a fragment (residues 17 to 48 of FIG. 1):
K R I V P K I T E I F P V E D A N Y P V S A F I A[G] V X K D V I An additional minor species (−20 percent of the total species) had the following N-Terminal sequence (residues 13 to 22 of FIG. 1) of:
A Q T N K [L] I V P K N-Terminal sequence (residues 187 to 215 of FIG. 1) of β fragment:
A A D P Q A D T K S X L V K L V V M V S/C E G L X F N T V S B. α fragment C-Terminal Amino Acid Sequence The carboxy-terminal amino acid sequence of the α maize αβ RIP α fragment was determined using sequencing grade carboxypeptidase P from *Penicillium japonicum* (Boehringer Mannheim, Indianapolis, Ind.). A sample of α fragment was purified by reverse-phase HPLC using a Vydac 5μ C4 4.6×30 mm RP column. The column was equilibrated with 0.1 percent trifluoroacetic acid (TFA), and eluted with 0 to 40 percent of 0.1 percent TFA+80 percent acetonitrile over 8 minutes, then 40 to 60 percent of 0.1 percent TFA +80 percent acetonitrile over 20 minutes. The β fragment eluted after 21.9 minutes and the α fragment eluted after 23.3 minutes.

A lyophilized sample of the α fragment was dissolved in 20 mM sodium acetate, pH 5.8+4M urea. The digestion mix contained the following in 0.1 ml: 1.6 μg carboxypeptidase P, 66 μg β fragment, 0.12M sodium acetate pH 4.2, 0.8M urea. After 1, 5, 15, 60, 120 and 480 minutes, duplicate 8 μl aliquots from the digestion were added to 8 μl 0.4M sodium borate, pH 10.5 and frozen on dry ice.

Amino acid analysis was performed essentially as described by Jones (1986), In: *Methods of Protein Microcharacterization* (ed.) J. E. Shively. The following sequence is obtained: $NH_2$-Asp-Leu-Ala-(Lys)n-COOH, where n=2–4. This was the carboxy terminus of the α polypeptide, therefore this and the N-terminus sequence of the β fragment define the linker region contained in the precursor (see amino acid sequence of the recombinant maize proRIP derived from cDNA in FIG. 1).

C. N-Terminal Amino Acid Sequence of Maize proRiP

No N-Terminal sequence data was obtained from a sample of the 34 kD maize proRIP indicating that this polypeptide is N-terminal blocked.

Example 6

Isolation and Characterization of cDNA for Maize proRIP

A. Isolation

Immature kernels from field grown Pioneer hybrid 3737 were harvested, shelled from the cob, and stored at −20° C. Ten grams (10 g) of kernels were frozen in liquid nitrogen for several minutes then ground to a powder in a Waring blender. The powder was suspended in 20 ml of ice cold TENS buffer (10 mM Tris pH 7.4, 1 mM EDTA, 0.5 percent SDS, 0.3M NaCl) and extracted immediately with an equal volume of phenolchloroform-isoamyl alcohol (25:24:1) saturated with TENS buffer. The aqueous phase was collected and extracted three more times with fresh phenol mixtures.

Nucleic acids were precipitated from the aqueous phase by adjusting it to 0.3M sodium acetate pH 5.5 and adding 2.5 volumes of 100 percent ethanol. Nueleic acids were collected by centrifugation and suspended directly in 1 ml phenol-ehloroform-isoamyl alcohol plus 1 ml TENS and extracted by vortexing. The nucleic acid was precipitated from the aqueous phase by ethanol precipitation as above. The precipitate was collected by centrifugation and resuspended in TE buffer (10 mM Tris pH 7.4, 1 mM EDTA). Single strand nucleic acid was precipitated by adjusting the solution to 2M LiCl and incubating for 4 to 12 hours at 4° C. Centrifugation yielded a pellet which consisted of between 2.2 to 2.5 mg of total RNA.

Poly(A)-containing RNA was enriched from the total RNA sample by using Hybond mAP™ mRNA purification affinity paper (Amersham Corporation, Arlington Heights Ill.). The supplier's protocol was followed. Typically 5 to 10 μg of poly(A) enriched RNA were recovered per milligram of total RNA.

Five micrograms (5 μg) of poly(A) enriched RNA were converted into double stranded cDNA using a cDNA Synthesis™ kit (Pharmacia LKB Biotechnology). The cDNA was ligated into the cloning vector Lambda gt11 (Stratagene Inc., La Jolla Calif.) following the supplier's instructions. Packaging of the ligated vector-insert mixture was done with the Gigapack plus packaging extract (Stratagene, Inc.) again following the supplier's protocol.

The PicoBlue Immunodetection™ kit (Stratagene, Inc.) was used to screen the Lambda gt11 maize kernel cDNA library using rabbit polyclonal antisera raised against the maize proRIP, as described above.

Positive clones were purified to homogeneity and the cDNA inserts characterized by Eco RI restriction enzyme analysis. One of the largest Eco RI-generated cDNA inserts (about 1,100 bp) was ligated into the Eco RI site of plasmid pUC19 (Bethesda Research Labs, Gaithersberg, Md.). Clones carrying the proRIP cDNA insert in both orientations were identified by restriction digestion and used for large scale plasmid purification.

B. Sequencing the Maize proRIP cDNA

The nucleotide sequence of the proRIP cDNA (set forth in FIG. 1) was determined by dideoxy chain termination sequencing using the Sequenase™ DNA sequencing kit (United States Biochemical Corp., Cleveland Ohio). The double stranded pUC19-RIP was used as template following the manufacturer's instructions. The first round of sequencing was initiated by the M13/pUC forward sequencing primer (Bethesda Research Labs). Subsequent primers were derived from the sequenced maize proRIP cDNA. Both strands of the cDNA were fully sequenced at least once.

The open reading frame encoding the αβ RIP protein was confirmed by comparing the cDNA deduced amino acid sequence (set forth in FIG. 1) to the chemically determined protein sequence data.

Example 7

Determination of C-terminal Processing of Maize proRIP

Attempts at chemically determining the C-terminal sequence if the β fragment gave equivocal results, as only the only residue that could be firmly identified was alanine. However, alanine accounts for 25% of the 60 C-terminal residues of pro-RIP. The extent of C-terminal proteolytic processing of maize pro-RIP to generate αβ RIP was therefore determined by accurately establishing the molecular weight of the β fragment by electronspray mass spectrometry (ES/MS). Samples of pure β fragment were prepared by reverse-phase HPLC as described in Example 5 from three different preparations of purified αβ RIP prepared as described in Example 1. These were then subjected to ES/MS analysis at the Harvard Microchemical Facility. A value of 11,020 (±20) for the molecular mass of the β fragment was obtained. Using this accurate value, in combinations with the previously-determined N-terminal sequence of the β fragment (Example 5) and deduced amino acid sequence of the pro-RIP (Example 6), the C-terminus of the naturally-occurring β fragment was established as Ala-287. Thus, 14 residues (1,336 Daltons, residues 288–301) are removed from the C-terminus of maize proRIP during processing to generate active αβ RIP.

Example 8

Expression of Maize proRIP and Derivatives in *Escherichia coil*

Various genetic derivatives of maize proRIP may be expressed in *E. coli* and tested for ribosome inactiveting activity. A summary of several constructions and their properties is given below.

A. R34 (the amino acid and nucleotide sequences of which are set forth in FIG. 7) represents the recombinant proRIP gene engineered for expression in *Escherichia coli* which encodes a protein of Mr 33,327 and as expected is not a potent inhibitor of protein synthesis. Upon papain or subtilisin Carlsberg treatment it is processed into two associated polypeptides (of approximately 17+12 kD) by SDS Phastgel™ analysis with very potent ribosome inactivating activity. N34 (not shown) represents the native proRIP as isolated from nature.

B. R30 (the amino acid and nucleotide sequences of which are set forth in FIG. 8). R30 represents the proRIP with no N-terminal leader and no linker.

Expression of the recombinant maize proRIP in *E. coli* was accomplished by engineering the cDNA via PCR amplification. A 5' primer was synthesized which contained termination codons in all three reading frames to stop translation of vector-encoded proteins upstream of the maize proRIP cDNA. The primer also contained a Shine-Dalgarno sequence several base pairs upstream of an ATG start codon followed by 23 bases which were homologous to the maize proRIP cDNA. The 3' primer spans the 3' cDNA end-pUC19 junction (the primers were shown by the underlined regions set forth in FIG. 1). PCR amplification of the cDNA in pUC19 using the GeneAmp™ kit (Perkin Elmer-Cetus, Norwalk, Conn.) yielded a predominant amplification product of approximately 1100 base pairs, as expected.

The engineered, amplified product, was purified from an agarose gel and ligated into the filled-in Hind III site of the expression vector pGEMEX-1 (Promega Corp., Madison, Wis.) to give plasmid pGR, set forth in FIG. *9a*.

This was transformed into *E. coli* DH5a (Bethesda Research Labs). Plasmids containing the maize proRIP cDNA were isolated by colony hybridization (see Sambrook et al., supra) with a 5' maize proRIP cDNA probe and characterized. Those containing the cDNA probe for the maize proRIP in the correct orientation were tested for expression. Plasmids were transformed into competent *E. coli* JM109(DE3) (Promega Corp., Madison, Wis.), transformed cells were grown in 15 ml cultures under ampicillin selection to an optical density at 600 nm of 0.4 to 1.0. Isopropylthio-β-galactoside (IPTG) was added to 1.3 mM to induce the production of recombinant proRIP and the cultures were grown an additional 4 hours at 37° C. The cells were collected by centrifugation and stored as a pellet at −20° C.

The protein produced from the maize proRIP cDNA was analyzed by iysing the induced cells in TE containing 1 mg/ml lysozyme 37° C. for 15 minutes. The lysate was fractionated into a crude supernatant and pellet by microcentrifugation. The fractions were analyzed by SDS-PAGE using 20 percent Phastgels™ reagent (Pharmacia LKB Biotechnology). Coomassie blue staining and Western blot analysis of the gels with anti-maize proRIP sera identified a 34 kD band which was greatly increased upon induction of the cells with IPTG. Cells not carrying the plasmid or containing the plasmid with the maize proRIP cDNA in the inverted orientation did not contain this 34 kD immunoreactive band. The majority of the recombinant maize proRIP was contained in the cellular pellet suggesting the material was insoluble under these conditions.

To test if R34 could acquire the folding pattern of N34 the pellet fraction of an induced culture was dissolved in 6M guanidine HCl and allowed to denature at room temperature for 3 hours. The material was then diluted 200-fold into ice cold TE and incubated at 4° C. overnight to allow refolding of the denatured R34. The diluted material was then concentrated by a Centricon 10 device (Amicon). To test whether refolded R34 could undergo the correct proteolytic processing to the fragmented form of the maize proRIP, the material was treated with 10 μg/ml papain for various times, and samples were analyzed by SDS-Phastgel and Western blot analysis. The R34 material was processed to a stable mixture of two immuno-reactive bands which comigrate with N34 papain-processed material indicating the correct proteolytic processing had occurred.

Figure 9A:
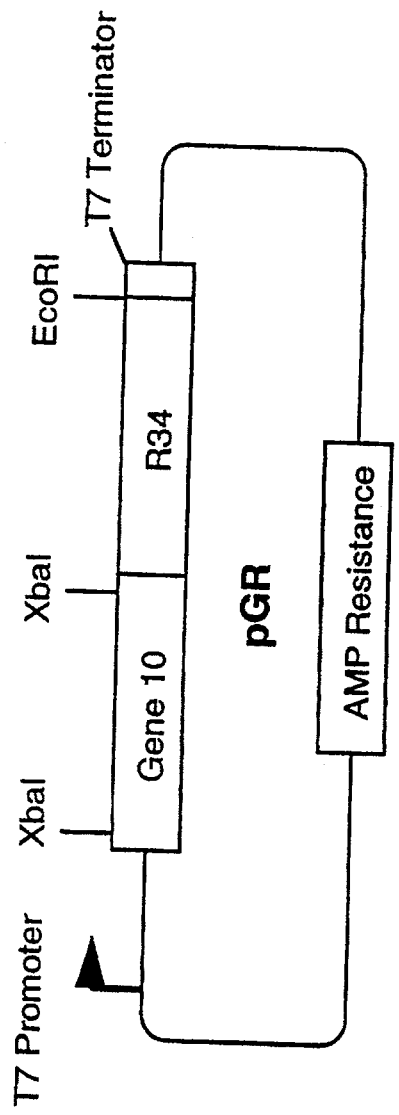
FIG. 9*a* shows a plasmid map of plasmid pGR and FIG. 9*b* shows a plasmid map of plasmid pGR1.
Figure 9B:
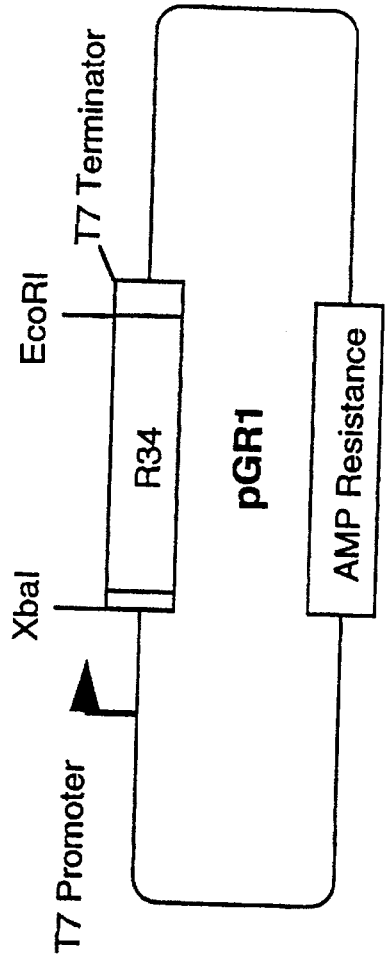

In an effort to simplify purification of the R34 polypeptide from induced lysates, the gene 10 coding region of the pGEMEX-1 vector was removed by cutting the maize proRIP gene-containing plasmid (pGR) with Xba I and gel purifying the vector/proRIP DNA away from the gene 10 encoding DNA. Recircularization of pGR, now minus the gene 10 coding region, resulted in a plasmid called pGR1 set forth in FIG. 9b.

The plasmid pGR1 was transformed into JM109(DE3) cells and tested for production of R34 following induction with IPTG. As with pGR, large amounts of R34 were identified in cellular lysates both by Western blot and Coomassie blue staining. Unlike pGR, R34 produced from pGR1 was soluble and fractionated in the supernatant of lysed cells. This soluble material was treated with papain at 10 µg/ml and the RB34 produced from pGR1 was cleaved to products which comigrate with N34, papain-cleaved product. The papain-treated material inhibited translation of reticulocyte lysates at significantly higher dilutions than the untreated material, indicating that the soluble R34 was processed to an active form.

C. R34-DL represents the proRIP without the linker (the amino acid and nucleotide sequences of which are set forth in FIG. 10. The sequences encoding α and β were joined directly without intervening linker DNA, i.e., nucleotides A-520 to A-594, inclusive of the intact recombinant maize proRIP nucleotide sequence (see FIG. 1) are deleted. The R34-DL gene encoded a 30.6 kD protein which was a potent inhibitor of protein synthesis. Treatment of R34-DL with papain resulted in a 28 kD polypeptide with increased ribosome inactivating activity over the untreated molecule.

Confirmation that removal of the linker from maize proRIP activated the molecule was obtained independently through genetic engineering. The 75 bp linker encoding region of R34 (A-520 to A-594 inclusive) was deleted using PCR amplification. The new construction R34-DL joined directly, in frame, the DNA encoding both the α and β fragments.

In the pGEMEX-1 system the R34-DL gene directed the synthesis of a polypeptide approximately 30.6 kD, which was recognized by antisera specific for the maize proRIP. At high dilution, *coli* lysates containing R34-DL protein were potent inhibitors of protein synthesis in rabbit reticulocyte lysates, in marked contrast to *E. coli* lysates containing the R34 polypeptide.

These genetic deletion data confirm that removal of the linker served to activate the R34 (proRIP) molecule. This experiment also demonstrated that covalent linkage of the α and the β polypeptide fragments resulted in an active αβ RIP. The maize proRIP did not require a break in the polypeptide backbone for enzymatic activity, removal of the linker region was sufficient to confer potent ribosome inactivating activity.

In addition, when R34-DL lysates were treated with papain a slight decrease in the molecular weight of R34-DL protein is noted (from 30.6 kD to approximately 28 kD). The R34-DL polypeptide remained intact, that is, it was not cleaved to the characteristic maize αβ RIP α and β fragments. Associated with this small change in molecular weight was an increase in protein synthesis inhibition in the *E. coli* lysates. These data indicated that in bacterial lysates removal of the linker region activated the ribosomal inactivating activity of the protein at least 250-fold, but that additional processing from the ends of the protein increased the activity.

D. Another genetic construction was made using PCR technology to remove the leader region from R34-DL. The new construction called R30-DL (nucleotides C-40 to C-84 and A-520 to A-594), inclusive, of the intact recombinant maize proRIP nucleotide sequence are deleted) encoded a protein (approximately 29.5 kD) which was slightly smaller than R34-DL (the amino acid sequence and the nucleotide sequence of which are set forth in FIG. 11). *E. coli* lysates containing R30-DL appeared to be even more potent inhibitors of protein synthesis than R34-DL lysates. Papain treatment of R30-DL containing lysates further enhanced protein synthesis inhibiting activity. Following this treatment the R30-DL protein underwent a slight decrease in molecular weight representing processing at the ends of the polypeptide.

Example 9

Expression of a Fully-Activated Maize RIP Derivative

A segment of the R30-DL gene was deleted which encodes several acidic residues at the carboxy terminus of the protein. The deletion was accomplished using the PCR engineering methods.

A thermocycler (Perkin-Elmer Cetus, Norwalk, Conn.) was used for the indicated constructions. A typical run was a one minute denaturation step, a 2 minute annealing, and a 3 minute extension step. Temperatures used were 94° C., 37° C. or 50° C., and 72° C. respectively. Following 25 cycles the reaction was held at 72° C. for 7 minutes for extension of unfinished products.

Amplification engineering reactions were done in four separate tubes of 100 μL each. The tubes were combined following amplification. Normally 100 ng of template was included in each tube. DNA primers were synthesized on a PCR Mate or 380A DNA synthesizer (Applied Biosystems) and were purified on acrylamide gels. Fifty pmol of each primer were included in each reaction. The reaction conditions for the amplification were those recommended by Perkin Elmer Cetus (10 mM Tris-HCl pH8.3, 50 mM KCl, 1.5 mM $MgCl_2$, 0.001 percent gelatin, 200 μM dNTPs and 2.5 units of Taq DNA polymerase or AmpliTaq™ thermostable DNA polymerase).

Several methods of genetic engineering were employed to produce the genetic derivatives described below. Standard methods of DNA purification, restriction enzyme digestion, agarose gel analysis, DNA fragment isolation, ligation and transformation were employed (see *Current Protocols in Molecular Biology* (1989), supra and Sambrook et al. (1989), supra).

Enzymes used for the engineering were from one of three manufacturers (Pharmacia LKB Biotechnology; Bethesda Research Labs; or New England Biolabs, Beverly, Mass.). Buffers and protocols used were provided by the manufacturer.

Using PCR, a modified RIP fragment was amplified from an RIP plasmid template, purified, then used to replace the unmodified region in the RIP gene. All fragment replacements were done in RIP genes already inserted into a pGEMEX expression plasmid.

A pGEMEX plasmid containing R30-DL, which had the 3' half of the gene removed by Nco I and Stu I digestion followed by gel purification was used as the template for PCR. The 3' half of the RIP gene was replaced with the PCR modified fragment described below.

A 3' PCR primer was synthesized which encoded the 7 amino acid residue deletion near the carboxy terminus and introduced a new unique Bam HI site. The 5' primer directed the deletion of the αβ linker and included a Nco I site. The sequences of the 5' primer and the 3' primer for the PCR amplification of RDT are given in below.

5' Primer (SEQ. ID. NO. 39):

5'-ACC GTC ACC ATG GGC CGC GCC GAA ATG ACC AGG

GCC GTC AAC GAC CTG GCG AAG AAG AAG AAG GCG

GCT GAC CCA CAG GCC GAC ACG AAG AGC-3'

3' Primer (SEQ. ID. NO. 40):

5'-CGG ATC CAG CAG TAG CGG CAG CGG CAG TAG-3'

The primers were used to amplify a modified DNA fragment from a pGEMEX R34-DL template. The amplified fragment was phenol extracted and ethanol precipitated. The insert DNA was cut with Nco I and ligated into the pGEMEX-R30-DL vector.

The new RIP gene derivative is designated RDT and encodes a protein of predicted a 28,233 Daltons and pI of ~9.5. The RDT gene encodes a protein with a truncated leader, deleted linker and truncated carboxy terminus.

The predicted DNA sequence and deduced amino acid sequence for RDT is shown in FIG. 12.

The RDT gene, expressed in E. coli using the pGEMEX system described above, was purified from bacterial lysates to apparent homogeneity. RDT protein appears to be a more potent inhibitor of protein synthesis than R30-DL. Using the retieulocyte lysate protein synthesis assay, purified RDT has a $IC_{50}$ value of 1 ng/ml.

Example 10

Modification of RDT for Fusion to Other Polypeptides

RDT was further engineered to produce another gene called RDT-NP. This construction differs from RDT in having two unique restriction sites engineered into the gene. The sites were introduced using PCR methods described in Example 9. The PCR primer was designed such that it included the desired change and a unique restriction site in the maize RIP DNA sequence. A 99 bp primer was developed to introduce the Not I and Pst I sites at the 3' end of the primer and had to be built back to the unique Nco I site for cloning purposes. The sequences of the 5' primer and 3' primer for the PCR amplification are shown below 5' Primer (SEQ. ID. NO. 41):

5'-ACC GTC ACC ATG GGC CGC GCC GAA ATG ACC AGG

GCC GTC AAC GAC CTG GCG AAG AAG AAG AAG GCG

GCC GCC GCT GCA GAC CCA CAG GCC GAC ACG AAG-3'

3' Primer (SEQ. ID. NO. 42):

5'-CAT GCC GGC CAG TGA ATT CGG-3'

The restriction sites (Not I and Pst I) correspond to the site of the alpha/beta linker insertion in the RIP polypeptide. RDT-NP allows DNA segments encoding various polypeptide linkers to be inserted into the gene and tested for their ability to create an inactive, yet protease activatable RIP. The predicted DNA sequence and deduced amino acid sequence for RDT-NP is shown in FIG. 13.

The RDT-NP polypeptide had a predicted molecular weight of 28,446 Daltons and pI of 9.5. Crude lysates of E. coli expressing RDT-NP from a pGEMEX vector are potent inhibitors of eukaryotic protein synthesis.

Example 11

Maize RIP Fused to a Protein A Antibody-Binding Domain

To create an RIP molecule which would bind to immunoglobulin IgG, a single Antibody Binding Region (ABR) domain from the Staphyloeoccus aureus antibody binding Protein A was subcloned from the plasmid pRIT5 (Pharmacia LKB Biotechnology) using PCR techniques. The antibody binding domain of protein A (ABR-A) was PCR engineered to have a Bam HI site at its 5' end and a Bgl II site at it's 3' end. This allowed insertion of the ABR-A domain into the RDT Bam HI site while retaining the unique Bam HI site. The predicted DNA sequence and deduced amino acid sequence of RDT-A is shown in FIG. 14.

RDT-A was expressed in E. coli cells using the pGEMEX system. The resulting polypeptide had a predicted molecular weight of 35,198 Daltons and pI of 9.2. it was recognized by antisera to both protein A and maize RIP indicating the chimeric nature of the protein. Crude lysates of bacteria expressing RDT-A had potent eukaryotic protein synthesis inhibition activity.

RDT-A was shown to bind specifically to IgG Sepharose (Pharmacia LKB Biotechnology) following the manufacturer's instructions. Binding was best at pH 7.0. When washed at pH 5.0 the ehimeric protein was released in small but detectable quantities from the resin. RDT alone does not bind to the gel.

Example 12

Maize RIP-fused to Protein A and Protein G Antibody-binding Domain

To increase the binding ability of the RDT-A to IgG antibodies the Antibody Binding Domain from Streptococcal Group G protein G (ABR-G) was synthesized using oligonucleotides. The sequence synthesized was that of the naturally occurring sequence described by Guss et al. ((1986), EMBO Journal, 5:1567–1575). The only change was the addition of Bam HI and Bgl II sites at the 5' and 3' ends respectively of the synthetic DNA.

The ABR-G fragment was inserted into the Bam HI site of RDT-A. Two classes of clones have been studied. RDT-G-A contains a single ABR-G domain inserted in the correct orientation between the 3' end of RDT and the 5' end of ABR-A. A second class contains two properly oriented ABR-G domains. The predicted DNA sequence and deduced amino acid sequence for RDT-G-A are shown in FIG. 15; and the predicted nucleotide sequence and deduced amino acid sequence for RDT-G-G-A are shown in FIG. 16.

When these genes were expressed in *E. coli* using the pGEMEX system the expected chimeric proteins were produced. The RDT-G-A produced a protein of predicted molecular weight 44,576 Daltons (pI 7.2). RDT-G-G-A produced a slightly larger polypeptide predicted to be 53,955 Daltons with a predicted pI of 5.4.

Crude bacterial lysates of cells expressing RDT-G-A or RDT-G-G-A were potent inhibitors or eukaryotic protein synthesis in the rabbit reticulocyte assay described in Example 2. Papain treatment of the lysates further increases activity. Analysis of the papain treated lysates indicates that the intact RDT domain is released from the ABR domains.

Both RDT-G-A and RDT-G-G-A bind tightly to IgG Sepharose (Pharmacia LKB Biotechnology). Binding is stable at pH 5.0 Elution was accomplished with 0.5M ammonium acetate pH 3.5 or by boiling the resin in SDS.

Example 13

Introduction of a Disulfide-Containing, Proteolytically-Sensitive Linker Peptide Between RDT and Antibody-binding Domains The maize RIP (RDT) antibody binding domain (GGA) fusions described above (see Examples 11 and 12) have been shown to have both RIP and antibody binding activity. A third component was added to the constructions which would allow separation of the domains following proteolysis with trypsin and reduction with reducing agents. This was accomplished by inserting a segment of DNA between the RDT and GGA domains which encodes a protein with two cysteine residues. The cysteine residues form a disulfide bond with a 7 amino acid loop. The resulting disulfide bonded loop contains the recognition sequence for the protease trypsin. Completion of this construction required several steps as indicated below.

A. Construction of RDT-BHSR

To simplify the insertion of sequences between the RDT and GGA domains in the gene RDT-GGA, two restriction sites were added. This was done by cutting the plasmid containing RDT-GGA with the enzymes Bam HI and Eco RI. The GGA encoding region was removed from the plasmid and replaced with the synthetic oligonucleotide linker shown below (the top nucleotide sequence is SEQ ID NO: 43 and the bottom nucleotide sequence is SEQ ID NO: 45.

```
Bam HI    Hpa I
  |        |
  GATCCGTTAACGTCGACG

GCAATTGCAGCTGCTTAA
              |        |
             Sal I    EcoR I
```

The linker restores the Bam HI and Eco RI sites while adding Hpa I and Sal I sites. The resulting construction RDT-BHSR (the predicted nucleotide sequence and deduced amino acid sequence is shown in FIG. 17).

B. Construction of RDT-BHSR-GGA

A Sal I site was placed on the end of the GGA domains by PCR amplification of the segment using the primer shown below (SEQ. ID. NO 44):

```
       Sal I
         |
ATATTAGTCGACAAACCAGAAGTGATCGATGCG
``` and a 3' primer which primes downstream of the Eco RI site. Following amplification, the PCR product was cut with Sal I and Eco RI and ligated into the Sal I and Eco RI sites of RDT-BHSR to create a new construction called RDT-BHSR-GGA (the predicted nucleotide sequence and deduced amino acid sequence is shown in FIG. 18).

C. Construction of RDT-DS-GGA

A linker was designed and synthesized which encodes a trypsin cleavage site flanked by two cysteine residues. The cysteine residues were expected to form a disulfide bond under appropriate conditions. The predicted nucleotide and deduced amino acid sequence for the DS linker (the top nucleotide sequence is SEQ ID NO: 57, the bottom nucleotide sequence is SEQ ID NO: 58 and the amino acid sequence is SEQ ID NO: 59) is set forth below:

```
BamH I                                                    Sal I
   |                                                        |
GA TCC TCT TGC GCT CGT GTC CGT CGT TCG AGC TGC GGT G

G AGA ACG CGA GCA CAG GCA GCA AGC TCG ACG CCA CAG CTG

Gly Ser Ser Cys Ala Arg Val Arg Arg Ser Ser Cys Gly Val Asp
```

The gene RDT-BHSR-GGA was cut with Bam HI and Sal I and the synthetic double stranded oligonucleotide as shown below was ligated into the gene to create RDT-DS-GGA (see FIG. 19 for the predicted DNA sequence and deduced amino acid sequence of RDT-BHSR-GGA).

The gene RDT-DS-GGA was expressed in *E. coli* using the T7 expression system and purified on an IgG Sepharose column as described below.

D. Expression in *Escherichia coli* of RDT-DS-GGA Using the T7 System

The expression system used was based on the T7 system as described by Moffat and Studier ("Use of T7 RNA Polymerase to Direct Expression of Cloned Genes", F. W. Studier et al. (1990), *Methods in Enzymoloqy* 185:60–89). The expression strain JM109(DE3) is lysogenic for the T7 RNA polymerase gene under lac promoter control. Typically, JM109(DE3) (Genotype: recA1, endoA1, gyrA96, thi-, hsdR17, supE44, relA1, D(lac, pro), F' traD36 proAB lacIq, lacZ DM15 : DE3, Promega, Madison Wis.) was transformed with the RDT-DS-GGA expression plasmid the night before an expression experiment. The freshly transformed cells were harvested from plates and transferred to Luria Broth (5×10⁷ cells/ml). The culture was shaken vigorously at 37° C. for 30–60 minutes then induced with 1–10 mM IPTG. The cultures were harvested 3 hours following induction by centrifugation. Cell pellets were stored at –20° C.

Cell pellets were subjected to two freeze thaw cycles before being suspended in 1/5 volume lysis buffer (10 mM Tris pH 8.0, 1 mM EDTA, 150 mM NaCl, 0.1% Triton X-100, 1 mg/ml Lysozyme, 100 µg/ml DNase and 100 µg/ml RNase). The cells were allowed to incubate in lysis buffer 15 minutes at 37° C. The extract was fractionated by centrifugation at 4000×G for 10 minutes at room temperature. The supernatant was collected and stored at –20° C. for purification.

E. Purification

A 5 ml column of IgG Sepharose 6FF (Pharmacia, Piscataway N.J.) was prepared as directed by manufacturer's instructions. The column was equiliberated in TST (50 mM Tris pH 7.5, 150 mM NaCl, 0.05% Tween 20).

The lysate was mixed with an equal volume of TST containing protease inhibitors (100 uM antipain and 2 mM PMSF, Sigma Chemical, St Louis, Mo.) and applied to the column. The column was washed with 5–10 volumes TST. Elution of bound material was with 2 column volumes 0.5M NaAcetate pH 3.5. After elution the sample was dialyzed against 4 liters 20 mM Tris pH 8.0, 100 mM NaCl, 2 mM EDTA overnight 4° C. The affinity purified RDT-DS-GGA was concentrated in a Centriprep 30 concentrating unit. SDS Polyacrylamide gel analysis of the purified RDT-DS-GGA protein indicated it was greater than 95% pure. The material ran as a single band at approximately 55 kD.

F. Trypsin Treatment of RDT-DS-GGA

The purified RDT-DS-GGA was treated with sequencing grade trypsin (Boehringer Mannheim, Indianapolis Ind.) at a 1:100 (wt:wt) ratio 35° C. for 2 minutes (50 mM Tris pH 8.0, 2 mM $CaCl_2$). The reaction was stopped by adding a 10× weight excess of soybean trypsin inhibitor (Sigma Chemical, St Louis, Mo.).

G. Characterization of RDT-DS-GGA

Analysis of trypsin treated RDT-DS-GGA was done using 20% Phast Gels (Pharmacia, Piscataway N.J.) with or without reducing agents in the sample buffer. Under oxidizing conditions untreated RDT-DS-GGA migrates at approximately 55 kD whereas trypsin-treated RDT-DS-GGA migrates at approximately 42 kD. We have shown that RDT alone is not cleaved by trypsin under these conditions and therefore conclude that the 42 kD polypeptide is a result of trypsin cleavage within the GGA domains. When analyzed under reducing conditions the 42 kD polypeptide splits into a major band at 28 kD (co-migrating with RDT) and some smaller molecular weight fragments. The 28 kD band is recognized by anti-maize RIP antibodies. These data indicate that the engineered trypsin site between the RDT and GGA domains is clipped by trypsin and the domains are held together via a disulfide bond. These observations were confirmed by testing RDT-BHSR-GGA under the same conditions. When treated with trypsin RDT-BHSR-GGA produces a 42 kD species which is stable under reducing conditions.

Trypsin treated RDT-DS-GGA is quantitatively retained by a IgG-Sepharose column indicating that the trypsin truncated fusion protein binds IgG. When the column is eluted with reducing agent (TST with 10 mM DTT) a single 28 kD band is quantitatively eluted. The band is recognized by maize RIP antibodies and has potent RIP activity.

Example 14

Detection of Maize proRIP and αβ RIP Homologs in PanicodeaeA. Immunological Detection Seeds from the following species of Panicoideae were ground to a fine consistency in a mortar and pestle (after removal of the glume if necessary): Zea mays mays, Z.m. mexicana, Z.m. parviglumis, Z. luxurians, Z. mexicana, Z. mexicana , Tripsacura dactyloides , Coix lachryma-jobi , Sorghum bicolor.

Soluble proteins were extracted from mature dry seed by the following techniques. The proteins were extracted for 2 hours with 50 mM sodium phosphate buffer, pH 7.5 containing 25 µg/ml leupeptin, 25 µg/ml antipain, 2 mM EDTA and 4 mM phenylmethane sulfonyl fluoride. Three milliliter extraction buffer per gram seed tissue was used. After centrifugation to remove insoluble material, an aliquot of the extract was analyzed by sodium dodecyl sulfate-polyacrylamide gel electrophoresis using 17–27% gradient gels, then electroblotted onto PVDF paper (Millipore). The blot was probed using rabbit antisera against maize RIP α and β fragments (1:2000 dilution each) as primary antibody and goat anti-rabbit IgG antibody as secondary antibody, then developed with NBT/BCIP.

Except for the Coix extract, all the extracts tested showed cross-reactivity with the maize RIP antisera. A prominent band at ~34 kD was observed corresponding to proRIP, and bands at ~16.5 and 11.0 kD were also observed, corresponding to α and β fragments respectively. This indicates that RIP forms equivalent to maize proRIP and the activated αβ form are present in many members of the subfamily Panicoideae.

B. Detection by DNA Hybridization

Total DNA from the following species was isolated according to the procedures described by Saghai-Marcoof et al., PNAS, 81:8014–8018, 1984. The following species of Panicoideae were included: 3 accessions of Zea mays ssp. parviglumis; Zea luxurians; Zea mays ssp. mexicana; Coix lachryma-jobi; Sorghum bicolor; and Zea mays ssp. mays var. B73.

Generally, about 8 µg of the extracted DNA from each sample was digested to completion with 20 units of Hind III, Eco RI and Sst I in 20 microliters of a reaction mixture containing the appropriate reaction buffer at 37° C. for 2 hours.

Next, the total extracted DNA from each sample was subjected to the Southern hybridization technique (see Southern (1975), J. Mol. Biol., 98:503–517). The DNA fragments were fractionated on the basis of their size by means of electrophoresis on a 0.8% agarose gel. The double-stranded DNA fragments were modified into single-stranded DNA fragments in an alkali solution; and then a nylon filter was placed into close contact with the gel to transfer the modified DNA segments onto the filter in the presence of a high salt concentration solution.

Hybridization was carried out using, as the probe, the cDNA clone of the RIP gene (the probe fragment is provided from base position 2 to 1075 in FIG. 1). The probe was radiolabeled with $^{32}P$ and the signals in Southern transfers were visualized by autoradiography.

The Southern blots were hybridized with the cDNA clone of the RIP gene. A single fragment with strong homology to the clone was observed for each enzyme/species combination except the Coix accession. The inbred line of maize has a single major band with two minor bands. The other species which, with the exception of Sorghum, are not inbred showed between 2 and 5 minor bands. The Coix had either 4 or 5 such bands depending on the enzyme used.

Although the invention has been described in considerable detail, with reference to certain preferred embodiments thereof, it will be understood that variations and modifications can be affected within the spirit and scope of the invention as described above and as defined in the appended claims.

---

SEQUENCE LISTING ( 1 ) GENERAL INFORMATION:

( i i i ) NUMBER OF SEQUENCES: 81

( 2 ) INFORMATION FOR SEQ ID NO:1:

( i ) SEQUENCE CHARACTERISTICS:
        ( A ) LENGTH: 1076 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 28..933

( x i ) SEQUENCE DESCRIPTION: SEQ ID NO:1:

```
GAATTCGGCA CGAGCAAAGA GAAGGGA ATG GCC GAG ATA ACC CTA GAG CCG              51
                                Met Ala Glu Ile Thr Leu Glu Pro
                                 1               5

AGT GAT CTT ATG GCG CAA ACA AAC AAA AGA ATA GTG CCA AAG TTC ACT            99
Ser Asp Leu Met Ala Gln Thr Asn Lys Arg Ile Val Pro Lys Phe Thr
        10                  15                  20

GAA ATC TTC CCC GTG GAG GAC GCG AAC TAC CCT TAC AGC GCC TTC ATC           147
Glu Ile Phe Pro Val Glu Asp Ala Asn Tyr Pro Tyr Ser Ala Phe Ile
 25              30                  35                          40

GCG TCG GTC CGG AAA GAC GTG ATC AAA CAC TGC ACC GAC CAT AAA GGG           195
Ala Ser Val Arg Lys Asp Val Ile Lys His Cys Thr Asp His Lys Gly
                    45                  50                  55

ATC TTC CAG CCC GTG CTG CCA CCG GAG AAG AAG GTC CCG GAG CTA TGG           243
Ile Phe Gln Pro Val Leu Pro Pro Glu Lys Lys Val Pro Glu Leu Trp
                60                  65                  70

TTC TAC ACA GAG CTC AAA ACT AGG ACC AGC TCC ATC ACG CTC GCC ATA           291
Phe Tyr Thr Glu Leu Lys Thr Arg Thr Ser Ser Ile Thr Leu Ala Ile
            75                  80                  85

CGC ATG GAC AAC CTG TAC CTC GTG GGC TTC AGG ACC CCG GGC GGG GTG           339
Arg Met Asp Asn Leu Tyr Leu Val Gly Phe Arg Thr Pro Gly Gly Val
        90                  95                 100

TGG TGG GAG TTC GGC AAG GAC GGC GAC ACC CAC CTC CTC GGC GAC AAC           387
Trp Trp Glu Phe Gly Lys Asp Gly Asp Thr His Leu Leu Gly Asp Asn
105             110                 115                 120

CCC AGG TGG CTC GGC TTC GGC GGC AGG TAC CAG GAC CTC ATC GGC AAC           435
Pro Arg Trp Leu Gly Phe Gly Gly Arg Tyr Gln Asp Leu Ile Gly Asn
                125                 130                 135

AAG GGT CTG GAG ACC GTC ACC ATG GGC CGC GCC GAA ATG ACC AGG GCC           483
Lys Gly Leu Glu Thr Val Thr Met Gly Arg Ala Glu Met Thr Arg Ala
                140                 145                 150

GTC AAC GAC CTG GCG AAG AAG AAG ATG GCG ACA CTG GAG GAG GAG               531
Val Asn Asp Leu Ala Lys Lys Lys Met Ala Thr Leu Glu Glu Glu
            155                 160                 165

GAG GTG AAG ATG CAG ATG CAG ATG CCG GAG GCC GCT GAT CTG GCG GCG           579
Glu Val Lys Met Gln Met Gln Met Pro Glu Ala Ala Asp Leu Ala Ala
        170                 175                 180

GCG GCA GCG GCT GAC CCA CAG GCC GAC ACG AAG AGC AAG CTG GTG AAG           627
Ala Ala Ala Ala Asp Pro Gln Ala Asp Thr Lys Ser Lys Leu Val Lys
185             190                 195                 200

CTG GTG GTC ATG GTG TGC GAG GGG CTG CGG TTC AAC ACC GTG TCC CGC           675
```

-continued

```
          Leu Val Val Met Val Cys Glu Gly Leu Arg Phe Asn Thr Val Ser Arg
                          205                 210                 215

ACG GTG GAC GCG GGG TTC AAC AGC CAG CAC GGG GTG ACC TTG ACC GTG            723
Thr Val Asp Ala Gly Phe Asn Ser Gln His Gly Val Thr Leu Thr Val
            220                 225                 230

ACG CAG GGG AAG CAG GTG CAG AAG TGG GAC AGG ATC TCC AAG GCG GCC            771
Thr Gln Gly Lys Gln Val Gln Lys Trp Asp Arg Ile Ser Lys Ala Ala
        235                 240                 245

TTC GAG TGG GCT GAC CAC CCC ACC GCT GTG ATC CCC GAC ATG CAG AAG            819
Phe Glu Trp Ala Asp His Pro Thr Ala Val Ile Pro Asp Met Gln Lys
    250                 255                 260

CTT GGC ATC AAG GAT AAG AAC GAA GCA GCG AGG ATC GTT GCG CTC GTT            867
Leu Gly Ile Lys Asp Lys Asn Glu Ala Ala Arg Ile Val Ala Leu Val
265                 270                 275                 280

AAG AAT CAA ACT ACT GCC GCT GCC GCT ACT GCT GCC AGT GCT GAC AAC            915
Lys Asn Gln Thr Thr Ala Ala Ala Ala Thr Ala Ala Ser Ala Asp Asn
                285                 290                 295

GAC GAC GAC GAG GCC TGATCAATGC AACGACACAT CATGATCTGC TGCTGCACTT            970
Asp Asp Asp Glu Ala
                300

AATTACTATG TTCGTATACA AATAAATACA CCCGGCGTAC GCGGTGTTCC TTATATGGTC         1030

TAAAATGTAG CCAGTAAATT TTAAACTACT TTCTCGTGCC GAATTC                        1076
```

( 2 ) INFORMATION FOR SEQ ID NO:2:

( i ) SEQUENCE CHARACTERISTICS:
        ( A ) LENGTH: 301 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Glu Ile Thr Leu Glu Pro Ser Asp Leu Met Ala Gln Thr Asn
  1               5                  10                  15

Lys Arg Ile Val Pro Lys Phe Thr Glu Ile Phe Pro Val Glu Asp Ala
                 20                  25                  30

Asn Tyr Pro Tyr Ser Ala Phe Ile Ala Ser Val Arg Lys Asp Val Ile
             35                  40                  45

Lys His Cys Thr Asp His Lys Gly Ile Phe Gln Pro Val Leu Pro Pro
         50                  55                  60

Glu Lys Lys Val Pro Glu Leu Trp Phe Tyr Thr Glu Leu Lys Thr Arg
 65                  70                  75                  80

Thr Ser Ser Ile Thr Leu Ala Ile Arg Met Asp Asn Leu Tyr Leu Val
                 85                  90                  95

Gly Phe Arg Thr Pro Gly Gly Val Trp Trp Glu Phe Gly Lys Asp Gly
            100                 105                 110

Asp Thr His Leu Leu Gly Asp Asn Pro Arg Trp Leu Gly Phe Gly Gly
        115                 120                 125

Arg Tyr Gln Asp Leu Ile Gly Asn Lys Gly Leu Glu Thr Val Thr Met
    130                 135                 140

Gly Arg Ala Glu Met Thr Arg Ala Val Asn Asp Leu Ala Lys Lys Lys
145                 150                 155                 160

Lys Met Ala Thr Leu Glu Glu Glu Val Lys Met Gln Met Gln Met
                165                 170                 175

Pro Glu Ala Ala Asp Leu Ala Ala Ala Ala Ala Asp Pro Gln Ala
            180                 185                 190

Asp Thr Lys Ser Lys Leu Val Lys Leu Val Val Met Val Cys Glu Gly
```

|     | 195 |     |     |     |     | 200 |     |     |     |     | 205 |     |     |     |
|-----|-----|-----|-----|-----|-----|-----|-----|-----|-----|-----|-----|-----|-----|-----|
| Leu | Arg | Phe | Asn | Thr | Val | Ser | Arg | Thr | Val | Asp | Ala | Gly | Phe | Asn | Ser |
|     |     | 210 |     |     |     |     | 215 |     |     |     |     | 220 |     |     |     |
| Gln | His | Gly | Val | Thr | Leu | Thr | Val | Thr | Gln | Gly | Lys | Gln | Val | Gln | Lys |
| 225 |     |     |     |     | 230 |     |     |     |     | 235 |     |     |     |     | 240 |
| Trp | Asp | Arg | Ile | Ser | Lys | Ala | Ala | Phe | Glu | Trp | Ala | Asp | His | Pro | Thr |
|     |     |     |     | 245 |     |     |     |     | 250 |     |     |     |     | 255 |     |
| Ala | Val | Ile | Pro | Asp | Met | Gln | Lys | Leu | Gly | Ile | Lys | Asp | Lys | Asn | Glu |
|     |     |     | 260 |     |     |     |     | 265 |     |     |     |     | 270 |     |     |
| Ala | Ala | Arg | Ile | Val | Ala | Leu | Val | Lys | Asn | Gln | Thr | Thr | Ala | Ala | Ala |
|     |     | 275 |     |     |     |     | 280 |     |     |     |     | 285 |     |     |     |
| Ala | Thr | Ala | Ala | Ser | Ala | Asp | Asn | Asp | Asp | Asp | Glu | Ala |
|     | 290 |     |     |     |     | 295 |     |     |     |     | 300 |     |

( 2 ) INFORMATION FOR SEQ ID NO:3:

( i ) SEQUENCE CHARACTERISTICS:
        ( A ) LENGTH: 1105 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| GCTTAATTAA | TTAAGCTTAA | AAGGAGGAAA | AAAATTATGG | CCGAGATAAC | CCTAGAGCCG | 60 |
|---|---|---|---|---|---|---|
| AGTGATCTTA | TGGCGCAAAC | AAACAAAAGA | ATAGTGCCAA | AGTTCACTGA | AATCTTCCCC | 120 |
| GTGGAGGACG | CGAACTACCC | TTACAGCGCC | TTCATCGCGT | CGGTCCGGAA | AGACGTGATC | 180 |
| AAACACTGCA | CCGACCATAA | AGGGATCTTC | CAGCCCGTGC | TGCCACCGGA | GAAGAAGGTC | 240 |
| CCGGAGCTAT | GGTTCTACAC | AGAGCTCAAA | ACTAGGACCA | GCTCCATCAC | GCTCGCCATA | 300 |
| CGCATGGACA | ACCTGTACCT | CGTGGGCTTC | AGGACCCCGG | GCGGGGTGTG | GTGGGAGTTC | 360 |
| GGCAAGGACG | GCGACACCCA | CCTCCTCGGC | GACAACCCCA | GGTGGCTCGG | CTTCGGCGGC | 420 |
| AGGTACCAGG | ACCTCATCGG | CAACAAGGGT | CTGGAGACCG | TCACCATGGG | CCGCGCCGAA | 480 |
| ATGACCAGGG | CCGTCAACGA | CCTGGCGAAG | AAGAAGAAGA | TGGCGACACT | GGAGGAGGAG | 540 |
| GAGGTGAAGA | TGCAGATGCA | GATGCCGGAG | GCCGCTGATC | TGGCGGCGGC | GGCAGCGGCT | 600 |
| GACCCACAGG | CCGACACGAA | GAGCAAGCTG | GTGAAGCTGG | TGGTCATGGT | GTGCGAGGGG | 660 |
| CTGCGGTTCA | ACACCGTGTC | CCGCACGGTG | GACGCGGGGT | TCAACAGCCA | GCACGGGGTG | 720 |
| ACCTTGACCG | TGACGCAGGG | GAAGCAGGTG | CAGAAGTGGG | ACAGGATCTC | CAAGGCGGCC | 780 |
| TTCGAGTGGG | CTGACCACCC | CACCGCTGTG | ATCCCCGACA | TGCAGAAGCT | TGGCATCAAG | 840 |
| GATAAGAACG | AAGCAGCGAG | GATCGTTGCG | CTCGTTAAGA | ATCAAACTAC | TGCCGCTGCC | 900 |
| GCTACTGCTG | CCAGTGCTGA | CAACGACGAC | GACGAGGCCT | GATCAATGCA | ACGACACATC | 960 |
| ATGATCTGCT | GCTGCACTTA | ATTACTATGT | TCGTATACAA | ATAAATACAC | CCGGCGTACG | 1020 |
| CGGTGTTCCT | TATATGGTCT | AAAATGTAGC | CAGTAAATTT | TAAACTACTT | TCTCGTGCCG | 1080 |
| AATTCACTGG | CCGGCATGCT | ATATA |     |     |     | 1105 |

( 2 ) INFORMATION FOR SEQ ID NO:4:

( i ) SEQUENCE CHARACTERISTICS:
        ( A ) LENGTH: 1074 base pairs
        ( B ) TYPE: nucleic acid
        ( C ) STRANDEDNESS: single
        ( D ) TOPOLOGY: linear ( i x ) FEATURE:
    ( A ) NAME/KEY: CDS
    ( B ) LOCATION: 51..911

( x i ) SEQUENCE DESCRIPTION: SEQ ID NO:4:

```
TCCCTCTAGA TGCGGCCTAA TTAATTAAGC TTAAAAGGAG GAAAAAAATT ATG AAA          56
                                                        Met Lys
                                                         1

AGA ATA GTG CCA AAG TTC ACT GAA ATC TTC CCC GTG GAG GAC GCG AAC         104
Arg Ile Val Pro Lys Phe Thr Glu Ile Phe Pro Val Glu Asp Ala Asn
         5                   10                  15

TAC CCT TAC AGC GCC TTC ATC GCG TCG GTC CGG AAA GAC GTG ATC AAA         152
Tyr Pro Tyr Ser Ala Phe Ile Ala Ser Val Arg Lys Asp Val Ile Lys
     20                  25                  30

CAC TGC ACC GAC CAT AAA GGG ATC TTC CAG CCC GTG CTG CCA CCG GAG         200
His Cys Thr Asp His Lys Gly Ile Phe Gln Pro Val Leu Pro Pro Glu
 35              40                  45                      50

AAG AAG GTC CCG GAG CTA TGG TTC TAC ACA GAG CTC AAA ACT AGG ACC         248
Lys Lys Val Pro Glu Leu Trp Phe Tyr Thr Glu Leu Lys Thr Arg Thr
                 55                  60                  65

AGC TCC ATC ACG CTC GCC ATA CGC ATG GAC AAC CTG TAC CTC GTG GGC         296
Ser Ser Ile Thr Leu Ala Ile Arg Met Asp Asn Leu Tyr Leu Val Gly
             70                  75                  80

TTC AGG ACC CCG GGC GGG GTG TGG TGG GAG TTC GGC AAG GAC GGC GAC         344
Phe Arg Thr Pro Gly Gly Val Trp Trp Glu Phe Gly Lys Asp Gly Asp
         85                  90                  95

ACC CAC CTC CTC GGC GAC AAC CCC AGG TGG CTC GGC TTC GGC GGC AGG         392
Thr His Leu Leu Gly Asp Asn Pro Arg Trp Leu Gly Phe Gly Gly Arg
     100                 105                 110

TAC CAG GAC CTC ATC GGC AAC AAG GGT CTG GAG ACC GTC ACC ATG GGC         440
Tyr Gln Asp Leu Ile Gly Asn Lys Gly Leu Glu Thr Val Thr Met Gly
115              120                 125                     130

CGC GCC GAA ATG ACC AGG GCC GTC AAC GAC CTG GCG AAG AAG AAG AAG         488
Arg Ala Glu Met Thr Arg Ala Val Asn Asp Leu Ala Lys Lys Lys Lys
                 135                 140                 145

ATG GCG ACA CTG GAG GAG GAG GAG GTG AAG ATG CAG ATG CAG ATG CCG         536
Met Ala Thr Leu Glu Glu Glu Glu Val Lys Met Gln Met Gln Met Pro
             150                 155                 160

GAG GCC GCT GAT CTG GCG GCG GCG GCA GCG GCT GAC CCA CAG GCC GAC         584
Glu Ala Ala Asp Leu Ala Ala Ala Ala Ala Ala Asp Pro Gln Ala Asp
                 165                 170                 175

ACG AAG AGC AAG CTG GTG AAG CTG GTG GTC ATG GTG TGC GAG GGG CTG         632
Thr Lys Ser Lys Leu Val Lys Leu Val Val Met Val Cys Glu Gly Leu
         180                 185                 190

CGG TTC AAC ACC GTG TCC CGC ACG GTG GAC GCG GGG TTC AAC AGC CAG         680
Arg Phe Asn Thr Val Ser Arg Thr Val Asp Ala Gly Phe Asn Ser Gln
195                 200                 205                 210

CAC GGG GTG ACC TTG ACC GTG ACG CAG GGG AAG CAG GTG CAG AAG TGG         728
His Gly Val Thr Leu Thr Val Thr Gln Gly Lys Gln Val Gln Lys Trp
             215                 220                 225

GAC AGG ATC TCC AAG GCG GCC TTC GAG TGG GCT GAC CAC CCC ACC GCT         776
Asp Arg Ile Ser Lys Ala Ala Phe Glu Trp Ala Asp His Pro Thr Ala
         230                 235                 240

GTG ATC CCC GAC ATG CAG AAG CTT GGC ATC AAG GAT AAG AAC GAA GCA         824
Val Ile Pro Asp Met Gln Lys Leu Gly Ile Lys Asp Lys Asn Glu Ala
         245                 250                 255

GCG AGG ATC GTT GCG CTC GTT AAG AAT CAA ACT ACT GCC GCT GCC GCT         872
Ala Arg Ile Val Ala Leu Val Lys Asn Gln Thr Thr Ala Ala Ala Ala
     260                 265                 270

ACT GCT GCC AGT GCT GAC AAC GAC GAC GAC GAG GCC TGATCAATGC              918
Thr Ala Ala Ser Ala Asp Asn Asp Asp Asp Glu Ala
```

```
        275                    280                    285
AACGACACAT  CATGATCTGC  TGCTGCACTT  AATTACTATG  TTCGTATACA  AATAAATACA    978

CCCGGCGTAC  GCGGTGTTCC  TTATATGGTC  TAAAATGTAG  CCAGTAAATT  TTAAACTACT   1038

TTCTCGTGCC  GAATTCACTG  GCCGGCATGC  TATATA                                1074
```

( 2 ) INFORMATION FOR SEQ ID NO:5:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Lys Arg Ile Val Pro Lys Phe Thr Glu Ile Phe Pro Val Glu Asp
 1               5                  10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
               100                 105                 110

Gly Arg Tyr Gln Asp Leu Ile Gly Asn Lys Gly Leu Glu Thr Val Thr
           115                 120                 125

Met Gly Arg Ala Glu Met Thr Arg Ala Val Asn Asp Leu Ala Lys Lys
       130                 135                 140

Lys Lys Met Ala Thr Leu Glu Glu Glu Glu Val Lys Met Gln Met Gln
145                 150                 155                 160

Met Pro Glu Ala Ala Asp Leu Ala Ala Ala Ala Ala Asp Pro Gln
               165                 170                 175

Ala Asp Thr Lys Ser Lys Leu Val Lys Leu Val Val Met Val Cys Glu
           180                 185                 190

Gly Leu Arg Phe Asn Thr Val Ser Arg Thr Val Asp Ala Gly Phe Asn
       195                 200                 205

Ser Gln His Gly Val Thr Leu Thr Val Thr Gln Gly Lys Gln Val Gln
   210                 215                 220

Lys Trp Asp Arg Ile Ser Lys Ala Ala Phe Glu Trp Ala Asp His Pro
225                 230                 235                 240

Thr Ala Val Ile Pro Asp Met Gln Lys Leu Gly Ile Lys Asp Lys Asn
               245                 250                 255

Glu Ala Ala Arg Ile Val Ala Leu Val Lys Asn Gln Thr Thr Ala Ala
           260                 265                 270

Ala Ala Thr Ala Ala Ser Ala Asp Asn Asp Asp Asp Glu Ala
       275                 280                 285
```

( 2 ) INFORMATION FOR SEQ ID NO:6:

( i ) SEQUENCE CHARACTERISTICS:
        ( A ) LENGTH: 1029 base pairs
        ( B ) TYPE: nucleic acid ( C ) STRANDEDNESS: single
( D ) TOPOLOGY: linear ( i x ) FEATURE:
( A ) NAME/KEY: CDS
( B ) LOCATION: 36..863

( x i ) SEQUENCE DESCRIPTION: SEQ ID NO:6:

| | | | | | | | | | | | | | | | | | | |
|---|---|---|---|---|---|---|---|---|---|---|---|---|---|---|---|---|---|---|
| GCTAATTAAT | TAAGCTTAAA | AGGAGGAAAA | AAATT | ATG | GCC | GAG | ATA | ACC | CTA | | | | | | | | | 53 |
| | | | | Met | Ala | Glu | Ile | Thr | Leu | | | | | | | | | |
| | | | | 1 | | | | 5 | | | | | | | | | | |
| GAG | CCG | AGT | GAT | CTT | ATG | GCG | CAA | ACA | AAC | AAA | AGA | ATA | GTG | CCA | AAG | | | 101 |
| Glu | Pro | Ser | Asp | Leu | Met | Ala | Gln | Thr | Asn | Lys | Arg | Ile | Val | Pro | Lys | | | |
| | | | 10 | | | | 15 | | | | | 20 | | | | | | |
| TTC | ACT | GAA | ATC | TTC | CCC | GTG | GAG | GAC | GCG | AAC | TAC | CCT | TAC | AGC | GCC | | | 149 |
| Phe | Thr | Glu | Ile | Phe | Pro | Val | Glu | Asp | Ala | Asn | Tyr | Pro | Tyr | Ser | Ala | | | |
| | | 25 | | | | 30 | | | | | 35 | | | | | | | |
| TTC | ATC | GCG | TCG | GTC | CGG | AAA | GAC | GTG | ATC | AAA | CAC | TGC | ACC | GAC | CAT | | | 197 |
| Phe | Ile | Ala | Ser | Val | Arg | Lys | Asp | Val | Ile | Lys | His | Cys | Thr | Asp | His | | | |
| | 40 | | | | 45 | | | | | 50 | | | | | | | | |
| AAA | GGG | ATC | TTC | CAG | CCC | GTG | CTG | CCA | CCG | GAG | AAG | AAG | GTC | CCG | GAG | | | 245 |
| Lys | Gly | Ile | Phe | Gln | Pro | Val | Leu | Pro | Pro | Glu | Lys | Lys | Val | Pro | Glu | | | |
| 55 | | | | 60 | | | | | 65 | | | | | 70 | | | | |
| CTA | TGG | TTC | TAC | ACA | GAG | CTC | AAA | ACT | AGG | ACC | AGC | TCC | ATC | ACG | CTC | | | 293 |
| Leu | Trp | Phe | Tyr | Thr | Glu | Leu | Lys | Thr | Arg | Thr | Ser | Ser | Ile | Thr | Leu | | | |
| | | | 75 | | | | 80 | | | | | 85 | | | | | | |
| GCC | ATA | CGC | ATG | GAC | AAC | CTG | TAC | CTC | GTG | GGC | TTC | AGG | ACC | CCG | GGC | | | 341 |
| Ala | Ile | Arg | Met | Asp | Asn | Leu | Tyr | Leu | Val | Gly | Phe | Arg | Thr | Pro | Gly | | | |
| | | 90 | | | | 95 | | | | | 100 | | | | | | | |
| GGG | GTG | TGG | TGG | GAG | TTC | GGC | AAG | GAC | GGC | GAC | ACC | CAC | CTC | CTC | GGC | | | 389 |
| Gly | Val | Trp | Trp | Glu | Phe | Gly | Lys | Asp | Gly | Asp | Thr | His | Leu | Leu | Gly | | | |
| | 105 | | | | 110 | | | | | 115 | | | | | | | | |
| GAC | AAC | CCC | AGG | TGG | CTC | GGC | TTC | GGC | GGC | AGG | TAC | CAG | GAC | CTC | ATC | | | 437 |
| Asp | Asn | Pro | Arg | Trp | Leu | Gly | Phe | Gly | Gly | Arg | Tyr | Gln | Asp | Leu | Ile | | | |
| 120 | | | | 125 | | | | | 130 | | | | | | | | | |
| GGC | AAC | AAG | GGT | CTG | GAG | ACC | GTC | ACC | ATG | GGC | CGC | GCC | GAA | ATG | ACC | | | 485 |
| Gly | Asn | Lys | Gly | Leu | Glu | Thr | Val | Thr | Met | Gly | Arg | Ala | Glu | Met | Thr | | | |
| 135 | | | | 140 | | | | 145 | | | | | 150 | | | | | |
| AGG | GCC | GTC | AAC | GAC | CTG | GCG | AAG | AAG | AAG | GCG | GCT | GAC | CCA | CAG | | | | 533 |
| Arg | Ala | Val | Asn | Asp | Leu | Ala | Lys | Lys | Lys | Ala | Ala | Asp | Pro | Gln | | | | |
| | | | 155 | | | | | 160 | | | | | 165 | | | | | |
| GCC | GAC | ACG | AAG | AGC | AAG | CTG | GTG | AAG | CTG | GTG | GTC | ATG | GTG | TGC | GAG | | | 581 |
| Ala | Asp | Thr | Lys | Ser | Lys | Leu | Val | Lys | Leu | Val | Val | Met | Val | Cys | Glu | | | |
| | | | 170 | | | | 175 | | | | | 180 | | | | | | |
| GGG | CTG | CGG | TTC | AAC | ACC | GTG | TCC | CGC | ACG | GTG | GAC | GCG | GGG | TTC | AAC | | | 629 |
| Gly | Leu | Arg | Phe | Asn | Thr | Val | Ser | Arg | Thr | Val | Asp | Ala | Gly | Phe | Asn | | | |
| | | 185 | | | | 190 | | | | | 195 | | | | | | | |
| AGC | CAG | CAC | GGG | GTG | ACC | TTG | ACC | GTG | ACG | CAG | GGG | AAG | CAG | GTG | CAG | | | 677 |
| Ser | Gln | His | Gly | Val | Thr | Leu | Thr | Val | Thr | Gln | Gly | Lys | Gln | Val | Gln | | | |
| | 200 | | | | 205 | | | | | 210 | | | | | | | | |
| AAG | TGG | GAC | AGG | ATC | TCC | AAG | GCG | GCC | TTC | GAG | TGG | GCT | GAC | CAC | CCC | | | 725 |
| Lys | Trp | Asp | Arg | Ile | Ser | Lys | Ala | Ala | Phe | Glu | Trp | Ala | Asp | His | Pro | | | |
| 215 | | | | | 220 | | | | 225 | | | | | 230 | | | | |
| ACC | GCT | GTG | ATC | CCC | GAC | ATG | CAG | AAG | CTT | GGC | ATC | AAG | GAT | AAG | AAC | | | 773 |
| Thr | Ala | Val | Ile | Pro | Asp | Met | Gln | Lys | Leu | Gly | Ile | Lys | Asp | Lys | Asn | | | |
| | | | | 235 | | | | | 240 | | | | | 245 | | | | |
| GAA | GCA | GCG | AGG | ATC | GTT | GCG | CTC | GTT | AAG | AAT | CAA | ACT | ACT | GCC | GCT | | | 821 |
| Glu | Ala | Ala | Arg | Ile | Val | Ala | Leu | Val | Lys | Asn | Gln | Thr | Thr | Ala | Ala | | | |
| | | | 250 | | | | | 255 | | | | | 260 | | | | | |
| GCC | GCT | ACT | GCT | GCC | AGT | GCT | GAC | AAC | GAC | GAC | GAC | GAG | GCC | | | | | 863 |
| Ala | Ala | Thr | Ala | Ala | Ser | Ala | Asp | Asn | Asp | Asp | Asp | Glu | Ala | | | | | |
| | | 265 | | | | | 270 | | | | | 275 | | | | | | |

```
TGATCAATGC  AACGACACAT  CATGATCTGC  TGCTGCACTT  AATTACTATG  TTCGTATACA      923

AATAAATACA  CCCGGCGTAC  GCGGTGTTCC  TTATATGGTC  TAAAATGTAG  CCAGTAAATT      983

TTAAACTACT  TTCTCGTGCC  GAATTCACTG  GCCGGCATGC  TATATA                     1029
```

( 2 ) INFORMATION FOR SEQ ID NO:7:

( i ) SEQUENCE CHARACTERISTICS:
        ( A ) LENGTH: 276 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ala  Glu  Ile  Thr  Leu  Glu  Pro  Ser  Asp  Leu  Met  Ala  Gln  Thr  Asn
 1              5                        10                       15

Lys  Arg  Ile  Val  Pro  Lys  Phe  Thr  Glu  Ile  Phe  Pro  Val  Glu  Asp  Ala
               20                       25                       30

Asn  Tyr  Pro  Tyr  Ser  Ala  Phe  Ile  Ala  Ser  Val  Arg  Lys  Asp  Val  Ile
          35                       40                       45

Lys  His  Cys  Thr  Asp  His  Lys  Gly  Ile  Phe  Gln  Pro  Val  Leu  Pro  Pro
     50                       55                       60

Glu  Lys  Lys  Val  Pro  Glu  Leu  Trp  Phe  Tyr  Thr  Glu  Leu  Lys  Thr  Arg
65                       70                       75                       80

Thr  Ser  Ser  Ile  Thr  Leu  Ala  Ile  Arg  Met  Asp  Asn  Leu  Tyr  Leu  Val
                    85                       90                       95

Gly  Phe  Arg  Thr  Pro  Gly  Gly  Val  Trp  Trp  Glu  Phe  Gly  Lys  Asp  Gly
               100                     105                      110

Asp  Thr  His  Leu  Leu  Gly  Asp  Asn  Pro  Arg  Trp  Leu  Gly  Phe  Gly  Gly
          115                      120                      125

Arg  Tyr  Gln  Asp  Leu  Ile  Gly  Asn  Lys  Gly  Leu  Glu  Thr  Val  Thr  Met
     130                      135                      140

Gly  Arg  Ala  Glu  Met  Thr  Arg  Ala  Val  Asn  Asp  Leu  Ala  Lys  Lys  Lys
145                      150                      155                      160

Lys  Ala  Ala  Asp  Pro  Gln  Ala  Asp  Thr  Lys  Ser  Lys  Leu  Val  Lys  Leu
               165                      170                      175

Val  Val  Met  Val  Cys  Glu  Gly  Leu  Arg  Phe  Asn  Thr  Val  Ser  Arg  Thr
          180                      185                      190

Val  Asp  Ala  Gly  Phe  Asn  Ser  Gln  His  Gly  Val  Thr  Leu  Thr  Val  Thr
     195                      200                      205

Gln  Gly  Lys  Gln  Val  Gln  Lys  Trp  Asp  Arg  Ile  Ser  Lys  Ala  Ala  Phe
210                      215                      220

Glu  Trp  Ala  Asp  His  Pro  Thr  Ala  Val  Ile  Pro  Asp  Met  Gln  Lys  Leu
225                      230                      235                      240

Gly  Ile  Lys  Asp  Lys  Asn  Glu  Ala  Ala  Arg  Ile  Val  Ala  Leu  Val  Lys
               245                      250                      255

Asn  Gln  Thr  Thr  Ala  Ala  Ala  Ala  Thr  Ala  Ala  Ser  Ala  Asp  Asn  Asp
          260                      265                      270

Asp  Asp  Glu  Ala
          275
```

( 2 ) INFORMATION FOR SEQ ID NO:8:

( i ) SEQUENCE CHARACTERISTICS:
        ( A ) LENGTH: 985 base pairs
        ( B ) TYPE: nucleic acid
        ( C ) STRANDEDNESS: single -continued ( D ) TOPOLOGY: linear ( i x ) FEATURE:
    ( A ) NAME/KEY: CDS
    ( B ) LOCATION: 37..822

( x i ) SEQUENCE DESCRIPTION: SEQ ID NO:8:

```
GCTTAATTAA TTAAGCTTAA AAGGAGGAAA AAAATT ATG AAA AGA ATA GTG CCA              54
                                         Met Lys Arg Ile Val Pro
                                         1               5

AAG TTC ACT GAA ATC TTC CCC GTG GAG GAC GCG AAC TAC CCT TAC AGC             102
Lys Phe Thr Glu Ile Phe Pro Val Glu Asp Ala Asn Tyr Pro Tyr Ser
            10              15                      20

GCC TTC ATC GCG TCG GTC CGG AAA GAC GTG ATC AAA CAC TGC ACC GAC             150
Ala Phe Ile Ala Ser Val Arg Lys Asp Val Ile Lys His Cys Thr Asp
        25              30                  35

CAT AAA GGG ATC TTC CAG CCC GTG CTG CCA CCG GAG AAG AAG GTC CCG             198
His Lys Gly Ile Phe Gln Pro Val Leu Pro Pro Glu Lys Lys Val Pro
    40              45                  50

GAG CTA TGG TTC TAC ACA GAG CTC AAA ACT AGG ACC AGC TCC ATC ACG             246
Glu Leu Trp Phe Tyr Thr Glu Leu Lys Thr Arg Thr Ser Ser Ile Thr
55              60                  65                      70

CTC GCC ATA CGC ATG GAC AAC CTG TAC CTC GTG GGC TTC AGG ACC CCG             294
Leu Ala Ile Arg Met Asp Asn Leu Tyr Leu Val Gly Phe Arg Thr Pro
                75                  80                  85

GGC GGG GTG TGG TGG GAG TTC GGC AAG GAC GGC GAC ACC CAC CTC CTC             342
Gly Gly Val Trp Trp Glu Phe Gly Lys Asp Gly Asp Thr His Leu Leu
                90                  95                  100

GGC GAC AAC CCC AGG TGG CTC GGC TTC GGC GGC AGG TAC CAG GAC CTC             390
Gly Asp Asn Pro Arg Trp Leu Gly Phe Gly Gly Arg Tyr Gln Asp Leu
            105                 110                 115

ATC GGC AAC AAG GGT CTG GAG ACC GTC ACC ATG GGC CGC GCC GAA ATG             438
Ile Gly Asn Lys Gly Leu Glu Thr Val Thr Met Gly Arg Ala Glu Met
    120                 125                 130

ACC AGG GCC GTC AAC GAC CTG GCG AAG AAG AAG GCG GCT GAC CCA                 486
Thr Arg Ala Val Asn Asp Leu Ala Lys Lys Lys Ala Ala Asp Pro
135                 140                 145                 150

CAG GCC GAC ACG AAG AGC AAG CTG GTG AAG CTG GTG GTC ATG GTG TGC             534
Gln Ala Asp Thr Lys Ser Lys Leu Val Lys Leu Val Val Met Val Cys
                155                 160                 165

GAG GGG CTG CGG TTC AAC ACC GTG TCC CGC ACG GTG GAC GCG GGG TTC             582
Glu Gly Leu Arg Phe Asn Thr Val Ser Arg Thr Val Asp Ala Gly Phe
            170                 175                 180

AAC AGC CAG CAC GGG GTG ACC TTG ACC GTG ACG CAG GGG AAG CAG GTG             630
Asn Ser Gln His Gly Val Thr Leu Thr Val Thr Gln Gly Lys Gln Val
        185                 190                 195

CAG AAG TGG GAC AGG ATC TCC AAG GCG GCC TTC GAG TGG GCT GAC CAC             678
Gln Lys Trp Asp Arg Ile Ser Lys Ala Ala Phe Glu Trp Ala Asp His
200                 205                 210

CCC ACC GCT GTG ATC CCC GAC ATG CAG AAG CTT GGC ATC AAG GAT AAG             726
Pro Thr Ala Val Ile Pro Asp Met Gln Lys Leu Gly Ile Lys Asp Lys
215                 220                 225                 230

AAC GAA GCA GCG AGG ATC GTT GCG CTC GTT AAG AAT CAA ACT ACT GCC             774
Asn Glu Ala Ala Arg Ile Val Ala Leu Val Lys Asn Gln Thr Thr Ala
                235                 240                 245

GCT GCC GCT ACT GCT GCC AGT GCT GAC AAC GAC GAC GAC GAG GCC TGATCAATG       829
Ala Ala Ala Thr Ala Ala Ser Ala Asp Asn Asp Asp Asp Glu Ala
            250                 255                 260

AACGACACAT CATGATCTGC TGCTGCACTT AATTACTATG TTCGTATACA AATAAATACA           889

CCCGGCGTAC GCGGTGTTCC TTATATGGTC TAAAATGTAG CCAGTAAATT TTAAACTACT           949
```

TTCTCGTGCC GAATTCACTG GCCGGCATGC TATATA 985

( 2 ) INFORMATION FOR SEQ ID NO:9:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Lys | Arg | Ile | Val | Pro | Lys | Phe | Thr | Glu | Ile | Phe | Pro | Val | Glu | Asp |
|---|---|---|---|---|---|---|---|---|---|---|---|---|---|---|---|
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | 35 | | | | 40 | | | | | 45 | | | | |
| Pro | Glu | Lys | Lys | Val | Pro | Glu | Leu | Trp | Phe | Tyr | Thr | Glu | Leu | Lys | Thr |
| | 50 | | | | | 55 | | | | 60 | | | | | |
| Arg | Thr | Ser | Ser | Ile | Thr | Leu | Ala | Ile | Arg | Met | Asp | Asn | Leu | Tyr | Leu |
| 65 | | | | | 70 | | | | | 75 | | | | | 80 |
| Val | Gly | Phe | Arg | Thr | Pro | Gly | Gly | Val | Trp | Trp | Glu | Phe | Gly | Lys | Asp |
| | | | | 85 | | | | | 90 | | | | | 95 | |
| Gly | Asp | Thr | His | Leu | Leu | Gly | Asp | Asn | Pro | Arg | Trp | Leu | Gly | Phe | Gly |
| | | | 100 | | | | | 105 | | | | | 110 | | |
| Gly | Arg | Tyr | Gln | Asp | Leu | Ile | Gly | Asn | Lys | Gly | Leu | Glu | Thr | Val | Thr |
| | | 115 | | | | | 120 | | | | | 125 | | | |
| Met | Gly | Arg | Ala | Glu | Met | Thr | Arg | Ala | Val | Asn | Asp | Leu | Ala | Lys | Lys |
| | 130 | | | | | 135 | | | | | 140 | | | | |
| Lys | Lys | Ala | Ala | Asp | Pro | Gln | Ala | Asp | Thr | Lys | Ser | Lys | Leu | Val | Lys |
| 145 | | | | | 150 | | | | | 155 | | | | | 160 |
| Leu | Val | Val | Met | Val | Cys | Glu | Gly | Leu | Arg | Phe | Asn | Thr | Val | Ser | Arg |
| | | | | 165 | | | | | 170 | | | | | 175 | |
| Thr | Val | Asp | Ala | Gly | Phe | Asn | Ser | Gln | His | Gly | Val | Thr | Leu | Thr | Val |
| | | | 180 | | | | | 185 | | | | | 190 | | |
| Thr | Gln | Gly | Lys | Gln | Val | Gln | Lys | Trp | Asp | Arg | Ile | Ser | Lys | Ala | Ala |
| | | 195 | | | | | 200 | | | | | 205 | | | |
| Phe | Glu | Trp | Ala | Asp | His | Pro | Thr | Ala | Val | Ile | Pro | Asp | Met | Gln | Lys |
| | 210 | | | | | 215 | | | | | 220 | | | | |
| Leu | Gly | Ile | Lys | Asp | Lys | Asn | Glu | Ala | Ala | Arg | Ile | Val | Ala | Leu | Val |
| 225 | | | | | 230 | | | | | 235 | | | | | 240 |
| Lys | Asn | Gln | Thr | Thr | Ala | Ala | Ala | Ala | Thr | Ala | Ala | Ser | Ala | Asp | Asn |
| | | | | 245 | | | | | 250 | | | | | 255 | |
| Asp | Asp | Asp | Glu | Ala | | | | | | | | | | | |
| | | | 260 | | | | | | | | | | | | |

( 2 ) INFORMATION FOR SEQ ID NO:10:

( i ) SEQUENCE CHARACTERISTICS:
        ( A ) LENGTH: 978 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..815

( x i ) SEQUENCE DESCRIPTION: SEQ ID NO:10:

-continued

| | | | | | | | | | | | | | | | | |
|---|---|---|---|---|---|---|---|---|---|---|---|---|---|---|---|---|
| TCCCTCTAGA | TGCGGCCTAA | TTAATTAAGC | TTAAAAGGAG | GAAAAAAATT | ATG | AAA | | | | | | | | | | 56 |
| | | | | | Met | Lys | | | | | | | | | | |
| | | | | | 1 | | | | | | | | | | | |

| AGA | ATA | GTG | CCA | AAG | TTC | ACT | GAA | ATC | TTC | CCC | GTG | GAG | GAC | GCG | AAC | 104 |
|---|---|---|---|---|---|---|---|---|---|---|---|---|---|---|---|---|
| Arg | Ile | Val | Pro | Lys | Phe | Thr | Glu | Ile | Phe | Pro | Val | Glu | Asp | Ala | Asn | |
| | | 5 | | | | | 10 | | | | | 15 | | | | |

| TAC | CCT | TAC | AGC | GCC | TTC | ATC | GCG | TCG | GTC | CGG | AAA | GAC | GTG | ATC | AAA | 152 |
|---|---|---|---|---|---|---|---|---|---|---|---|---|---|---|---|---|
| Tyr | Pro | Tyr | Ser | Ala | Phe | Ile | Ala | Ser | Val | Arg | Lys | Asp | Val | Ile | Lys | |
| | 20 | | | | | 25 | | | | | 30 | | | | | |

| CAC | TGC | ACC | GAC | CAT | AAA | GGG | ATC | TTC | CAG | CCC | GTG | CTG | CCA | CCG | GAG | 200 |
|---|---|---|---|---|---|---|---|---|---|---|---|---|---|---|---|---|
| His | Cys | Thr | Asp | His | Lys | Gly | Ile | Phe | Gln | Pro | Val | Leu | Pro | Pro | Glu | |
| 35 | | | | | 40 | | | | 45 | | | | | | 50 | |

| AAG | AAG | GTC | CCG | GAG | CTA | TGG | TTC | TAC | ACA | GAG | CTC | AAA | ACT | AGG | ACC | 248 |
|---|---|---|---|---|---|---|---|---|---|---|---|---|---|---|---|---|
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |

| AGC | TCC | ATC | ACG | CTC | GCC | ATA | CGC | ATG | GAC | AAC | CTG | TAC | CTC | GTG | GGC | 296 |
|---|---|---|---|---|---|---|---|---|---|---|---|---|---|---|---|---|
| Ser | Ser | Ile | Thr | Leu | Ala | Ile | Arg | Met | Asp | Asn | Leu | Tyr | Leu | Val | Gly | |
| | | | 70 | | | | | 75 | | | | | 80 | | | |

| TTC | AGG | ACC | CCG | GGC | GGG | GTG | TGG | TGG | GAG | TTC | GGC | AAG | GAC | GGC | GAC | 344 |
|---|---|---|---|---|---|---|---|---|---|---|---|---|---|---|---|---|
| Phe | Arg | Thr | Pro | Gly | Gly | Val | Trp | Trp | Glu | Phe | Gly | Lys | Asp | Gly | Asp | |
| | | 85 | | | | | 90 | | | | | 95 | | | | |

| ACC | CAC | CTC | CTC | GGC | GAC | AAC | CCC | AGG | TGG | CTC | GGC | TTC | GGC | GGC | AGG | 392 |
|---|---|---|---|---|---|---|---|---|---|---|---|---|---|---|---|---|
| Thr | His | Leu | Leu | Gly | Asp | Asn | Pro | Arg | Trp | Leu | Gly | Phe | Gly | Gly | Arg | |
| | | 100 | | | | | 105 | | | | | 110 | | | | |

| TAC | CAG | GAC | CTC | ATC | GGC | AAC | AAG | GGT | CTG | GAG | ACC | GTC | ACC | ATG | GGC | 440 |
|---|---|---|---|---|---|---|---|---|---|---|---|---|---|---|---|---|
| Tyr | Gln | Asp | Leu | Ile | Gly | Asn | Lys | Gly | Leu | Glu | Thr | Val | Thr | Met | Gly | |
| 115 | | | | | 120 | | | | 125 | | | | | | 130 | |

| CGC | GCC | GAA | ATG | ACC | AGG | GCC | GTC | AAC | GAC | CTG | GCG | AAG | AAG | AAG | AAG | 488 |
|---|---|---|---|---|---|---|---|---|---|---|---|---|---|---|---|---|
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |

| GCG | GCT | GAC | CCA | CAG | GCC | GAC | ACG | AAG | AGC | AAG | CTG | GTG | AAG | CTG | GTG | 536 |
|---|---|---|---|---|---|---|---|---|---|---|---|---|---|---|---|---|
| Ala | Ala | Asp | Pro | Gln | Ala | Asp | Thr | Lys | Ser | Lys | Leu | Val | Lys | Leu | Val | |
| | | | 150 | | | | | 155 | | | | | 160 | | | |

| GTC | ATG | GTG | TGC | GAG | GGG | CTG | CGG | TTC | AAC | ACC | GTG | TCC | CGC | ACG | GTG | 584 |
|---|---|---|---|---|---|---|---|---|---|---|---|---|---|---|---|---|
| Val | Met | Val | Cys | Glu | Gly | Leu | Arg | Phe | Asn | Thr | Val | Ser | Arg | Thr | Val | |
| | | 165 | | | | | 170 | | | | | 175 | | | | |

| GAC | GCG | GGG | TTC | AAC | AGC | CAG | CAC | GGG | GTG | ACC | TTG | ACC | GTG | ACG | CAG | 632 |
|---|---|---|---|---|---|---|---|---|---|---|---|---|---|---|---|---|
| Asp | Ala | Gly | Phe | Asn | Ser | Gln | His | Gly | Val | Thr | Leu | Thr | Val | Thr | Gln | |
| | 180 | | | | | 185 | | | | | 190 | | | | | |

| GGG | AAG | CAG | GTG | CAG | AAG | TGG | GAC | AGG | ATC | TCC | AAG | GCG | GCC | TTC | GAG | 680 |
|---|---|---|---|---|---|---|---|---|---|---|---|---|---|---|---|---|
| Gly | Lys | Gln | Val | Gln | Lys | Trp | Asp | Arg | Ile | Ser | Lys | Ala | Ala | Phe | Glu | |
| 195 | | | | 200 | | | | | 205 | | | | | | 210 | |

| TGG | GCT | GAC | CAC | CCC | ACC | GCT | GTG | ATC | CCC | GAC | ATG | CAG | AAG | CTT | GGC | 728 |
|---|---|---|---|---|---|---|---|---|---|---|---|---|---|---|---|---|
| Trp | Ala | Asp | His | Pro | Thr | Ala | Val | Ile | Pro | Asp | Met | Gln | Lys | Leu | Gly | |
| | | | | 215 | | | | | 220 | | | | | 225 | | |

| ATC | AAG | GAT | AAG | AAC | GAA | GCA | GCG | AGG | ATC | GTT | GCG | CTC | GTT | AAG | AAT | 776 |
|---|---|---|---|---|---|---|---|---|---|---|---|---|---|---|---|---|
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |

| CAA | ACT | ACT | GCC | GCT | GCC | GCT | ACT | GCT | GGA | TCC | GCC | TGATCAATGC | | | | 822 |
|---|---|---|---|---|---|---|---|---|---|---|---|---|---|---|---|---|
| Gln | Thr | Thr | Ala | Ala | Ala | Ala | Thr | Ala | Gly | Ser | Ala | | | | | |
| | | 245 | | | | | 250 | | | | 255 | | | | | |

| AACGACACAT | CATGATCTGC | TGCTGCACTT | AATTACTATG | TTCGTATACA | AATAAATACA | 882 |
|---|---|---|---|---|---|---|
| CCCGGCGTAC | GCGGTGTTCC | TTATATGGTC | TAAAATGTAG | CCAGTAAATT | TTAAACTACT | 942 |
| TTCTCGTGCC | GAATTCACTG | GCCGGCATGC | TATATA | | | 978 |

( 2 ) INFORMATION FOR SEQ ID NO:11:

( i ) SEQUENCE CHARACTERISTICS:
        ( A ) LENGTH: 254 amino acids
        ( B ) TYPE: amino acid (D) TOPOLOGY: linear (ii) MOLECULE TYPE: protein (xi) SEQUENCE DESCRIPTION: SEQ ID NO:11:

| Met | Lys | Arg | Ile | Val | Pro | Lys | Phe | Thr | Glu | Ile | Phe | Pro | Val | Glu | Asp |
|---|---|---|---|---|---|---|---|---|---|---|---|---|---|---|---|
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | 35 | | | | | 40 | | | | | 45 | | | |
| Pro | Glu | Lys | Lys | Val | Pro | Glu | Leu | Trp | Phe | Tyr | Thr | Glu | Leu | Lys | Thr |
| | 50 | | | | | 55 | | | | | 60 | | | | |
| Arg | Thr | Ser | Ser | Ile | Thr | Leu | Ala | Ile | Arg | Met | Asp | Asn | Leu | Tyr | Leu |
| 65 | | | | | 70 | | | | | 75 | | | | | 80 |
| Val | Gly | Phe | Arg | Thr | Pro | Gly | Gly | Val | Trp | Trp | Glu | Phe | Gly | Lys | Asp |
| | | | | 85 | | | | | 90 | | | | | 95 | |
| Gly | Asp | Thr | His | Leu | Leu | Gly | Asp | Asn | Pro | Arg | Trp | Leu | Gly | Phe | Gly |
| | | | 100 | | | | | 105 | | | | | 110 | | |
| Gly | Arg | Tyr | Gln | Asp | Leu | Ile | Gly | Asn | Lys | Gly | Leu | Glu | Thr | Val | Thr |
| | | 115 | | | | | 120 | | | | | 125 | | | |
| Met | Gly | Arg | Ala | Glu | Met | Thr | Arg | Ala | Val | Asn | Asp | Leu | Ala | Lys | Lys |
| | 130 | | | | | 135 | | | | | 140 | | | | |
| Lys | Lys | Ala | Ala | Asp | Pro | Gln | Ala | Asp | Thr | Lys | Ser | Lys | Leu | Val | Lys |
| 145 | | | | | 150 | | | | | 155 | | | | | 160 |
| Leu | Val | Val | Met | Val | Cys | Glu | Gly | Leu | Arg | Phe | Asn | Thr | Val | Ser | Arg |
| | | | | 165 | | | | | 170 | | | | | 175 | |
| Thr | Val | Asp | Ala | Gly | Phe | Asn | Ser | Gln | His | Gly | Val | Thr | Leu | Thr | Val |
| | | | 180 | | | | | 185 | | | | | 190 | | |
| Thr | Gln | Gly | Lys | Gln | Val | Gln | Lys | Trp | Asp | Arg | Ile | Ser | Lys | Ala | Ala |
| | | 195 | | | | | 200 | | | | | 205 | | | |
| Phe | Glu | Trp | Ala | Asp | His | Pro | Thr | Ala | Val | Ile | Pro | Asp | Met | Gln | Lys |
| | 210 | | | | | 215 | | | | | 220 | | | | |
| Leu | Gly | Ile | Lys | Asp | Lys | Asn | Glu | Ala | Ala | Arg | Ile | Val | Ala | Leu | Val |
| 225 | | | | | 230 | | | | | 235 | | | | | 240 |
| Lys | Asn | Gln | Thr | Thr | Ala | Ala | Ala | Ala | Thr | Ala | Gly | Ser | Ala | | |
| | | | | 245 | | | | | 250 | | | | | | |

(2) INFORMATION FOR SEQ ID NO:12:

(i) SEQUENCE CHARACTERISTICS:
(A) LENGTH: 987 base pairs
(B) TYPE: nucleic acid
(C) STRANDEDNESS: single
(D) TOPOLOGY: linear (ix) FEATURE:
(A) NAME/KEY: CDS
(B) LOCATION: 51..824

(xi) SEQUENCE DESCRIPTION: SEQ ID NO:12:

```
TCCCTCTAGA TGCGGCCTAA TTAATTAAGC TTAAAAGGAG GAAAAAAATT ATG AAA        56
                                                      Met Lys
                                                       1

AGA ATA GTG CCA AAG TTC ACT GAA ATC TTC CCC GTG GAG GAC GCG AAC      104
Arg Ile Val Pro Lys Phe Thr Glu Ile Phe Pro Val Glu Asp Ala Asn
     5                  10                  15

TAC CCT TAC AGC GCC TTC ATC GCG TCG GTC CGG AAA GAC GTG ATC AAA      152
Tyr Pro Tyr Ser Ala Phe Ile Ala Ser Val Arg Lys Asp Val Ile Lys
         20                  25                  30
```

| | | | | | | | | | | | | | | | | |
|---|---|---|---|---|---|---|---|---|---|---|---|---|---|---|---|---|
| CAC | TGC | ACC | GAC | CAT | AAA | GGG | ATC | TTC | CAG | CCC | GTG | CTG | CCA | CCG | GAG | 200 |
| His | Cys | Thr | Asp | His | Lys | Gly | Ile | Phe | Gln | Pro | Val | Leu | Pro | Pro | Glu | |
| 35 | | | | 40 | | | | | 45 | | | | | | 50 | |
| AAG | AAG | GTC | CCG | GAG | CTA | TGG | TTC | TAC | ACA | GAG | CTC | AAA | ACT | AGG | ACC | 248 |
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |
| AGC | TCC | ATC | ACG | CTC | GCC | ATA | CGC | ATG | GAC | AAC | CTG | TAC | CTC | GTG | GGC | 296 |
| Ser | Ser | Ile | Thr | Leu | Ala | Ile | Arg | Met | Asp | Asn | Leu | Tyr | Leu | Val | Gly | |
| | | | 70 | | | | | 75 | | | | | 80 | | | |
| TTC | AGG | ACC | CCG | GGC | GGG | GTG | TGG | TGG | GAG | TTC | GGC | AAG | GAC | GGC | GAC | 344 |
| Phe | Arg | Thr | Pro | Gly | Gly | Val | Trp | Trp | Glu | Phe | Gly | Lys | Asp | Gly | Asp | |
| | | 85 | | | | | 90 | | | | | 95 | | | | |
| ACC | CAC | CTC | CTC | GGC | GAC | AAC | CCC | AGG | TGG | CTC | GGC | TTC | GGC | GGC | AGG | 392 |
| Thr | His | Leu | Leu | Gly | Asp | Asn | Pro | Arg | Trp | Leu | Gly | Phe | Gly | Gly | Arg | |
| | 100 | | | | | 105 | | | | | 110 | | | | | |
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | | 120 | | | | | 125 | | | | | 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| GCG | GCC | GCC | GCT | GCA | GAC | CCA | CAG | GCC | GAC | ACG | AAG | AGC | AAG | CTG | GTG | 536 |
| Ala | Ala | Ala | Ala | Ala | Asp | Pro | Gln | Ala | Asp | Thr | Lys | Ser | Lys | Leu | Val | |
| | | | 150 | | | | | 155 | | | | | 160 | | | |
| AAG | CTG | GTG | GTC | ATG | GTG | TGC | GAG | GGG | CTG | CGG | TTC | AAC | ACC | GTG | TCC | 584 |
| Lys | Leu | Val | Val | Met | Val | Cys | Glu | Gly | Leu | Arg | Phe | Asn | Thr | Val | Ser | |
| | | 165 | | | | | 170 | | | | | 175 | | | | |
| CGC | ACG | GTG | GAC | GCG | GGG | TTC | AAC | AGC | CAG | CAC | GGG | GTG | ACC | TTG | ACC | 632 |
| Arg | Thr | Val | Asp | Ala | Gly | Phe | Asn | Ser | Gln | His | Gly | Val | Thr | Leu | Thr | |
| | 180 | | | | | 185 | | | | | 190 | | | | | |
| GTG | ACG | CAG | GGG | AAG | CAG | GTG | CAG | AAG | TGG | GAC | AGG | ATC | TCC | AAG | GCG | 680 |
| Val | Thr | Gln | Gly | Lys | Gln | Val | Gln | Lys | Trp | Asp | Arg | Ile | Ser | Lys | Ala | |
| 195 | | | | | 200 | | | | | 205 | | | | | 210 | |
| GCC | TTC | GAG | TGG | GCT | GAC | CAC | CCC | ACC | GCT | GTG | ATC | CCC | GAC | ATG | CAG | 728 |
| Ala | Phe | Glu | Trp | Ala | Asp | His | Pro | Thr | Ala | Val | Ile | Pro | Asp | Met | Gln | |
| | | | | 215 | | | | | 220 | | | | | 225 | | |
| AAG | CTT | GGC | ATC | AAG | GAT | AAG | AAC | GAA | GCA | GCG | AGG | ATC | GTT | GCG | CTC | 776 |
| Lys | Leu | Gly | Ile | Lys | Asp | Lys | Asn | Glu | Ala | Ala | Arg | Ile | Val | Ala | Leu | |
| | | | 230 | | | | | 235 | | | | | 240 | | | |
| GTT | AAG | AAT | CAA | ACT | ACT | GCC | GCT | GCC | GCT | ACT | GCT | GGA | TCC | GCC | TGATCAATG | 831 |
| Val | Lys | Asn | Gln | Thr | Thr | Ala | Ala | Ala | Ala | Thr | Ala | Gly | Ser | Ala | | |
| | | 245 | | | | | 250 | | | | | 255 | | | | |

AACGACACAT CATGATCTGC TGCTGCACTT AATTACTATG TTCGTATACA AATAAATACA    891

CCCGGCGTAC GCGGTGTTCC TTATATGGTC TAAAATGTAG CCAGTAAATT TTAAACTACT    951

TTCTCGTGCC GAATTCACTG GCCGGCATGC TATATA    987

( 2 ) INFORMATION FOR SEQ ID NO:13:

( i ) SEQUENCE CHARACTERISTICS:
        ( A ) LENGTH: 257 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Met | Lys | Arg | Ile | Val | Pro | Lys | Phe | Thr | Glu | Ile | Phe | Pro | Val | Glu | Asp |
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |

| Ile | Lys | His | Cys | Thr | Asp | His | Lys | Gly | Ile | Phe | Gln | Pro | Val | Leu | Pro |
|---|---|---|---|---|---|---|---|---|---|---|---|---|---|---|---|
| | | 35 | | | | 40 | | | | | 45 | | | | |

| Pro | Glu | Lys | Lys | Val | Pro | Glu | Leu | Trp | Phe | Tyr | Thr | Glu | Leu | Lys | Thr |
|---|---|---|---|---|---|---|---|---|---|---|---|---|---|---|---|
| | 50 | | | | | 55 | | | | | | 60 | | | |

| Arg | Thr | Ser | Ser | Ile | Thr | Leu | Ala | Ile | Arg | Met | Asp | Asn | Leu | Tyr | Leu |
|---|---|---|---|---|---|---|---|---|---|---|---|---|---|---|---|
| 65 | | | | | 70 | | | | | 75 | | | | | 80 |

| Val | Gly | Phe | Arg | Thr | Pro | Gly | Gly | Val | Trp | Trp | Glu | Phe | Gly | Lys | Asp |
|---|---|---|---|---|---|---|---|---|---|---|---|---|---|---|---|
| | | | | 85 | | | | | 90 | | | | | 95 | |

| Gly | Asp | Thr | His | Leu | Leu | Gly | Asp | Asn | Pro | Arg | Trp | Leu | Gly | Phe | Gly |
|---|---|---|---|---|---|---|---|---|---|---|---|---|---|---|---|
| | | | 100 | | | | | 105 | | | | | 110 | | |

| Gly | Arg | Tyr | Gln | Asp | Leu | Ile | Gly | Asn | Lys | Gly | Leu | Glu | Thr | Val | Thr |
|---|---|---|---|---|---|---|---|---|---|---|---|---|---|---|---|
| | | 115 | | | | | 120 | | | | | 125 | | | |

| Met | Gly | Arg | Ala | Glu | Met | Thr | Arg | Ala | Val | Asn | Asp | Leu | Ala | Lys | Lys |
|---|---|---|---|---|---|---|---|---|---|---|---|---|---|---|---|
| | 130 | | | | | 135 | | | | | 140 | | | | |

| Lys | Lys | Ala | Ala | Ala | Ala | Ala | Asp | Pro | Gln | Ala | Asp | Thr | Lys | Ser | Lys |
|---|---|---|---|---|---|---|---|---|---|---|---|---|---|---|---|
| 145 | | | | | 150 | | | | | 155 | | | | | 160 |

| Leu | Val | Lys | Leu | Val | Val | Met | Val | Cys | Glu | Gly | Leu | Arg | Phe | Asn | Thr |
|---|---|---|---|---|---|---|---|---|---|---|---|---|---|---|---|
| | | | | 165 | | | | | 170 | | | | | 175 | |

| Val | Ser | Arg | Thr | Val | Asp | Ala | Gly | Phe | Asn | Ser | Gln | His | Gly | Val | Thr |
|---|---|---|---|---|---|---|---|---|---|---|---|---|---|---|---|
| | | | 180 | | | | | 185 | | | | | 190 | | |

| Leu | Thr | Val | Thr | Gln | Gly | Lys | Gln | Val | Gln | Lys | Trp | Asp | Arg | Ile | Ser |
|---|---|---|---|---|---|---|---|---|---|---|---|---|---|---|---|
| | | 195 | | | | | 200 | | | | | 205 | | | |

| Lys | Ala | Ala | Phe | Glu | Trp | Ala | Asp | His | Pro | Thr | Ala | Val | Ile | Pro | Asp |
|---|---|---|---|---|---|---|---|---|---|---|---|---|---|---|---|
| | 210 | | | | | 215 | | | | | 220 | | | | |

| Met | Gln | Lys | Leu | Gly | Ile | Lys | Asp | Lys | Asn | Glu | Ala | Ala | Arg | Ile | Val |
|---|---|---|---|---|---|---|---|---|---|---|---|---|---|---|---|
| 225 | | | | | 230 | | | | | 235 | | | | | 240 |

| Ala | Leu | Val | Lys | Asn | Gln | Thr | Thr | Ala | Ala | Ala | Ala | Thr | Ala | Gly | Ser |
|---|---|---|---|---|---|---|---|---|---|---|---|---|---|---|---|
| | | | | 245 | | | | | 250 | | | | | 255 | |

Ala ( 2 ) INFORMATION FOR SEQ ID NO:14:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..998

( x i ) SEQUENCE DESCRIPTION: SEQ ID NO:14:

```
TCCCTCTAGA TGCGGCCTAA TTAATTAAGC TTAAAAGGAG GAAAAAAATT ATG AAA       56
                                                      Met Lys
                                                       1
```

| AGA | ATA | GTG | CCA | AAG | TTC | ACT | GAA | ATC | TTC | CCC | GTG | GAG | GAC | GCG | AAC | 104 |
|---|---|---|---|---|---|---|---|---|---|---|---|---|---|---|---|---|
| Arg | Ile | Val | Pro | Lys | Phe | Thr | Glu | Ile | Phe | Pro | Val | Glu | Asp | Ala | Asn | |
| | | | 5 | | | | | 10 | | | | | 15 | | | |

| TAC | CCT | TAC | AGC | GCC | TTC | ATC | GCG | TCG | GTC | CGG | AAA | GAC | GTG | ATC | AAA | 152 |
|---|---|---|---|---|---|---|---|---|---|---|---|---|---|---|---|---|
| Tyr | Pro | Tyr | Ser | Ala | Phe | Ile | Ala | Ser | Val | Arg | Lys | Asp | Val | Ile | Lys | |
| | | 20 | | | | | 25 | | | | | 30 | | | | |

| CAC | TGC | ACC | GAC | CAT | AAA | GGG | ATC | TTC | CAG | CCC | GTG | CTG | CCA | CCG | GAG | 200 |
|---|---|---|---|---|---|---|---|---|---|---|---|---|---|---|---|---|
| His | Cys | Thr | Asp | His | Lys | Gly | Ile | Phe | Gln | Pro | Val | Leu | Pro | Pro | Glu | |
| 35 | | | | | 40 | | | | | 45 | | | | | 50 | |

| AAG | AAG | GTC | CCG | GAG | CTA | TGG | TTC | TAC | ACA | GAG | CTC | AAA | ACT | AGG | ACC | 248 |
|---|---|---|---|---|---|---|---|---|---|---|---|---|---|---|---|---|
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |

| | | | | | | | | | | | | | | | | |
|---|---|---|---|---|---|---|---|---|---|---|---|---|---|---|---|---|
| AGC | TCC | ATC | ACG | CTC | GCC | ATA | CGC | ATG | GAC | AAC | CTG | TAC | CTC | GTG | GGC | 296 |
| Ser | Ser | Ile | Thr 70 | Leu | Ala | Ile | Arg | Met 75 | Asp | Asn | Leu | Tyr | Leu 80 | Val | Gly | |
| TTC | AGG | ACC | CCG | GGC | GGG | GTG | TGG | TGG | GAG | TTC | GGC | AAG | GAC | GGC | GAC | 344 |
| Phe | Arg | Thr 85 | Pro | Gly | Gly | Val | Trp | Trp 90 | Glu | Phe | Gly | Lys 95 | Asp | Gly | Asp | |
| ACC | CAC | CTC | CTC | GGC | GAC | AAC | CCC | AGG | TGG | CTC | GGC | TTC | GGC | GGC | AGG | 392 |
| Thr | His 100 | Leu | Leu | Gly | Asp | Asn | Pro 105 | Arg | Trp | Leu | Gly | Phe 110 | Gly | Gly | Arg | |
| TAC | CAG | GAC | CTC | ATC | GGC | AAC | AAG | GGT | CTG | GAG | ACC | GTC | ACC | ATG | GGC | 440 |
| Tyr 115 | Gln | Asp | Leu | Ile | Gly 120 | Asn | Lys | Gly | Leu | Glu 125 | Thr | Val | Thr | Met | Gly 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr 135 | Arg | Ala | Val | Asn | Asp 140 | Leu | Ala | Lys | Lys | Lys 145 | Lys | |
| GCG | GCT | GAC | CCA | CAG | GCC | GAC | ACG | AAG | AGC | AAG | CTG | GTG | AAG | CTG | GTG | 536 |
| Ala | Ala | Asp | Pro 150 | Gln | Ala | Asp | Thr | Lys 155 | Ser | Lys | Leu | Val | Lys 160 | Leu | Val | |
| GTC | ATG | GTG | TGC | GAG | GGG | CTG | CGG | TTC | AAC | ACC | GTG | TCC | CGC | ACG | GTG | 584 |
| Val | Met | Val 165 | Cys | Glu | Gly | Leu | Arg 170 | Phe | Asn | Thr | Val | Ser 175 | Arg | Thr | Val | |
| GAC | GCG | GGG | TTC | AAC | AGC | CAG | CAC | GGG | GTG | ACC | TTG | ACC | GTG | ACG | CAG | 632 |
| Asp | Ala 180 | Gly | Phe | Asn | Ser | Gln 185 | His | Gly | Val | Thr | Leu 190 | Thr | Val | Thr | Gln | |
| GGG | AAG | CAG | GTG | CAG | AAG | TGG | GAC | AGG | ATC | TCC | AAG | GCG | GCC | TTC | GAG | 680 |
| Gly 195 | Lys | Gln | Val | Gln 200 | Lys | Trp | Asp | Arg | Ile 205 | Ser | Lys | Ala | Ala | Phe 210 | Glu | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro 215 | Thr | Ala | Val | Ile | Pro 220 | Asp | Met | Gln | Lys | Leu 225 | Gly | |
| ATC | AAG | GAT | AAG | AAC | GAA | GCA | GCG | AGG | ATC | GTT | GCG | CTC | GTT | AAG | AAT | 776 |
| Ile | Lys | Asp | Lys 230 | Asn | Glu | Ala | Ala | Arg 235 | Ile | Val | Ala | Leu | Val 240 | Lys | Asn | |
| CAA | ACT | ACT | GCC | GCT | GCC | GCT | ACT | GCT | GGA | TCC | GCT | GAT | AAC | AAT | TTC | 824 |
| Gln | Thr | Thr 245 | Ala | Ala | Ala | Ala | Thr 250 | Ala | Gly | Ser | Ala | Asp 255 | Asn | Asn | Phe | |
| AAC | AAA | GAA | CAA | CAA | AAT | GCT | TTC | TAT | GAA | ATC | TTG | AAT | ATG | CCT | AAC | 872 |
| Asn | Lys 260 | Glu | Gln | Gln | Asn | Ala 265 | Phe | Tyr | Glu | Ile | Leu 270 | Asn | Met | Pro | Asn | |
| TTA | AAC | GAA | GAA | CAA | CGC | AAT | GGT | TTC | ATC | CAA | AGC | TTA | AAA | GAT | GAC | 920 |
| Leu 275 | Asn | Glu | Glu | Gln | Arg 280 | Asn | Gly | Phe | Ile | Gln 285 | Ser | Leu | Lys | Asp | Asp 290 | |
| CCA | AGC | CAA | AGT | GCT | AAC | CTA | TTG | TCA | GAA | GCT | AAA | AAG | TTA | AAT | GAA | 968 |
| Pro | Ser | Gln | Ser | Ala 295 | Asn | Leu | Leu | Ser | Glu 300 | Ala | Lys | Lys | Leu | Asn 305 | Glu | |
| TCT | CAA | GCA | CCG | AAA | GAT | CGA | TCC | GCC | TGATCAATGC | | AACGACACAT | | | | | 1015 |
| Ser | Gln | Ala | Pro 310 | Lys | Asp | Arg | Ser | Ala 315 | | | | | | | | |

| | |
|---|---|
| CATGATCTGC TGCTGCACTT AATTACTATG TTCGTATACA AATAAATACA CCCGGCGTAC | 1075 |
| GCGGTGTTCC TTATATGGTC TAAAATGTAG CCAGTAAATT TTAAACTACT TTCTCGTGCC | 1135 |
| GAATTCACTG GCCGGCATGC TATATA | 1161 |

(2) INFORMATION FOR SEQ ID NO:15:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO:15:

```
Met Lys Arg Ile Val Pro Lys Phe Thr Glu Ile Phe Pro Val Glu Asp
 1               5                  10                  15
Ala Asn Tyr Pro Tyr Ser Ala Phe Ile Ala Ser Val Arg Lys Asp Val
             20                  25                  30
Ile Lys His Cys Thr Asp His Lys Gly Ile Phe Gln Pro Val Leu Pro
         35                  40                  45
Pro Glu Lys Lys Val Pro Glu Leu Trp Phe Tyr Thr Glu Leu Lys Thr
     50                  55                  60
Arg Thr Ser Ser Ile Thr Leu Ala Ile Arg Met Asp Asn Leu Tyr Leu
 65                  70                  75                  80
Val Gly Phe Arg Thr Pro Gly Gly Val Trp Trp Glu Phe Gly Lys Asp
                 85                  90                  95
Gly Asp Thr His Leu Leu Gly Asp Asn Pro Arg Trp Leu Gly Phe Gly
            100                 105                 110
Gly Arg Tyr Gln Asp Leu Ile Gly Asn Lys Gly Leu Glu Thr Val Thr
        115                 120                 125
Met Gly Arg Ala Glu Met Thr Arg Ala Val Asn Asp Leu Ala Lys Lys
130                 135                 140
Lys Lys Ala Ala Asp Pro Gln Ala Asp Thr Lys Ser Lys Leu Val Lys
145                 150                 155                 160
Leu Val Val Met Val Cys Glu Gly Leu Arg Phe Asn Thr Val Ser Arg
                165                 170                 175
Thr Val Asp Ala Gly Phe Asn Ser Gln His Gly Val Thr Leu Thr Val
            180                 185                 190
Thr Gln Gly Lys Gln Val Gln Lys Trp Asp Arg Ile Ser Lys Ala Ala
        195                 200                 205
Phe Glu Trp Ala Asp His Pro Thr Ala Val Ile Pro Asp Met Gln Lys
210                 215                 220
Leu Gly Ile Lys Asp Lys Asn Glu Ala Ala Arg Ile Val Ala Leu Val
225                 230                 235                 240
Lys Asn Gln Thr Thr Ala Ala Ala Ala Thr Ala Gly Ser Ala Asp Asn
                245                 250                 255
Asn Phe Asn Lys Glu Gln Gln Asn Ala Phe Tyr Glu Ile Leu Asn Met
            260                 265                 270
Pro Asn Leu Asn Glu Glu Gln Arg Asn Gly Phe Ile Gln Ser Leu Lys
        275                 280                 285
Asp Asp Pro Ser Gln Ser Ala Asn Leu Leu Ser Glu Ala Lys Lys Leu
290                 295                 300
Asn Glu Ser Gln Ala Pro Lys Asp Arg Ser Ala
305                 310                 315
```

(2) INFORMATION FOR SEQ ID NO:16:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 51..1256

(xi) SEQUENCE DESCRIPTION: SEQ ID NO:16:

```
TCCCTCTAGA TGCGGCCTAA TTAATTAAGC TTAAAAGGAG GAAAAAAATT ATG AAA      56
                                                         Met Lys
                                                          1
```

| | | | | | | | | | | | | | | | | |
|---|---|---|---|---|---|---|---|---|---|---|---|---|---|---|---|---|
| AGA | ATA | GTG | CCA | AAG | TTC | ACT | GAA | ATC | TTC | CCC | GTG | GAG | GAC | GCG | AAC | 104 |
| Arg | Ile | Val | Pro | Lys | Phe | Thr | Glu | Ile | Phe | Pro | Val | Glu | Asp | Ala | Asn | |
| | | 5 | | | | | 10 | | | | | 15 | | | | |
| TAC | CCT | TAC | AGC | GCC | TTC | ATC | GCG | TCG | GTC | CGG | AAA | GAC | GTG | ATC | AAA | 152 |
| Tyr | Pro | Tyr | Ser | Ala | Phe | Ile | Ala | Ser | Val | Arg | Lys | Asp | Val | Ile | Lys | |
| | 20 | | | | | 25 | | | | | 30 | | | | | |
| CAC | TGC | ACC | GAC | CAT | AAA | GGG | ATC | TTC | CAG | CCC | GTG | CTG | CCA | CCG | GAG | 200 |
| His | Cys | Thr | Asp | His | Lys | Gly | Ile | Phe | Gln | Pro | Val | Leu | Pro | Pro | Glu | |
| 35 | | | | 40 | | | | | 45 | | | | | | 50 | |
| AAG | AAG | GTC | CCG | GAG | CTA | TGG | TTC | TAC | ACA | GAG | CTC | AAA | ACT | AGG | ACC | 248 |
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |
| AGC | TCC | ATC | ACG | CTC | GCC | ATA | CGC | ATG | GAC | AAC | CTG | TAC | CTC | GTG | GGC | 296 |
| Ser | Ser | Ile | Thr | Leu | Ala | Ile | Arg | Met | Asp | Asn | Leu | Tyr | Leu | Val | Gly | |
| | | | 70 | | | | | 75 | | | | | 80 | | | |
| TTC | AGG | ACC | CCG | GGC | GGG | GTG | TGG | TGG | GAG | TTC | GGC | AAG | GAC | GGC | GAC | 344 |
| Phe | Arg | Thr | Pro | Gly | Gly | Val | Trp | Trp | Glu | Phe | Gly | Lys | Asp | Gly | Asp | |
| | | 85 | | | | | 90 | | | | | 95 | | | | |
| ACC | CAC | CTC | CTC | GGC | GAC | AAC | CCC | AGG | TGG | CTC | GGC | TTC | GGC | GGC | AGG | 392 |
| Thr | His | Leu | Leu | Gly | Asp | Asn | Pro | Arg | Trp | Leu | Gly | Phe | Gly | Gly | Arg | |
| | 100 | | | | | 105 | | | | | 110 | | | | | |
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | | 120 | | | | | 125 | | | | | 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| GCG | GCT | GAC | CCA | CAG | GCC | GAC | ACG | AAG | AGC | AAG | CTG | GTG | AAG | CTG | GTG | 536 |
| Ala | Ala | Asp | Pro | Gln | Ala | Asp | Thr | Lys | Ser | Lys | Leu | Val | Lys | Leu | Val | |
| | | | 150 | | | | | 155 | | | | | 160 | | | |
| GTC | ATG | GTG | TGC | GAG | GGG | CTG | CGG | TTC | AAC | ACC | GTG | TCC | CGC | ACG | GTG | 584 |
| Val | Met | Val | Cys | Glu | Gly | Leu | Arg | Phe | Asn | Thr | Val | Ser | Arg | Thr | Val | |
| | | 165 | | | | | 170 | | | | | 175 | | | | |
| GAC | GCG | GGG | TTC | AAC | AGC | CAG | CAC | GGG | GTG | ACC | TTG | ACC | GTG | ACG | CAG | 632 |
| Asp | Ala | Gly | Phe | Asn | Ser | Gln | His | Gly | Val | Thr | Leu | Thr | Val | Thr | Gln | |
| | 180 | | | | | 185 | | | | | 190 | | | | | |
| GGG | AAG | CAG | GTG | CAG | AAG | TGG | GAC | AGG | ATC | TCC | AAG | GCG | GCC | TTC | GAG | 680 |
| Gly | Lys | Gln | Val | Gln | Lys | Trp | Asp | Arg | Ile | Ser | Lys | Ala | Ala | Phe | Glu | |
| 195 | | | | | 200 | | | | | 205 | | | | | 210 | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro | Thr | Ala | Val | Ile | Pro | Asp | Met | Gln | Lys | Leu | Gly | |
| | | | | 215 | | | | | 220 | | | | | 225 | | |
| ATC | AAG | GAT | AAG | AAC | GAA | GCA | GCG | AGG | ATC | GTT | GCG | CTC | GTT | AAG | AAT | 776 |
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |
| CAA | ACT | ACT | GCC | GCT | GCC | GCT | ACT | GCT | GGA | TCC | AAA | CCA | GAA | GTG | ATC | 824 |
| Gln | Thr | Thr | Ala | Ala | Ala | Ala | Thr | Ala | Gly | Ser | Lys | Pro | Glu | Val | Ile | |
| | | 245 | | | | | 250 | | | | | 255 | | | | |
| GAT | GCG | TCT | GAA | TTA | ACA | CCA | GCC | GTG | ACA | ACT | TAC | AAA | CTT | GTT | ATT | 872 |
| Asp | Ala | Ser | Glu | Leu | Thr | Pro | Ala | Val | Thr | Thr | Tyr | Lys | Leu | Val | Ile | |
| | 260 | | | | | 265 | | | | | 270 | | | | | |
| AAT | GGT | AAA | ACA | TTG | AAA | GGC | GAA | ACA | ACT | ACT | GAA | GCT | GTT | GAT | GCT | 920 |
| Asn | Gly | Lys | Thr | Leu | Lys | Gly | Glu | Thr | Thr | Thr | Glu | Ala | Val | Asp | Ala | |
| 275 | | | | | 280 | | | | | 285 | | | | | 290 | |
| GCT | ACT | GCA | GAA | AAA | GTC | TTC | AAA | CAA | TAC | GCT | AAC | GAC | AAC | GGT | GTT | 968 |
| Ala | Thr | Ala | Glu | Lys | Val | Phe | Lys | Gln | Tyr | Ala | Asn | Asp | Asn | Gly | Val | |
| | | | | 295 | | | | | 300 | | | | | 305 | | |
| GAC | GGT | GAA | TGG | ACT | TAC | GAC | GAT | GCG | ACT | AAG | ACC | TTT | ACA | GTT | ACT | 1016 |
| Asp | Gly | Glu | Trp | Thr | Tyr | Asp | Asp | Ala | Thr | Lys | Thr | Phe | Thr | Val | Thr | |
| | | | 310 | | | | | 315 | | | | | 320 | | | |

```
GAA AAA CCA GAA GTG ATC GAT GCG TCT GAA TTA ACA CCA GCC GTG ACA      1064
Glu Lys Pro Glu Val Ile Asp Ala Ser Glu Leu Thr Pro Ala Val Thr
        325             330                 335

AGA TCC GCT GAT AAC AAT TTC AAC AAA GAA CAA CAA AAT GCT TTC TAT      1112
Arg Ser Ala Asp Asn Asn Phe Asn Lys Glu Gln Gln Asn Ala Phe Tyr
        340             345                 350

GAA ATC TTG AAT ATG CCT AAC TTA AAC GAA GAA CAA CGC AAT GGT TTC      1160
Glu Ile Leu Asn Met Pro Asn Leu Asn Glu Glu Gln Arg Asn Gly Phe
355             360                 365                 370

ATC CAA AGC TTA AAA GAT GAC CCA AGC CAA AGT GCT AAC CTA TTG TCA      1208
Ile Gln Ser Leu Lys Asp Asp Pro Ser Gln Ser Ala Asn Leu Leu Ser
                375                 380                 385

GAA GCT AAA AAG TTA AAT GAA TCT CAA GCA CCG AAA GAT CGA TCC GCC      1256
Glu Ala Lys Lys Leu Asn Glu Ser Gln Ala Pro Lys Asp Arg Ser Ala
        390                 395                 400

TGATCAATGC AACGACACAT CATGATCTGC TGCTGCACTT AATTACTATG TTCGTATACA    1316

AATAAATACA CCCGGCGTAC GCGGTGTTCC TTATATGGTC TAAAATGTAG CCAGTAAATT    1376

TTAAACTACT TTCTCGTGCC GAATTCACTG GCCGGCATGC TATATA                   1422
```

( 2 ) INFORMATION FOR SEQ ID NO:17:

( i ) SEQUENCE CHARACTERISTICS:
       ( A ) LENGTH: 402 amino acids
       ( B ) TYPE: amino acid
       ( D ) TOPOLOGY: linear ( i i ) MOLECULE TYPE: protein ( x i ) SEQUENCE DESCRIPTION: SEQ ID NO:17:

```
Met Lys Arg Ile Val Pro Lys Phe Thr Glu Ile Phe Pro Val Glu Asp
1               5                   10                  15

Ala Asn Tyr Pro Tyr Ser Ala Phe Ile Ala Ser Val Arg Lys Asp Val
                20                  25                  30

Ile Lys His Cys Thr Asp His Lys Gly Ile Phe Gln Pro Val Leu Pro
            35                  40                  45

Pro Glu Lys Lys Val Pro Glu Leu Trp Phe Tyr Thr Glu Leu Lys Thr
        50                  55                  60

Arg Thr Ser Ser Ile Thr Leu Ala Ile Arg Met Asp Asn Leu Tyr Leu
65                  70                  75                  80

Val Gly Phe Arg Thr Pro Gly Gly Val Trp Trp Glu Phe Gly Lys Asp
                85                  90                  95

Gly Asp Thr His Leu Leu Gly Asp Asn Pro Arg Trp Leu Gly Phe Gly
                100                 105                 110

Gly Arg Tyr Gln Asp Leu Ile Gly Asn Lys Gly Leu Glu Thr Val Thr
            115                 120                 125

Met Gly Arg Ala Glu Met Thr Arg Ala Val Asn Asp Leu Ala Lys Lys
        130                 135                 140

Lys Lys Ala Ala Asp Pro Gln Ala Asp Thr Lys Ser Lys Leu Val Lys
145                 150                 155                 160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
            180                 185                 190

Thr Gln Gly Lys Gln Val Gln Lys Trp Asp Arg Ile Ser Lys Ala Ala
        195                 200                 205

Phe Glu Trp Ala Asp His Pro Thr Ala Val Ile Pro Asp Met Gln Lys
210                 215                 220
```

| Leu | Gly | Ile | Lys | Asp | Lys | Asn | Glu | Ala | Ala | Arg | Ile | Val | Ala | Leu | Val |
| 225 | | | | 230 | | | | | 235 | | | | | | 240 |

| Lys | Asn | Gln | Thr | Thr | Ala | Ala | Ala | Ala | Thr | Ala | Gly | Ser | Lys | Pro | Glu |
| | | | | 245 | | | | | 250 | | | | | 255 | |

| Val | Ile | Asp | Ala | Ser | Glu | Leu | Thr | Pro | Ala | Val | Thr | Thr | Tyr | Lys | Leu |
| | | | 260 | | | | | 265 | | | | | 270 | | |

| Val | Ile | Asn | Gly | Lys | Thr | Leu | Lys | Gly | Glu | Thr | Thr | Thr | Glu | Ala | Val |
| | | 275 | | | | | 280 | | | | | 285 | | | |

| Asp | Ala | Ala | Thr | Ala | Glu | Lys | Val | Phe | Lys | Gln | Tyr | Ala | Asn | Asp | Asn |
| | 290 | | | | | 295 | | | | | 300 | | | | |

| Gly | Val | Asp | Gly | Glu | Trp | Thr | Tyr | Asp | Asp | Ala | Thr | Lys | Thr | Phe | Thr |
| 305 | | | | | 310 | | | | | 315 | | | | | 320 |

| Val | Thr | Glu | Lys | Pro | Glu | Val | Ile | Asp | Ala | Ser | Glu | Leu | Thr | Pro | Ala |
| | | | | 325 | | | | | 330 | | | | | 335 | |

| Val | Thr | Arg | Ser | Ala | Asp | Asn | Asn | Phe | Asn | Lys | Glu | Gln | Gln | Asn | Ala |
| | | | 340 | | | | | 345 | | | | | 350 | | |

| Phe | Tyr | Glu | Ile | Leu | Asn | Met | Pro | Asn | Leu | Asn | Glu | Glu | Gln | Arg | Asn |
| | | | 355 | | | | 360 | | | | | 365 | | | |

| Gly | Phe | Ile | Gln | Ser | Leu | Lys | Asp | Asp | Pro | Ser | Gln | Ser | Ala | Asn | Leu |
| | | 370 | | | | 375 | | | | | 380 | | | | |

| Leu | Ser | Glu | Ala | Lys | Lys | Leu | Asn | Glu | Ser | Gln | Ala | Pro | Lys | Asp | Arg |
| 385 | | | | | 390 | | | | | 395 | | | | | 400 |

| Ser | Ala |

( 2 ) INFORMATION FOR SEQ ID NO:18:

( i ) SEQUENCE CHARACTERISTICS:
        ( A ) LENGTH: 1683 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..1520

( x i ) SEQUENCE DESCRIPTION: SEQ ID NO:18:

```
TCCCTCTAGA TGCGGCCTAA TTAATTAAGC TTAAAAGGAG GAAAAAAATT ATG AAA        56
                                                        Met Lys
                                                         1
```

| AGA | ATA | GTG | CCA | AAG | TTC | ACT | GAA | ATC | TTC | CCC | GTG | GAG | GAC | GCG | AAC | 104 |
| Arg | Ile | Val | Pro | Lys | Phe | Thr | Glu | Ile | Phe | Pro | Val | Glu | Asp | Ala | Asn | |
| | | | 5 | | | | | 10 | | | | | 15 | | | |

| TAC | CCT | TAC | AGC | GCC | TTC | ATC | GCG | TCG | GTC | CGG | AAA | GAC | GTG | ATC | AAA | 152 |
| Tyr | Pro | Tyr | Ser | Ala | Phe | Ile | Ala | Ser | Val | Arg | Lys | Asp | Val | Ile | Lys | |
| | | 20 | | | | | 25 | | | | | 30 | | | | |

| CAC | TGC | ACC | GAC | CAT | AAA | GGG | ATC | TTC | CAG | CCC | GTG | CTG | CCA | CCG | GAG | 200 |
| His | Cys | Thr | Asp | His | Lys | Gly | Ile | Phe | Gln | Pro | Val | Leu | Pro | Pro | Glu | |
| 35 | | | | | 40 | | | | | 45 | | | | | 50 | |

| AAG | AAG | GTC | CCG | GAG | CTA | TGG | TTC | TAC | ACA | GAG | CTC | AAA | ACT | AGG | ACC | 248 |
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |

| AGC | TCC | ATC | ACG | CTC | GCC | ATA | CGC | ATG | GAC | AAC | CTG | TAC | CTC | GTG | GGC | 296 |
| Ser | Ser | Ile | Thr | Leu | Ala | Ile | Arg | Met | Asp | Asn | Leu | Tyr | Leu | Val | Gly | |
| | | | 70 | | | | | 75 | | | | | 80 | | | |

| TTC | AGG | ACC | CCG | GGC | GGG | GTG | TGG | TGG | GAG | TTC | GGC | AAG | GAC | GGC | GAC | 344 |
| Phe | Arg | Thr | Pro | Gly | Gly | Val | Trp | Trp | Glu | Phe | Gly | Lys | Asp | Gly | Asp | |
| | | 85 | | | | | 90 | | | | | 95 | | | | |

| ACC | CAC | CTC | CTC | GGC | GAC | AAC | CCC | AGG | TGG | CTC | GGC | TTC | GGC | GGC | AGG | 392 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Thr | His | Leu | Leu | Gly | Asp | Asn | Pro | Arg | Trp | Leu | Gly | Phe | Gly | Gly | Arg |      |
|     | 100 |     |     |     | 105 |     |     |     |     | 110 |     |     |     |     |     |      |
| TAC | CAG | GAC | CTC | ATC | GGC | AAC | AAG | GGT | CTG | GAG | ACC | GTC | ACC | ATG | GGC | 440  |
| Tyr | Gln | Asp | Leu | Ile | Gly | Asn | Lys | Gly | Leu | Glu | Thr | Val | Thr | Met | Gly |      |
| 115 |     |     |     |     | 120 |     |     |     |     | 125 |     |     |     |     | 130 |      |
| CGC | GCC | GAA | ATG | ACC | AGG | GCC | GTC | AAC | GAC | CTG | GCG | AAG | AAG | AAG | AAG | 488  |
| Arg | Ala | Glu | Met | Thr | Arg | Ala | Val | Asn | Asp | Leu | Ala | Lys | Lys | Lys | Lys |      |
|     |     |     |     | 135 |     |     |     |     | 140 |     |     |     |     | 145 |     |      |
| GCG | GCT | GAC | CCA | CAG | GCC | GAC | ACG | AAG | AGC | AAG | CTG | GTG | AAG | CTG | GTG | 536  |
| Ala | Ala | Asp | Pro | Gln | Ala | Asp | Thr | Lys | Ser | Lys | Leu | Val | Lys | Leu | Val |      |
|     |     |     | 150 |     |     |     |     | 155 |     |     |     |     | 160 |     |     |      |
| GTC | ATG | GTG | TGC | GAG | GGG | CTG | CGG | TTC | AAC | ACC | GTG | TCC | CGC | ACG | GTG | 584  |
| Val | Met | Val | Cys | Glu | Gly | Leu | Arg | Phe | Asn | Thr | Val | Ser | Arg | Thr | Val |      |
|     |     | 165 |     |     |     |     | 170 |     |     |     |     | 175 |     |     |     |      |
| GAC | GCG | GGG | TTC | AAC | AGC | CAG | CAC | GGG | GTG | ACC | TTG | ACC | GTG | ACG | CAG | 632  |
| Asp | Ala | Gly | Phe | Asn | Ser | Gln | His | Gly | Val | Thr | Leu | Thr | Val | Thr | Gln |      |
|     | 180 |     |     |     |     | 185 |     |     |     |     | 190 |     |     |     |     |      |
| GGG | AAG | CAG | GTG | CAG | AAG | TGG | GAC | AGG | ATC | TCC | AAG | GCG | GCC | TTC | GAG | 680  |
| Gly | Lys | Gln | Val | Gln | Lys | Trp | Asp | Arg | Ile | Ser | Lys | Ala | Ala | Phe | Glu |      |
| 195 |     |     |     |     | 200 |     |     |     |     | 205 |     |     |     |     | 210 |      |
| TGG | GCT | GAC | CAC | CCC | ACC | GCT | GTG | ATC | CCC | GAC | ATG | CAG | AAG | CTT | GGC | 728  |
| Trp | Ala | Asp | His | Pro | Thr | Ala | Val | Ile | Pro | Asp | Met | Gln | Lys | Leu | Gly |      |
|     |     |     | 215 |     |     |     |     | 220 |     |     |     |     | 225 |     |     |      |
| ATC | AAG | GAT | AAG | AAC | GAA | GCA | GCG | AGG | ATC | GTT | GCG | CTC | GTT | AAG | AAT | 776  |
| Ile | Lys | Asp | Lys | Asn | Glu | Ala | Ala | Arg | Ile | Val | Ala | Leu | Val | Lys | Asn |      |
|     |     |     | 230 |     |     |     |     | 235 |     |     |     |     | 240 |     |     |      |
| CAA | ACT | ACT | GCC | GCT | GCC | GCT | ACT | GCT | GGA | TCC | AAA | CCA | GAA | GTG | ATC | 824  |
| Gln | Thr | Thr | Ala | Ala | Ala | Ala | Thr | Ala | Gly | Ser | Lys | Pro | Glu | Val | Ile |      |
|     |     | 245 |     |     |     |     | 250 |     |     |     |     | 255 |     |     |     |      |
| GAT | GCG | TCT | GAA | TTA | ACA | CCA | GCC | GTG | ACA | ACT | TAC | AAA | CTT | GTT | ATT | 872  |
| Asp | Ala | Ser | Glu | Leu | Thr | Pro | Ala | Val | Thr | Thr | Tyr | Lys | Leu | Val | Ile |      |
|     | 260 |     |     |     |     | 265 |     |     |     |     | 270 |     |     |     |     |      |
| AAT | GGT | AAA | ACA | TTG | AAA | GGC | GAA | ACA | ACT | ACT | GAA | GCT | GTT | GAT | GCT | 920  |
| Asn | Gly | Lys | Thr | Leu | Lys | Gly | Glu | Thr | Thr | Thr | Glu | Ala | Val | Asp | Ala |      |
| 275 |     |     |     |     | 280 |     |     |     |     | 285 |     |     |     |     | 290 |      |
| GCT | ACT | GCA | GAA | AAA | GTC | TTC | AAA | CAA | TAC | GCT | AAC | GAC | AAC | GGT | GTT | 968  |
| Ala | Thr | Ala | Glu | Lys | Val | Phe | Lys | Gln | Tyr | Ala | Asn | Asp | Asn | Gly | Val |      |
|     |     |     |     | 295 |     |     |     |     | 300 |     |     |     |     | 305 |     |      |
| GAC | GGT | GAA | TGG | ACT | TAC | GAC | GAT | GCG | ACT | AAG | ACC | TTT | ACA | GTT | ACT | 1016 |
| Asp | Gly | Glu | Trp | Thr | Tyr | Asp | Asp | Ala | Thr | Lys | Thr | Phe | Thr | Val | Thr |      |
|     |     |     | 310 |     |     |     |     | 315 |     |     |     |     | 320 |     |     |      |
| GAA | AAA | CCA | GAA | GTG | ATC | GAT | GCG | TCT | GAA | TTA | ACA | CCA | GCC | GTG | ACA | 1064 |
| Glu | Lys | Pro | Glu | Val | Ile | Asp | Ala | Ser | Glu | Leu | Thr | Pro | Ala | Val | Thr |      |
|     |     | 325 |     |     |     |     | 330 |     |     |     |     | 335 |     |     |     |      |
| AGA | TCC | AAA | CCA | GAA | GTG | ATC | GAT | GCG | TCT | GAA | TTA | ACA | CCA | GCC | GTG | 1112 |
| Arg | Ser | Lys | Pro | Glu | Val | Ile | Asp | Ala | Ser | Glu | Leu | Thr | Pro | Ala | Val |      |
|     |     | 340 |     |     |     |     | 345 |     |     |     |     | 350 |     |     |     |      |
| ACA | ACT | TAC | AAA | CTT | GTT | ATT | AAT | GGT | AAA | ACA | TTG | AAA | GGC | GAA | ACA | 1160 |
| Thr | Thr | Tyr | Lys | Leu | Val | Ile | Asn | Gly | Lys | Thr | Leu | Lys | Gly | Glu | Thr |      |
| 355 |     |     |     |     | 360 |     |     |     |     | 365 |     |     |     |     | 370 |      |
| ACT | ACT | GAA | GCT | GTT | GAT | GCT | GCT | ACT | GCA | GAA | AAA | GTC | TTC | AAA | CAA | 1208 |
| Thr | Thr | Glu | Ala | Val | Asp | Ala | Ala | Thr | Ala | Glu | Lys | Val | Phe | Lys | Gln |      |
|     |     |     |     | 375 |     |     |     |     | 380 |     |     |     |     | 385 |     |      |
| TAC | GCT | AAC | GAC | AAC | GGT | GTT | GAC | GGT | GAA | TGG | ACT | TAC | GAC | GAT | GCG | 1256 |
| Tyr | Ala | Asn | Asp | Asn | Gly | Val | Asp | Gly | Glu | Trp | Thr | Tyr | Asp | Asp | Ala |      |
|     |     |     | 390 |     |     |     |     | 395 |     |     |     |     | 400 |     |     |      |
| ACT | AAG | ACC | TTT | ACA | GTT | ACT | GAA | AAA | CCA | GAA | GTG | ATC | GAT | GCG | TCT | 1304 |
| Thr | Lys | Thr | Phe | Thr | Val | Thr | Glu | Lys | Pro | Glu | Val | Ile | Asp | Ala | Ser |      |
|     |     | 405 |     |     |     |     | 410 |     |     |     |     | 415 |     |     |     |      |
| GAA | TTA | ACA | CCA | GCC | GTG | ACA | AGA | TCC | GCT | GAT | AAC | AAT | TTC | AAC | AAA | 1352 |

```
         Glu  Leu  Thr  Pro  Ala  Val  Thr  Arg  Ser  Ala  Asp  Asn  Asn  Phe  Asn  Lys
              420                 425                      430

GAA  CAA  CAA  AAT  GCT  TTC  TAT  GAA  ATC  TTG  AAT  ATG  CCT  AAC  TTA  AAC       1400
Glu  Gln  Gln  Asn  Ala  Phe  Tyr  Glu  Ile  Leu  Asn  Met  Pro  Asn  Leu  Asn
435                      440                      445                      450

GAA  GAA  CAA  CGC  AAT  GGT  TTC  ATC  CAA  AGC  TTA  AAA  GAT  GAC  CCA  AGC       1448
Glu  Glu  Gln  Arg  Asn  Gly  Phe  Ile  Gln  Ser  Leu  Lys  Asp  Asp  Pro  Ser
                    455                      460                      465

CAA  AGT  GCT  AAC  CTA  TTG  TCA  GAA  GCT  AAA  AAG  TTA  AAT  GAA  TCT  CAA       1496
Gln  Ser  Ala  Asn  Leu  Leu  Ser  Glu  Ala  Lys  Lys  Leu  Asn  Glu  Ser  Gln
               470                      475                      480

GCA  CCG  AAA  GAT  CGA  TCC  GCC  TGATCAATGC  AACGACACAT  CATGATCTGC                1547
Ala  Pro  Lys  Asp  Arg  Ser  Ala
          485                 490

TGCTGCACTT  AATTACTATG  TTCGTATACA  AATAAATACA  CCCGGCGTAC  GCGGTGTTCC               1607

TTATATGGTC  TAAAATGTAG  CCAGTAAATT  TTAAACTACT  TTCTCGTGCC  GAATTCACTG               1667

GCCGGCATGC  TATATA                                                                   1683
```

( 2 ) INFORMATION FOR SEQ ID NO:19:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Lys  Arg  Ile  Val  Pro  Lys  Phe  Thr  Glu  Ile  Phe  Pro  Val  Glu  Asp
 1                  5                    10                       15

Ala  Asn  Tyr  Pro  Tyr  Ser  Ala  Phe  Ile  Ala  Ser  Val  Arg  Lys  Asp  Val
               20                    25                       30

Ile  Lys  His  Cys  Thr  Asp  His  Lys  Gly  Ile  Phe  Gln  Pro  Val  Leu  Pro
               35                    40                       45

Pro  Glu  Lys  Lys  Val  Pro  Glu  Leu  Trp  Phe  Tyr  Thr  Glu  Leu  Lys  Thr
     50                    55                       60

Arg  Thr  Ser  Ser  Ile  Thr  Leu  Ala  Ile  Arg  Met  Asp  Asn  Leu  Tyr  Leu
 65                      70                    75                           80

Val  Gly  Phe  Arg  Thr  Pro  Gly  Gly  Val  Trp  Trp  Glu  Phe  Gly  Lys  Asp
                    85                    90                       95

Gly  Asp  Thr  His  Leu  Leu  Gly  Asp  Asn  Pro  Arg  Trp  Leu  Gly  Phe  Gly
                   100                   105                     110

Gly  Arg  Tyr  Gln  Asp  Leu  Ile  Gly  Asn  Lys  Gly  Leu  Glu  Thr  Val  Thr
               115                   120                     125

Met  Gly  Arg  Ala  Glu  Met  Thr  Arg  Ala  Val  Asn  Asp  Leu  Ala  Lys  Lys
     130                   135                   140

Lys  Lys  Ala  Ala  Asp  Pro  Gln  Ala  Asp  Thr  Lys  Ser  Lys  Leu  Val  Lys
145                      150                   155                          160

Leu  Val  Val  Met  Val  Cys  Glu  Gly  Leu  Arg  Phe  Asn  Thr  Val  Ser  Arg
                    165                   170                     175

Thr  Val  Asp  Ala  Gly  Phe  Asn  Ser  Gln  His  Gly  Val  Thr  Leu  Thr  Val
               180                   185                     190

Thr  Gln  Gly  Lys  Gln  Val  Gln  Lys  Trp  Asp  Arg  Ile  Ser  Lys  Ala  Ala
          195                   200                     205

Phe  Glu  Trp  Ala  Asp  His  Pro  Thr  Ala  Val  Ile  Pro  Asp  Met  Gln  Lys
     210                   215                     220

Leu  Gly  Ile  Lys  Asp  Lys  Asn  Glu  Ala  Ala  Arg  Ile  Val  Ala  Leu  Val
```

|     |     |     |     |     |     |     |     |     |     |     |     |     |     |     |
|---|---|---|---|---|---|---|---|---|---|---|---|---|---|---|
| 225 |     |     |     |     | 230 |     |     |     |     | 235 |     |     |     | 240 |
| Lys | Asn | Gln | Thr | Thr | Ala | Ala | Ala | Ala | Thr | Ala | Gly | Ser | Lys | Pro | Glu |
|     |     |     |     | 245 |     |     |     |     | 250 |     |     |     | 255 |
| Val | Ile | Asp | Ala | Ser | Glu | Leu | Thr | Pro | Ala | Val | Thr | Thr | Tyr | Lys | Leu |
|     |     |     | 260 |     |     |     | 265 |     |     |     | 270 |
| Val | Ile | Asn | Gly | Lys | Thr | Leu | Lys | Gly | Glu | Thr | Thr | Thr | Glu | Ala | Val |
|     |     | 275 |     |     |     | 280 |     |     |     | 285 |
| Asp | Ala | Ala | Thr | Ala | Glu | Lys | Val | Phe | Lys | Gln | Tyr | Ala | Asn | Asp | Asn |
|     | 290 |     |     |     | 295 |     |     |     | 300 |
| Gly | Val | Asp | Gly | Glu | Trp | Thr | Tyr | Asp | Asp | Ala | Thr | Lys | Thr | Phe | Thr |
| 305 |     |     |     | 310 |     |     |     | 315 |     |     |     | 320 |
| Val | Thr | Glu | Lys | Pro | Glu | Val | Ile | Asp | Ala | Ser | Glu | Leu | Thr | Pro | Ala |
|     |     |     | 325 |     |     |     | 330 |     |     |     | 335 |
| Val | Thr | Arg | Ser | Lys | Pro | Glu | Val | Ile | Asp | Ala | Ser | Glu | Leu | Thr | Pro |
|     |     | 340 |     |     |     | 345 |     |     |     | 350 |
| Ala | Val | Thr | Thr | Tyr | Lys | Leu | Val | Ile | Asn | Gly | Lys | Thr | Leu | Lys | Gly |
|     |     | 355 |     |     |     | 360 |     |     |     | 365 |
| Glu | Thr | Thr | Thr | Glu | Ala | Val | Asp | Ala | Ala | Thr | Ala | Glu | Lys | Val | Phe |
|     | 370 |     |     |     | 375 |     |     |     | 380 |
| Lys | Gln | Tyr | Ala | Asn | Asp | Asn | Gly | Val | Asp | Gly | Glu | Trp | Thr | Tyr | Asp |
| 385 |     |     |     | 390 |     |     |     | 395 |     |     |     | 400 |
| Asp | Ala | Thr | Lys | Thr | Phe | Thr | Val | Thr | Glu | Lys | Pro | Glu | Val | Ile | Asp |
|     |     |     | 405 |     |     |     | 410 |     |     |     | 415 |
| Ala | Ser | Glu | Leu | Thr | Pro | Ala | Val | Thr | Arg | Ser | Ala | Asp | Asn | Asn | Phe |
|     |     |     | 420 |     |     |     | 425 |     |     |     | 430 |
| Asn | Lys | Glu | Gln | Gln | Asn | Ala | Phe | Tyr | Glu | Ile | Leu | Asn | Met | Pro | Asn |
|     |     |     | 435 |     |     |     | 440 |     |     |     | 445 |
| Leu | Asn | Glu | Glu | Gln | Arg | Asn | Gly | Phe | Ile | Gln | Ser | Leu | Lys | Asp | Asp |
|     |     | 450 |     |     |     | 455 |     |     |     | 460 |
| Pro | Ser | Gln | Ser | Ala | Asn | Leu | Leu | Ser | Glu | Ala | Lys | Lys | Leu | Asn | Glu |
| 465 |     |     |     | 470 |     |     |     | 475 |     |     |     | 480 |
| Ser | Gln | Ala | Pro | Lys | Asp | Arg | Ser | Ala |
|     |     |     |     | 485 |

( 2 ) INFORMATION FOR SEQ ID NO:20:

( i ) SEQUENCE CHARACTERISTICS:
        ( A ) LENGTH: 847 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..845

( x i ) SEQUENCE DESCRIPTION: SEQ ID NO:20:

```
TCCCTCTAGA TGCGGCCTAA TTAATTAAGC TTAAAGGAG GAAAAAAATT ATG AAA      56
                                                    Met Lys
                                                      1

AGA ATA GTG CCA AAG TTC ACT GAA ATC TTC CCC GTG GAG GAC GCG AAC   104
Arg Ile Val Pro Lys Phe Thr Glu Ile Phe Pro Val Glu Asp Ala Asn
          5                  10                  15

TAC CCT TAC AGC GCC TTC ATC GCG TCG GTC CGG AAA GAC GTG ATC AAA   152
Tyr Pro Tyr Ser Ala Phe Ile Ala Ser Val Arg Lys Asp Val Ile Lys
     20                  25                  30

CAC TGC ACC GAC CAT AAA GGG ATC TTC CAG CCC GTG CTG CCA CCG GAG   200
His Cys Thr Asp His Lys Gly Ile Phe Gln Pro Val Leu Pro Pro Glu
 35                  40                  45                  50
```

| | | | | | | | | | | | | | | | | |
|---|---|---|---|---|---|---|---|---|---|---|---|---|---|---|---|---|
| AAG | AAG | GTC | CCG | GAG | CTA | TGG | TTC | TAC | ACA | GAG | CTC | AAA | ACT | AGG | ACC | 248 |
| Lys | Lys | Val | Pro | Glu | Leu | Trp | Phe | Tyr | Thr | Glu | Leu | Lys | Thr | Arg | Thr | |
| | | | | 55 | | | | 60 | | | | | | 65 | | |
| AGC | TCC | ATC | ACG | CTC | GCC | ATA | CGC | ATG | GAC | AAC | CTG | TAC | CTC | GTG | GGC | 296 |
| Ser | Ser | Ile | Thr | Leu | Ala | Ile | Arg | Met | Asp | Asn | Leu | Tyr | Leu | Val | Gly | |
| | | | 70 | | | | | 75 | | | | | 80 | | | |
| TTC | AGG | ACC | CCG | GGC | GGG | GTG | TGG | TGG | GAG | TTC | GGC | AAG | GAC | GGC | GAC | 344 |
| Phe | Arg | Thr | Pro | Gly | Gly | Val | Trp | Trp | Glu | Phe | Gly | Lys | Asp | Gly | Asp | |
| | | 85 | | | | | | 90 | | | | | 95 | | | |
| ACC | CAC | CTC | CTC | GGC | GAC | AAC | CCC | AGG | TGG | CTC | GGC | TTC | GGC | GGC | AGG | 392 |
| Thr | His | Leu | Leu | Gly | Asp | Asn | Pro | Arg | Trp | Leu | Gly | Phe | Gly | Gly | Arg | |
| | 100 | | | | | 105 | | | | | 110 | | | | | |
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | | 120 | | | | | 125 | | | | | 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| GCG | GCT | GAC | CCA | CAG | GCC | GAC | ACG | AAG | AGC | AAG | CTG | GTG | AAG | CTG | GTG | 536 |
| Ala | Ala | Asp | Pro | Gln | Ala | Asp | Thr | Lys | Ser | Lys | Leu | Val | Lys | Leu | Val | |
| | | | 150 | | | | | 155 | | | | | 160 | | | |
| GTC | ATG | GTG | TGC | GAG | GGG | CTG | CGG | TTC | AAC | ACC | GTG | TCC | CGC | ACG | GTG | 584 |
| Val | Met | Val | Cys | Glu | Gly | Leu | Arg | Phe | Asn | Thr | Val | Ser | Arg | Thr | Val | |
| | | 165 | | | | | 170 | | | | | 175 | | | | |
| GAC | GCG | GGG | TTC | AAC | AGC | CAG | CAC | GGG | GTG | ACC | TTG | ACC | GTG | ACG | CAG | 632 |
| Asp | Ala | Gly | Phe | Asn | Ser | Gln | His | Gly | Val | Thr | Leu | Thr | Val | Thr | Gln | |
| | 180 | | | | | 185 | | | | | 190 | | | | | |
| GGG | AAG | CAG | GTG | CAG | AAG | TGG | GAC | AGG | ATC | TCC | AAG | GCG | GCC | TTC | GAG | 680 |
| Gly | Lys | Gln | Val | Gln | Lys | Trp | Asp | Arg | Ile | Ser | Lys | Ala | Ala | Phe | Glu | |
| 195 | | | | | 200 | | | | | 205 | | | | | 210 | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro | Thr | Ala | Val | Ile | Pro | Asp | Met | Gln | Lys | Leu | Gly | |
| | | | 215 | | | | | 220 | | | | | 225 | | | |
| ATC | AAG | GAT | AAG | AAC | GAA | GCA | GCG | AGG | ATC | GTT | GCG | CTC | GTT | AAG | AAT | 776 |
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |
| CAA | ACT | ACT | GCC | GCT | GCC | GCT | ACT | GCT | GGA | TCC | GTT | AAC | GTC | GAC | GAA | 824 |
| Gln | Thr | Thr | Ala | Ala | Ala | Ala | Thr | Ala | Gly | Ser | Val | Asn | Val | Asp | Glu | |
| | | 245 | | | | | 250 | | | | | 255 | | | | |
| TTC | ACT | GGC | CGG | CAT | GCT | ATA | TA | | | | | | | | | 847 |
| Phe | Thr | Gly | Arg | His | Ala | Ile | | | | | | | | | | |
| | 260 | | | | | 265 | | | | | | | | | | |

( 2 ) INFORMATION FOR SEQ ID NO:21:

( i ) SEQUENCE CHARACTERISTICS:
        ( A ) LENGTH: 265 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Lys | Arg | Ile | Val | Pro | Lys | Phe | Thr | Glu | Ile | Phe | Pro | Val | Glu | Asp |
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | | 35 | | | | | 40 | | | | | 45 | | |
| Pro | Glu | Lys | Lys | Val | Pro | Glu | Leu | Trp | Phe | Tyr | Thr | Glu | Leu | Lys | Thr |
| | 50 | | | | | 55 | | | | | 60 | | | | |

```
Arg  Thr  Ser  Ser  Ile  Thr  Leu  Ala  Ile  Arg  Met  Asp  Asn  Leu  Tyr  Leu
 65                       70                       75                        80

Val  Gly  Phe  Arg  Thr  Pro  Gly  Gly  Val  Trp  Trp  Glu  Phe  Gly  Lys  Asp
                    85                       90                       95

Gly  Asp  Thr  His  Leu  Leu  Gly  Asp  Asn  Pro  Arg  Trp  Leu  Gly  Phe  Gly
               100                      105                      110

Gly  Arg  Tyr  Gln  Asp  Leu  Ile  Gly  Asn  Lys  Gly  Leu  Glu  Thr  Val  Thr
               115                      120                      125

Met  Gly  Arg  Ala  Glu  Met  Thr  Arg  Ala  Val  Asn  Asp  Leu  Ala  Lys  Lys
          130                      135                      140

Lys  Lys  Ala  Ala  Asp  Pro  Gln  Ala  Asp  Thr  Lys  Ser  Lys  Leu  Val  Lys
145                      150                      155                       160

Leu  Val  Val  Met  Val  Cys  Glu  Gly  Leu  Arg  Phe  Asn  Thr  Val  Ser  Arg
               165                      170                      175

Thr  Val  Asp  Ala  Gly  Phe  Asn  Ser  Gln  His  Gly  Val  Thr  Leu  Thr  Val
               180                      185                      190

Thr  Gln  Gly  Lys  Gln  Val  Gln  Lys  Trp  Asp  Arg  Ile  Ser  Lys  Ala  Ala
          195                      200                      205

Phe  Glu  Trp  Ala  Asp  His  Pro  Thr  Ala  Val  Ile  Pro  Asp  Met  Gln  Lys
     210                      215                      220

Leu  Gly  Ile  Lys  Asp  Lys  Asn  Glu  Ala  Ala  Arg  Ile  Val  Ala  Leu  Val
225                      230                      235                       240

Lys  Asn  Gln  Thr  Thr  Ala  Ala  Ala  Ala  Thr  Ala  Gly  Ser  Val  Asn  Val
               245                      250                      255

Asp  Glu  Phe  Thr  Gly  Arg  His  Ala  Ile
               260                      265
```

( 2 ) INFORMATION FOR SEQ ID NO:22:

( i ) SEQUENCE CHARACTERISTICS:
        ( A ) LENGTH: 1695 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..1532

( x i ) SEQUENCE DESCRIPTION: SEQ ID NO:22:

```
TCCCTCTAGA  TGCGGCCTAA  TTAATTAAGC  TTAAAAGGAG  GAAAAAAATT  ATG  AAA              56
                                                           Met  Lys
                                                            1

AGA  ATA  GTG  CCA  AAG  TTC  ACT  GAA  ATC  TTC  CCC  GTG  GAG  GAC  GCG  AAC    104
Arg  Ile  Val  Pro  Lys  Phe  Thr  Glu  Ile  Phe  Pro  Val  Glu  Asp  Ala  Asn
           5                        10                       15

TAC  CCT  TAC  AGC  GCC  TTC  ATC  GCG  TCG  GTC  CGG  AAA  GAC  GTG  ATC  AAA    152
Tyr  Pro  Tyr  Ser  Ala  Phe  Ile  Ala  Ser  Val  Arg  Lys  Asp  Val  Ile  Lys
           20                       25                       30

CAC  TGC  ACC  GAC  CAT  AAA  GGG  ATC  TTC  CAG  CCC  GTG  CTG  CCA  CCG  GAG    200
His  Cys  Thr  Asp  His  Lys  Gly  Ile  Phe  Gln  Pro  Val  Leu  Pro  Pro  Glu
 35                       40                       45                        50

AAG  AAG  GTC  CCG  GAG  CTA  TGG  TTC  TAC  ACA  GAG  CTC  AAA  ACT  AGG  ACC    248
Lys  Lys  Val  Pro  Glu  Leu  Trp  Phe  Tyr  Thr  Glu  Leu  Lys  Thr  Arg  Thr
               55                       60                       65

AGC  TCC  ATC  ACG  CTC  GCC  ATA  CGC  ATG  GAC  AAC  CTG  TAC  CTC  GTG  GGC    296
Ser  Ser  Ile  Thr  Leu  Ala  Ile  Arg  Met  Asp  Asn  Leu  Tyr  Leu  Val  Gly
               70                       75                       80

TTC  AGG  ACC  CCG  GGC  GGG  GTG  TGG  TGG  GAG  TTC  GGC  AAG  GAC  GGC  GAC    344
```

| | | | | | | | | | | | | | | | | |
|---|---|---|---|---|---|---|---|---|---|---|---|---|---|---|---|---|
| Phe | Arg | Thr | Pro | Gly | Gly | Val | Trp | Trp | Glu | Phe | Gly | Lys | Asp | Gly | Asp | |
| | | 85 | | | | | | 90 | | | | 95 | | | | |
| ACC | CAC | CTC | CTC | GGC | GAC | AAC | CCC | AGG | TGG | CTC | GGC | TTC | GGC | GGC | AGG | 392 |
| Thr | His | Leu | Leu | Gly | Asp | Asn | Pro | Arg | Trp | Leu | Gly | Phe | Gly | Gly | Arg | |
| | 100 | | | | | 105 | | | | | 110 | | | | | |
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | | 120 | | | | | 125 | | | | | 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| GCG | GCT | GAC | CCA | CAG | GCC | GAC | ACG | AAG | AGC | AAG | CTG | GTG | AAG | CTG | GTG | 536 |
| Ala | Ala | Asp | Pro | Gln | Ala | Asp | Thr | Lys | Ser | Lys | Leu | Val | Lys | Leu | Val | |
| | | | 150 | | | | | 155 | | | | | 160 | | | |
| GTC | ATG | GTG | TGC | GAG | GGG | CTG | CGG | TTC | AAC | ACC | GTG | TCC | CGC | ACG | GTG | 584 |
| Val | Met | Val | Cys | Glu | Gly | Leu | Arg | Phe | Asn | Thr | Val | Ser | Arg | Thr | Val | |
| | | 165 | | | | | | 170 | | | | | 175 | | | |
| GAC | GCG | GGG | TTC | AAC | AGC | CAG | CAC | GGG | GTG | ACC | TTG | ACC | GTG | ACG | CAG | 632 |
| Asp | Ala | Gly | Phe | Asn | Ser | Gln | His | Gly | Val | Thr | Leu | Thr | Val | Thr | Gln | |
| | 180 | | | | | 185 | | | | | 190 | | | | | |
| GGG | AAG | CAG | GTG | CAG | AAG | TGG | GAC | AGG | ATC | TCC | AAG | GCG | GCC | TTC | GAG | 680 |
| Gly | Lys | Gln | Val | Gln | Lys | Trp | Asp | Arg | Ile | Ser | Lys | Ala | Ala | Phe | Glu | |
| 195 | | | | | 200 | | | | | 205 | | | | | 210 | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro | Thr | Ala | Val | Ile | Pro | Asp | Met | Gln | Lys | Leu | Gly | |
| | | | | 215 | | | | | 220 | | | | | 225 | | |
| ATC | AAG | GAT | AAG | AAC | GAA | GCA | GCG | AGG | ATC | GTT | GCG | CTC | GTT | AAG | AAT | 776 |
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |
| CAA | ACT | ACT | GCC | GCT | GCC | GCT | ACT | GCT | GGA | TCC | GTT | AAC | GTC | GAC | AAA | 824 |
| Gln | Thr | Thr | Ala | Ala | Ala | Ala | Thr | Ala | Gly | Ser | Val | Asn | Val | Asp | Lys | |
| | | 245 | | | | | 250 | | | | | 255 | | | | |
| CCA | GAA | GTG | ATC | GAT | GCG | TCT | GAA | TTA | ACA | CCA | GCC | GTG | ACA | ACT | TAC | 872 |
| Pro | Glu | Val | Ile | Asp | Ala | Ser | Glu | Leu | Thr | Pro | Ala | Val | Thr | Thr | Tyr | |
| | 260 | | | | | 265 | | | | | 270 | | | | | |
| AAA | CTT | GTT | ATT | AAT | GGT | AAA | ACA | TTG | AAA | GGC | GAA | ACA | ACT | ACT | GAA | 920 |
| Lys | Leu | Val | Ile | Asn | Gly | Lys | Thr | Leu | Lys | Gly | Glu | Thr | Thr | Thr | Glu | |
| 275 | | | | | 280 | | | | | 285 | | | | | 290 | |
| GCT | GTT | GAT | GCT | GCT | ACT | GCA | GAA | AAA | GTC | TTC | AAA | CAA | TAC | GCT | AAC | 968 |
| Ala | Val | Asp | Ala | Ala | Thr | Ala | Glu | Lys | Val | Phe | Lys | Gln | Tyr | Ala | Asn | |
| | | | | 295 | | | | | 300 | | | | | 305 | | |
| GAC | AAC | GGT | GTT | GAC | GGT | GAA | TGG | ACT | TAC | GAC | GAT | GCG | ACT | AAG | ACC | 1016 |
| Asp | Asn | Gly | Val | Asp | Gly | Glu | Trp | Thr | Tyr | Asp | Asp | Ala | Thr | Lys | Thr | |
| | | | 310 | | | | | 315 | | | | | 320 | | | |
| TTT | ACA | GTT | ACT | GAA | AAA | CCA | GAA | GTG | ATC | GAT | GCG | TCT | GAA | TTA | ACA | 1064 |
| Phe | Thr | Val | Thr | Glu | Lys | Pro | Glu | Val | Ile | Asp | Ala | Ser | Glu | Leu | Thr | |
| | | 325 | | | | | 330 | | | | | 335 | | | | |
| CCA | GCC | GTG | ACA | AGA | TCC | AAA | CCA | GAA | GTG | ATC | GAT | GCG | TCT | GAA | TTA | 1112 |
| Pro | Ala | Val | Thr | Arg | Ser | Lys | Pro | Glu | Val | Ile | Asp | Ala | Ser | Glu | Leu | |
| | 340 | | | | | 345 | | | | | 350 | | | | | |
| ACA | CCA | GCC | GTG | ACA | ACT | TAC | AAA | CTT | GTT | ATT | AAT | GGT | AAA | ACA | TTG | 1160 |
| Thr | Pro | Ala | Val | Thr | Thr | Tyr | Lys | Leu | Val | Ile | Asn | Gly | Lys | Thr | Leu | |
| 355 | | | | | 360 | | | | | 365 | | | | | 370 | |
| AAA | GGC | GAA | ACA | ACT | ACT | GAA | GCT | GTT | GAT | GCT | GCT | ACT | GCA | GAA | AAA | 1208 |
| Lys | Gly | Glu | Thr | Thr | Thr | Glu | Ala | Val | Asp | Ala | Ala | Thr | Ala | Glu | Lys | |
| | | | | 375 | | | | | 380 | | | | | 385 | | |
| GTC | TTC | AAA | CAA | TAC | GCT | AAC | GAC | AAC | GGT | GTT | GAC | GGT | GAA | TGG | ACT | 1256 |
| Val | Phe | Lys | Gln | Tyr | Ala | Asn | Asp | Asn | Gly | Val | Asp | Gly | Glu | Trp | Thr | |
| | | | 390 | | | | | 395 | | | | | 400 | | | |
| TAC | GAC | GAT | GCG | ACT | AAG | ACC | TTT | ACA | GTT | ACT | GAA | AAA | CCA | GAA | GTG | 1304 |

|                |                |                |                |                |                |                |                |                |                |                |                |                |                |                |                |      |
|---|---|---|---|---|---|---|---|---|---|---|---|---|---|---|---|---|
| Tyr            | Asp            | Asp<br>405     | Ala            | Thr            | Lys            | Thr            | Phe<br>410     | Thr            | Val            | Thr            | Glu            | Lys<br>415     | Pro            | Glu            | Val            |      |
| ATC<br>Ile     | GAT<br>Asp<br>420 | GCG<br>Ala  | TCT<br>Ser     | GAA<br>Glu     | TTA<br>Leu     | ACA<br>Thr<br>425 | CCA<br>Pro  | GCC<br>Ala     | GTG<br>Val     | ACA<br>Thr     | AGA<br>Arg<br>430 | TCC<br>Ser  | GCT<br>Ala     | GAT<br>Asp     | AAC<br>Asn     | 1352 |
| AAT<br>Asn<br>435 | TTC<br>Phe  | AAC<br>Asn     | AAA<br>Lys     | GAA<br>Glu     | CAA<br>Gln<br>440 | CAA<br>Gln  | AAT<br>Asn     | GCT<br>Ala     | TTC<br>Phe     | TAT<br>Tyr<br>445 | GAA<br>Glu  | ATC<br>Ile     | TTG<br>Leu     | AAT<br>Asn     | ATG<br>Met<br>450 | 1400 |
| CCT<br>Pro     | AAC<br>Asn     | TTA<br>Leu     | AAC<br>Asn     | GAA<br>Glu<br>455 | GAA<br>Glu  | CAA<br>Gln     | CGC<br>Arg     | AAT<br>Asn     | GGT<br>Gly<br>460 | TTC<br>Phe  | ATC<br>Ile     | CAA<br>Gln     | AGC<br>Ser     | TTA<br>Leu<br>465 | AAA<br>Lys  | 1448 |
| GAT<br>Asp     | GAC<br>Asp     | CCA<br>Pro<br>470 | AGC<br>Ser  | CAA<br>Gln     | AGT<br>Ser     | GCT<br>Ala     | AAC<br>Asn     | CTA<br>Leu<br>475 | TTG<br>Leu  | TCA<br>Ser     | GAA<br>Glu     | GCT<br>Ala     | AAA<br>Lys<br>480 | AAG<br>Lys  | TTA<br>Leu     | 1496 |
| AAT<br>Asn     | GAA<br>Glu     | TCT<br>Ser<br>485 | CAA<br>Gln  | GCA<br>Ala     | CCG<br>Pro     | AAA<br>Lys     | GAT<br>Asp<br>490 | CGA<br>Arg  | TCC<br>Ser     | GCC<br>Ala     | TGATCAATGC     | AACGACACAT     |                |                |                | 1549 |
| CATGATCTGC | TGCTGCACTT | AATTACTATG | TTCGTATACA | AATAAATACA | CCCGGCGTAC | | | | | | | | | | | 1609 |
| GCGGTGTTCC | TTATATGGTC | TAAAATGTAG | CCAGTAAATT | TTAAACTACT | TTCTCGTGCC | | | | | | | | | | | 1669 |
| GAATTCACTG | GCCGGCATGC | TATATA | | | | | | | | | | | | | | 1695 |

( 2 ) INFORMATION FOR SEQ ID NO:23:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| Met<br>1 | Lys | Arg | Ile | Val<br>5 | Pro | Lys | Phe | Thr | Glu<br>10 | Ile | Phe | Pro | Val | Asp<br>15 |
|---|---|---|---|---|---|---|---|---|---|---|---|---|---|---|
| Ala | Asn | Tyr | Pro<br>20 | Tyr | Ser | Ala | Phe | Ile<br>25 | Ala | Ser | Val | Arg | Lys<br>30 | Asp | Val |
| Ile | Lys | His<br>35 | Cys | Thr | Asp | His | Lys<br>40 | Gly | Ile | Phe | Gln | Pro<br>45 | Val | Leu | Pro |
| Pro | Glu<br>50 | Lys | Lys | Val | Pro<br>55 | Glu | Leu | Trp | Phe | Tyr<br>60 | Thr | Glu | Leu | Lys | Thr |
| Arg<br>65 | Thr | Ser | Ser | Ile | Thr<br>70 | Leu | Ala | Ile | Arg | Met<br>75 | Asp | Asn | Leu | Tyr | Leu<br>80 |
| Val | Gly | Phe | Arg | Thr<br>85 | Pro | Gly | Gly | Val | Trp<br>90 | Trp | Glu | Phe | Gly | Lys<br>95 | Asp |
| Gly | Asp | Thr | His<br>100 | Leu | Leu | Gly | Asp | Asn<br>105 | Pro | Arg | Trp | Leu | Gly<br>110 | Phe | Gly |
| Gly | Arg | Tyr<br>115 | Gln | Asp | Leu | Ile | Gly<br>120 | Asn | Lys | Gly | Leu | Glu<br>125 | Thr | Val | Thr |
| Met | Gly<br>130 | Arg | Ala | Glu | Met | Thr<br>135 | Arg | Ala | Val | Asn | Asp<br>140 | Leu | Ala | Lys | Lys |
| Lys<br>145 | Lys | Ala | Ala | Asp | Pro<br>150 | Gln | Ala | Asp | Thr | Lys<br>155 | Ser | Lys | Leu | Val | Lys<br>160 |
| Leu | Val | Val | Met | Val<br>165 | Cys | Glu | Gly | Leu | Arg<br>170 | Phe | Asn | Thr | Val | Ser<br>175 | Arg |
| Thr | Val | Asp | Ala<br>180 | Gly | Phe | Asn | Ser | Gln<br>185 | His | Gly | Val | Thr | Leu<br>190 | Thr | Val |
| Thr | Gln | Gly<br>195 | Lys | Gln | Val | Gln | Lys<br>200 | Trp | Asp | Arg | Ile | Ser<br>205 | Lys | Ala | Ala |

-continued

```
Phe Glu Trp Ala Asp His Pro Thr Ala Val Ile Pro Asp Met Gln Lys
    210                 215                 220
Leu Gly Ile Lys Asp Lys Asn Glu Ala Ala Arg Ile Val Ala Leu Val
225                 230                 235                 240
Lys Asn Gln Thr Thr Ala Ala Ala Ala Thr Ala Gly Ser Val Asn Val
                245                 250                 255
Asp Lys Pro Glu Val Ile Asp Ala Ser Glu Leu Thr Pro Ala Val Thr
                260                 265                 270
Thr Tyr Lys Leu Val Ile Asn Gly Lys Thr Leu Lys Gly Glu Thr Thr
            275                 280                 285
Thr Glu Ala Val Asp Ala Ala Thr Ala Glu Lys Val Phe Lys Gln Tyr
    290                 295                 300
Ala Asn Asp Asn Gly Val Asp Gly Glu Trp Thr Tyr Asp Asp Ala Thr
305                 310                 315                 320
Lys Thr Phe Thr Val Thr Glu Lys Pro Glu Val Ile Asp Ala Ser Glu
                325                 330                 335
Leu Thr Pro Ala Val Thr Arg Ser Lys Pro Glu Val Ile Asp Ala Ser
                340                 345                 350
Glu Leu Thr Pro Ala Val Thr Thr Tyr Lys Leu Val Ile Asn Gly Lys
            355                 360                 365
Thr Leu Lys Gly Glu Thr Thr Thr Glu Ala Val Asp Ala Ala Thr Ala
    370                 375                 380
Glu Lys Val Phe Lys Gln Tyr Ala Asn Asp Asn Gly Val Asp Gly Glu
385                 390                 395                 400
Trp Thr Tyr Asp Asp Ala Thr Lys Thr Phe Thr Val Thr Glu Lys Pro
                405                 410                 415
Glu Val Ile Asp Ala Ser Glu Leu Thr Pro Ala Val Thr Arg Ser Ala
                420                 425                 430
Asp Asn Asn Phe Asn Lys Glu Gln Gln Asn Ala Phe Tyr Glu Ile Leu
            435                 440                 445
Asn Met Pro Asn Leu Asn Glu Glu Gln Arg Asn Gly Phe Ile Gln Ser
    450                 455                 460
Leu Lys Asp Asp Pro Ser Gln Ser Ala Asn Leu Leu Ser Glu Ala Lys
465                 470                 475                 480
Lys Leu Asn Glu Ser Gln Ala Pro Lys Asp Arg Ser Ala
                485                 490
```

( 2 ) INFORMATION FOR SEQ ID NO:24:

( i ) SEQUENCE CHARACTERISTICS:
        ( A ) LENGTH: 1722 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 51..1559

( x i ) SEQUENCE DESCRIPTION: SEQ ID NO:24:

```
TCCCTCTAGA TGCGGCCTAA TTAATTAAGC TTAAAAGGAG GAAAAAAATT ATG AAA        56
                                                      Met Lys
                                                        1

AGA ATA GTG CCA AAG TTC ACT GAA ATC TTC CCC GTG GAG GAC GCG AAC     104
Arg Ile Val Pro Lys Phe Thr Glu Ile Phe Pro Val Glu Asp Ala Asn
        5                  10                  15

TAC CCT TAC AGC GCC TTC ATC GCG TCG GTC CGG AAA GAC GTG ATC AAA     152
Tyr Pro Tyr Ser Ala Phe Ile Ala Ser Val Arg Lys Asp Val Ile Lys
    20                  25                  30
```

| | | | | | | | | | | | | | | | | |
|---|---|---|---|---|---|---|---|---|---|---|---|---|---|---|---|---|
| CAC | TGC | ACC | GAC | CAT | AAA | GGG | ATC | TTC | CAG | CCC | GTG | CTG | CCA | CCG | GAG | 200 |
| His | Cys | Thr | Asp | His | Lys | Gly | Ile | Phe | Gln | Pro | Val | Leu | Pro | Pro | Glu | |
| 35 | | | | 40 | | | | | 45 | | | | | | 50 | |
| AAG | AAG | GTC | CCG | GAG | CTA | TGG | TTC | TAC | ACA | GAG | CTC | AAA | ACT | AGG | ACC | 248 |
| Lys | Lys | Val | Pro | Glu | Leu | Trp | Phe | Tyr | Thr | Glu | Leu | Lys | Thr | Arg | Thr | |
| | | | | 55 | | | | | 60 | | | | | 65 | | |
| AGC | TCC | ATC | ACG | CTC | GCC | ATA | CGC | ATG | GAC | AAC | CTG | TAC | CTC | GTG | GGC | 296 |
| Ser | Ser | Ile | Thr | Leu | Ala | Ile | Arg | Met | Asp | Asn | Leu | Tyr | Leu | Val | Gly | |
| | | | 70 | | | | | 75 | | | | | | 80 | | |
| TTC | AGG | ACC | CCG | GGC | GGG | GTG | TGG | TGG | GAG | TTC | GGC | AAG | GAC | GGC | GAC | 344 |
| Phe | Arg | Thr | Pro | Gly | Gly | Val | Trp | Trp | Glu | Phe | Gly | Lys | Asp | Gly | Asp | |
| | | 85 | | | | | | 90 | | | | | 95 | | | |
| ACC | CAC | CTC | CTC | GGC | GAC | AAC | CCC | AGG | TGG | CTC | GGC | TTC | GGC | GGC | AGG | 392 |
| Thr | His | Leu | Leu | Gly | Asp | Asn | Pro | Arg | Trp | Leu | Gly | Phe | Gly | Gly | Arg | |
| | 100 | | | | | 105 | | | | | 110 | | | | | |
| TAC | CAG | GAC | CTC | ATC | GGC | AAC | AAG | GGT | CTG | GAG | ACC | GTC | ACC | ATG | GGC | 440 |
| Tyr | Gln | Asp | Leu | Ile | Gly | Asn | Lys | Gly | Leu | Glu | Thr | Val | Thr | Met | Gly | |
| 115 | | | | | 120 | | | | | 125 | | | | | 130 | |
| CGC | GCC | GAA | ATG | ACC | AGG | GCC | GTC | AAC | GAC | CTG | GCG | AAG | AAG | AAG | AAG | 488 |
| Arg | Ala | Glu | Met | Thr | Arg | Ala | Val | Asn | Asp | Leu | Ala | Lys | Lys | Lys | Lys | |
| | | | | 135 | | | | | 140 | | | | | 145 | | |
| GCG | GCT | GAC | CCA | CAG | GCC | GAC | ACG | AAG | AGC | AAG | CTG | GTG | AAG | CTG | GTG | 536 |
| Ala | Ala | Asp | Pro | Gln | Ala | Asp | Thr | Lys | Ser | Lys | Leu | Val | Lys | Leu | Val | |
| | | | 150 | | | | | 155 | | | | | 160 | | | |
| GTC | ATG | GTG | TGC | GAG | GGG | CTG | CGG | TTC | AAC | ACC | GTG | TCC | CGC | ACG | GTG | 584 |
| Val | Met | Val | Cys | Glu | Gly | Leu | Arg | Phe | Asn | Thr | Val | Ser | Arg | Thr | Val | |
| | | 165 | | | | | 170 | | | | | 175 | | | | |
| GAC | GCG | GGG | TTC | AAC | AGC | CAG | CAC | GGG | GTG | ACC | TTG | ACC | GTG | ACG | CAG | 632 |
| Asp | Ala | Gly | Phe | Asn | Ser | Gln | His | Gly | Val | Thr | Leu | Thr | Val | Thr | Gln | |
| | 180 | | | | | 185 | | | | | 190 | | | | | |
| GGG | AAG | CAG | GTG | CAG | AAG | TGG | GAC | AGG | ATC | TCC | AAG | GCG | GCC | TTC | GAG | 680 |
| Gly | Lys | Gln | Val | Gln | Lys | Trp | Asp | Arg | Ile | Ser | Lys | Ala | Ala | Phe | Glu | |
| 195 | | | | 200 | | | | | 205 | | | | | 210 | | |
| TGG | GCT | GAC | CAC | CCC | ACC | GCT | GTG | ATC | CCC | GAC | ATG | CAG | AAG | CTT | GGC | 728 |
| Trp | Ala | Asp | His | Pro | Thr | Ala | Val | Ile | Pro | Asp | Met | Gln | Lys | Leu | Gly | |
| | | | 215 | | | | | 220 | | | | | 225 | | | |
| ATC | AAG | GAT | AAG | AAC | GAA | GCA | GCG | AGG | ATC | GTT | GCG | CTC | GTT | AAG | AAT | 776 |
| Ile | Lys | Asp | Lys | Asn | Glu | Ala | Ala | Arg | Ile | Val | Ala | Leu | Val | Lys | Asn | |
| | | | 230 | | | | | 235 | | | | | 240 | | | |
| CAA | ACT | ACT | GCC | GCT | GCC | GCT | ACT | GCT | GGA | TCC | TCT | TGC | GCT | CGT | GTC | 824 |
| Gln | Thr | Thr | Ala | Ala | Ala | Ala | Thr | Ala | Gly | Ser | Ser | Cys | Ala | Arg | Val | |
| | | 245 | | | | | 250 | | | | | 255 | | | | |
| CGT | CGT | TCG | AGC | TGC | GGT | GTC | GAC | AAA | CCA | GAA | GTG | ATC | GAT | GCG | TCT | 872 |
| Arg | Arg | Ser | Ser | Cys | Gly | Val | Asp | Lys | Pro | Glu | Val | Ile | Asp | Ala | Ser | |
| | 260 | | | | | 265 | | | | | 270 | | | | | |
| GAA | TTA | ACA | CCA | GCC | GTG | ACA | ACT | TAC | AAA | CTT | GTT | ATT | AAT | GGT | AAA | 920 |
| Glu | Leu | Thr | Pro | Ala | Val | Thr | Thr | Tyr | Lys | Leu | Val | Ile | Asn | Gly | Lys | |
| 275 | | | | 280 | | | | | 285 | | | | | 290 | | |
| ACA | TTG | AAA | GGC | GAA | ACA | ACT | ACT | GAA | GCT | GTT | GAT | GCT | GCT | ACT | GCA | 968 |
| Thr | Leu | Lys | Gly | Glu | Thr | Thr | Thr | Glu | Ala | Val | Asp | Ala | Ala | Thr | Ala | |
| | | | | 295 | | | | | 300 | | | | | 305 | | |
| GAA | AAA | GTC | TTC | AAA | CAA | TAC | GCT | AAC | GAC | AAC | GGT | GTT | GAC | GGT | GAA | 1016 |
| Glu | Lys | Val | Phe | Lys | Gln | Tyr | Ala | Asn | Asp | Asn | Gly | Val | Asp | Gly | Glu | |
| | | | 310 | | | | | 315 | | | | | 320 | | | |
| TGG | ACT | TAC | GAC | GAT | GCG | ACT | AAG | ACC | TTT | ACA | GTT | ACT | GAA | AAA | CCA | 1064 |
| Trp | Thr | Tyr | Asp | Asp | Ala | Thr | Lys | Thr | Phe | Thr | Val | Thr | Glu | Lys | Pro | |
| | | 325 | | | | | 330 | | | | | 335 | | | | |
| GAA | GTG | ATC | GAT | GCG | TCT | GAA | TTA | ACA | CCA | GCC | GTG | ACA | AGA | TCC | AAA | 1112 |
| Glu | Val | Ile | Asp | Ala | Ser | Glu | Leu | Thr | Pro | Ala | Val | Thr | Arg | Ser | Lys | |
| | | | 340 | | | | | 345 | | | | | 350 | | | |

-continued

| | | | | | | | | | | | | | | | | |
|---|---|---|---|---|---|---|---|---|---|---|---|---|---|---|---|---|
| CCA | GAA | GTG | ATC | GAT | GCG | TCT | GAA | TTA | ACA | CCA | GCC | GTG | ACA | ACT | TAC | 1160 |
| Pro | Glu | Val | Ile | Asp | Ala | Ser | Glu | Leu | Thr | Pro | Ala | Val | Thr | Thr | Tyr | |
| 355 | | | | 360 | | | | | 365 | | | | | 370 | | |
| AAA | CTT | GTT | ATT | AAT | GGT | AAA | ACA | TTG | AAA | GGC | GAA | ACA | ACT | ACT | GAA | 1208 |
| Lys | Leu | Val | Ile | Asn | Gly | Lys | Thr | Leu | Lys | Gly | Glu | Thr | Thr | Thr | Glu | |
| | | | | 375 | | | | | 380 | | | | | 385 | | |
| GCT | GTT | GAT | GCT | GCT | ACT | GCA | GAA | AAA | GTC | TTC | AAA | CAA | TAC | GCT | AAC | 1256 |
| Ala | Val | Asp | Ala | Ala | Thr | Ala | Glu | Lys | Val | Phe | Lys | Gln | Tyr | Ala | Asn | |
| | | | 390 | | | | | 395 | | | | | 400 | | | |
| GAC | AAC | GGT | GTT | GAC | GGT | GAA | TGG | ACT | TAC | GAC | GAT | GCG | ACT | AAG | ACC | 1304 |
| Asp | Asn | Gly | Val | Asp | Gly | Glu | Trp | Thr | Tyr | Asp | Asp | Ala | Thr | Lys | Thr | |
| | | 405 | | | | | 410 | | | | | 415 | | | | |
| TTT | ACA | GTT | ACT | GAA | AAA | CCA | GAA | GTG | ATC | GAT | GCG | TCT | GAA | TTA | ACA | 1352 |
| Phe | Thr | Val | Thr | Glu | Lys | Pro | Glu | Val | Ile | Asp | Ala | Ser | Glu | Leu | Thr | |
| | 420 | | | | | 425 | | | | | 430 | | | | | |
| CCA | GCC | GTG | ACA | AGA | TCC | GCT | GAT | AAC | AAT | TTC | AAC | AAA | GAA | CAA | CAA | 1400 |
| Pro | Ala | Val | Thr | Arg | Ser | Ala | Asp | Asn | Asn | Phe | Asn | Lys | Glu | Gln | Gln | |
| 435 | | | | 440 | | | | | 445 | | | | | 450 | | |
| AAT | GCT | TTC | TAT | GAA | ATC | TTG | AAT | ATG | CCT | AAC | TTA | AAC | GAA | GAA | CAA | 1448 |
| Asn | Ala | Phe | Tyr | Glu | Ile | Leu | Asn | Met | Pro | Asn | Leu | Asn | Glu | Glu | Gln | |
| | | | | 455 | | | | | 460 | | | | | 465 | | |
| CGC | AAT | GGT | TTC | ATC | CAA | AGC | TTA | AAA | GAT | GAC | CCA | AGC | CAA | AGT | GCT | 1496 |
| Arg | Asn | Gly | Phe | Ile | Gln | Ser | Leu | Lys | Asp | Asp | Pro | Ser | Gln | Ser | Ala | |
| | | | 470 | | | | | 475 | | | | | 480 | | | |
| AAC | CTA | TTG | TCA | GAA | GCT | AAA | AAG | TTA | AAT | GAA | TCT | CAA | GCA | CCG | AAA | 1544 |
| Asn | Leu | Leu | Ser | Glu | Ala | Lys | Lys | Leu | Asn | Glu | Ser | Gln | Ala | Pro | Lys | |
| | | 485 | | | | | 490 | | | | | 495 | | | | |
| GAT | CGA | TCC | GCC | TGATCAATGC | | AACGACACAT | | CATGATCTGC | | TGCTGCACTT | | | | | | 1596 |
| Asp | Arg | Ser | Ala | | | | | | | | | | | | | |
| | | 500 | | | | | | | | | | | | | | |

AATTACTATG TTCGTATACA AATAAATACA CCCGGCGTAC GCGGTGTTCC TTATATGGTC        1656

TAAAATGTAG CCAGTAAATT TTAAACTACT TTCTCGTGCC GAATTCACTG GCCGGCATGC        1716

TATATA        1722

( 2 ) INFORMATION FOR SEQ ID NO:25:

( i ) SEQUENCE CHARACTERISTICS:
        ( A ) LENGTH: 502 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Lys | Arg | Ile | Val | Pro | Lys | Phe | Thr | Glu | Ile | Phe | Pro | Val | Glu | Asp |
| 1 | | | | 5 | | | | | 10 | | | | | 15 | |
| Ala | Asn | Tyr | Pro | Tyr | Ser | Ala | Phe | Ile | Ala | Ser | Val | Arg | Lys | Asp | Val |
| | | | 20 | | | | | 25 | | | | | 30 | | |
| Ile | Lys | His | Cys | Thr | Asp | His | Lys | Gly | Ile | Phe | Gln | Pro | Val | Leu | Pro |
| | | | 35 | | | | 40 | | | | | 45 | | | |
| Pro | Glu | Lys | Lys | Val | Pro | Glu | Leu | Trp | Phe | Tyr | Thr | Glu | Leu | Lys | Thr |
| | 50 | | | | | 55 | | | | | 60 | | | | |
| Arg | Thr | Ser | Ser | Ile | Thr | Leu | Ala | Ile | Arg | Met | Asp | Asn | Leu | Tyr | Leu |
| 65 | | | | | 70 | | | | | 75 | | | | | 80 |
| Val | Gly | Phe | Arg | Thr | Pro | Gly | Gly | Val | Trp | Trp | Glu | Phe | Gly | Lys | Asp |
| | | | | 85 | | | | | 90 | | | | | 95 | |
| Gly | Asp | Thr | His | Leu | Leu | Gly | Asp | Asn | Pro | Arg | Trp | Leu | Gly | Phe | Gly |
| | | | 100 | | | | | 105 | | | | | 110 | | |

```
Gly Arg Tyr Gln Asp Leu Ile Gly Asn Lys Gly Leu Glu Thr Val Thr
        115                 120                 125

Met Gly Arg Ala Glu Met Thr Arg Ala Val Asn Asp Leu Ala Lys Lys
130                 135                 140

Lys Lys Ala Ala Asp Pro Gln Ala Asp Thr Lys Ser Lys Leu Val Lys
145                 150                 155                 160

Leu Val Val Met Val Cys Glu Gly Leu Arg Phe Asn Thr Val Ser Arg
                165                 170                 175

Thr Val Asp Ala Gly Phe Asn Ser Gln His Gly Val Thr Leu Thr Val
            180                 185                 190

Thr Gln Gly Lys Gln Val Gln Lys Trp Asp Arg Ile Ser Lys Ala Ala
        195                 200                 205

Phe Glu Trp Ala Asp His Pro Thr Ala Val Ile Pro Asp Met Gln Lys
210                 215                 220

Leu Gly Ile Lys Asp Lys Asn Glu Ala Ala Arg Ile Val Ala Leu Val
225                 230                 235                 240

Lys Asn Gln Thr Thr Ala Ala Ala Ala Thr Ala Gly Ser Ser Cys Ala
                245                 250                 255

Arg Val Arg Arg Ser Ser Cys Gly Val Asp Lys Pro Glu Val Ile Asp
            260                 265                 270

Ala Ser Glu Leu Thr Pro Ala Val Thr Thr Tyr Lys Leu Val Ile Asn
        275                 280                 285

Gly Lys Thr Leu Lys Gly Glu Thr Thr Thr Glu Ala Val Asp Ala Ala
    290                 295                 300

Thr Ala Glu Lys Val Phe Lys Gln Tyr Ala Asn Asp Asn Gly Val Asp
305                 310                 315                 320

Gly Glu Trp Thr Tyr Asp Asp Ala Thr Lys Thr Phe Thr Val Thr Glu
                325                 330                 335

Lys Pro Glu Val Ile Asp Ala Ser Glu Leu Thr Pro Ala Val Thr Arg
            340                 345                 350

Ser Lys Pro Glu Val Ile Asp Ala Ser Glu Leu Thr Pro Ala Val Thr
        355                 360                 365

Thr Tyr Lys Leu Val Ile Asn Gly Lys Thr Leu Lys Gly Glu Thr Thr
370                 375                 380

Thr Glu Ala Val Asp Ala Ala Thr Ala Glu Lys Val Phe Lys Gln Tyr
385                 390                 395                 400

Ala Asn Asp Asn Gly Val Asp Gly Glu Trp Thr Tyr Asp Asp Ala Thr
                405                 410                 415

Lys Thr Phe Thr Val Thr Glu Lys Pro Glu Val Ile Asp Ala Ser Glu
            420                 425                 430

Leu Thr Pro Ala Val Thr Arg Ser Ala Asp Asn Asn Phe Asn Lys Glu
        435                 440                 445

Gln Gln Asn Ala Phe Tyr Glu Ile Leu Asn Met Pro Asn Leu Asn Glu
    450                 455                 460

Glu Gln Arg Asn Gly Phe Ile Gln Ser Leu Lys Asp Asp Pro Ser Gln
465                 470                 475                 480

Ser Ala Asn Leu Leu Ser Glu Ala Lys Lys Leu Asn Glu Ser Gln Ala
                485                 490                 495

Pro Lys Asp Arg Ser Ala
            500
```

( 2 ) INFORMATION FOR SEQ ID NO:26:

( i ) SEQUENCE CHARACTERISTICS:
( A ) LENGTH: 280 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:26:

| Ala | Ala | Lys | Met | Ala | Lys | Asn | Val | Asp | Lys | Pro | Leu | Phe | Thr | Ala | Thr |
|---|---|---|---|---|---|---|---|---|---|---|---|---|---|---|---|
| 1 | | | | 5 | | | | | 10 | | | | | 15 | |
| Phe | Asn | Val | Gln | Ala | Ser | Ser | Ala | Asp | Tyr | Ala | Thr | Phe | Ile | Ala | Gly |
| | | | 20 | | | | | 25 | | | | | 30 | | |
| Ile | Arg | Asn | Lys | Leu | Arg | Asn | Pro | Ala | His | Phe | Ser | His | Asn | Glu | Pro |
| | | 35 | | | | | 40 | | | | | 45 | | | |
| Val | Leu | Pro | Pro | Val | Glu | Pro | Asn | Val | Pro | Pro | Ser | Arg | Trp | Phe | His |
| | 50 | | | | 55 | | | | | 60 | | | | | |
| Val | Val | Leu | Lys | Ala | Ser | Pro | Thr | Ser | Ala | Gly | Leu | Thr | Leu | Ala | Ile |
| 65 | | | | | 70 | | | | | 75 | | | | | 80 |
| Arg | Ala | Asp | Asn | Ile | Tyr | Leu | Glu | Gly | Phe | Lys | Ser | Ser | Asp | Gly | Thr |
| | | | | 85 | | | | | 90 | | | | | 95 | |
| Trp | Trp | Glu | Leu | Thr | Pro | Gly | Leu | Ile | Pro | Gly | Ala | Thr | Tyr | Val | Gly |
| | | | | 100 | | | | 105 | | | | | 110 | | |
| Phe | Gly | Gly | Thr | Tyr | Arg | Asp | Leu | Leu | Gly | Asp | Thr | Asp | Lys | Leu | Thr |
| | | 115 | | | | | 120 | | | | | 125 | | | |
| Asn | Val | Ala | Leu | Gly | Arg | Gln | Gln | Leu | Glu | Asp | Ala | Val | Thr | Ala | Leu |
| | 130 | | | | | 135 | | | | | 140 | | | | |
| His | Gly | Arg | Thr | Lys | Ala | Asp | Lys | Ala | Ser | Gly | Pro | Lys | Gln | Gln | Gln |
| 145 | | | | | 150 | | | | | 155 | | | | | 160 |
| Ala | Arg | Glu | Ala | Val | Thr | Thr | Leu | Leu | Leu | Met | Val | Asn | Glu | Ala | Thr |
| | | | | 165 | | | | | 170 | | | | | 175 | |
| Arg | Phe | Gln | Thr | Val | Ser | Gly | Phe | Val | Ala | Gly | Leu | Leu | His | Pro | Lys |
| | | | 180 | | | | | 185 | | | | | 190 | | |
| Ala | Val | Glu | Lys | Lys | Ser | Gly | Lys | Ile | Gly | Asn | Glu | Met | Lys | Ala | Gln |
| | | | 195 | | | | 200 | | | | | 205 | | | |
| Val | Asn | Gly | Trp | Gln | Asp | Leu | Ser | Ala | Ala | Leu | Leu | Lys | Thr | Asp | Val |
| | 210 | | | | | 215 | | | | | 220 | | | | |
| Lys | Pro | Pro | Pro | Gly | Lys | Ser | Pro | Ala | Lys | Phe | Thr | Pro | Ile | Glu | Lys |
| 225 | | | | | 230 | | | | | 235 | | | | | 240 |
| Met | Gly | Val | Arg | Thr | Ala | Glu | Gln | Ala | Ala | Ala | Thr | Leu | Gly | Ile | Leu |
| | | | | 245 | | | | | 250 | | | | | 255 | |
| Leu | Phe | Val | Glu | Val | Pro | Gly | Gly | Leu | Thr | Val | Ala | Lys | Ala | Leu | Glu |
| | | | 260 | | | | | 265 | | | | | 270 | | |
| Leu | Phe | His | Ala | Ser | Gly | Gly | Lys | | | | | | | | |
| | | 275 | | | | | 280 | | | | | | | | |

(2) INFORMATION FOR SEQ ID NO:27:

(i) SEQUENCE CHARACTERISTICS:
(A) LENGTH: 290 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:27:

| Met | Tyr | Ala | Val | Ala | Thr | Trp | Leu | Cys | Phe | Gly | Ser | Thr | Ser | Gly | Trp |
|---|---|---|---|---|---|---|---|---|---|---|---|---|---|---|---|
| 1 | | | | 5 | | | | | 10 | | | | | 15 | |
| Ser | Phe | Thr | Leu | Glu | Asp | Asn | Asn | Ile | Phe | Pro | Lys | Gln | Tyr | Pro | Ile |
| | | | 20 | | | | | 25 | | | | | 30 | | |

```
Ile  Asn  Phe  Thr  Thr  Ala  Gly  Ala  Thr  Val  Gln  Ser  Tyr  Thr  Asn  Phe
          35                      40                      45

Ile  Arg  Ala  Val  Arg  Gly  Arg  Leu  Thr  Thr  Gly  Ala  Asp  Val  Arg  His
     50                      55                      60

Glu  Ile  Pro  Val  Leu  Pro  Asn  Arg  Val  Gly  Leu  Pro  Ile  Asn  Gln  Arg
65                       70                      75                       80

Phe  Ile  Leu  Val  Glu  Leu  Ser  Asn  His  Ala  Glu  Leu  Ser  Val  Thr  Leu
                    85                      90                      95

Ala  Leu  Asp  Val  Thr  Asn  Ala  Tyr  Val  Val  Gly  Tyr  Arg  Ala  Gly  Asn
               100                     105                     110

Ser  Ala  Tyr  Phe  Phe  His  Pro  Asp  Asn  Gln  Glu  Asp  Ala  Glu  Ala  Ile
          115                     120                     125

Thr  His  Leu  Phe  Thr  Asp  Val  Gln  Asn  Arg  Tyr  Thr  Phe  Ala  Phe  Gly
     130                     135                     140

Gly  Asn  Tyr  Asp  Arg  Leu  Glu  Gln  Leu  Ala  Gly  Asn  Leu  Arg  Glu  Asn
145                     150                     155                          160

Ile  Glu  Leu  Gly  Asn  Gly  Pro  Leu  Glu  Glu  Ala  Ile  Ser  Ala  Leu  Tyr
                    165                     170                     175

Tyr  Tyr  Ser  Thr  Gly  Gly  Thr  Gln  Leu  Pro  Thr  Leu  Ala  Arg  Ser  Phe
               180                     185                     190

Ile  Ile  Cys  Ile  Gln  Met  Ile  Ser  Glu  Ala  Ala  Arg  Phe  Gln  Tyr  Ile
          195                     200                     205

Glu  Gly  Glu  Met  Arg  Thr  Arg  Ile  Arg  Tyr  Asn  Arg  Arg  Ser  Ala  Pro
     210                     215                     220

Asp  Pro  Ser  Val  Ile  Thr  Leu  Glu  Asn  Ser  Trp  Gly  Arg  Leu  Ser  Thr
225                     230                     235                          240

Ala  Ile  Gln  Glu  Ser  Asn  Gln  Gly  Ala  Phe  Ala  Ser  Pro  Ile  Gln  Leu
                    245                     250                     255

Gln  Arg  Arg  Asn  Gly  Ser  Lys  Phe  Ser  Val  Tyr  Asp  Val  Ser  Ile  Leu
               260                     265                     270

Ile  Pro  Ile  Ile  Ala  Leu  Met  Val  Tyr  Arg  Cys  Ala  Pro  Pro  Pro  Ser
          275                     280                     285

Gln  Phe
290
```

( 2 ) INFORMATION FOR SEQ ID NO:28:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

```
Val  Asn  Thr  Ile  Ile  Tyr  Asn  Val  Gly  Ser  Thr  Thr  Ile  Ser  Asn  Tyr
1                        5                       10                      15

Ala  Thr  Phe  Met  Asp  Asn  Leu  Arg  Asn  Glu  Ala  Lys  Asp
               20                      25
```

( 2 ) INFORMATION FOR SEQ ID NO:29:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:29:

```
Asn Ile Val Phe Asp Tyr Glu Asn Ala Thr Pro Glu Thr Tyr Ser Asn
1               5                   10                  15
Phe Leu Thr Ser Leu Arg Glu Ala Val Lys Asp
                20                  25
```

(2) INFORMATION FOR SEQ ID NO:30:

(i) SEQUENCE CHARACTERISTICS:
        (A) LENGTH: 25 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:30:

```
Lys Glu Phe Thr Leu Asp Phe Ser Thr Ala Lys Thr Tyr Asp Ser Leu
1               5                   10                  15
Asn Val Ile Arg Ser Ala Ile Gly Thr
                20                  25
```

(2) INFORMATION FOR SEQ ID NO:31:

(i) SEQUENCE CHARACTERISTICS:
        (A) LENGTH: 27 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:31:

```
Asp Val Ser Phe Arg Leu Ser Gly Ala Thr Ser Ser Ser Tyr Gly Val
1               5                   10                  15
Phe Ile Ser Asn Leu Arg Lys Ala Leu Pro Asn
                20                  25
```

(2) INFORMATION FOR SEQ ID NO:32:

(i) SEQUENCE CHARACTERISTICS:
        (A) LENGTH: 27 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:32:

```
Asp Val Ser Phe Arg Leu Ser Gly Ala Asp Pro Arg Ser Tyr Gly Met
1               5                   10                  15
Phe Ile Lys Asp Leu Arg Asn Ala Leu Pro Phe
                20                  25
```

(2) INFORMATION FOR SEQ ID NO:33:

(i) SEQUENCE CHARACTERISTICS:
        (A) LENGTH: 27 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:33:

```
Asp Val Ser Phe Arg Leu Ser Gly Ala Thr Thr Thr Ser Tyr Gly Val
1               5                   10                  15

Phe Ile Lys Asn Leu Arg Glu Ala Leu Pro Tyr
            20                  25
```

( 2 ) INFORMATION FOR SEQ ID NO:34:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Gly Leu Asp Thr Val Ser Phe Ser Thr Lys Gly Ala Thr Tyr Ile Thr
1               5                   10                  15

Tyr Val Asn Phe Leu Asn Glu Leu Arg Val Lys Leu Lys Pro
            20                  25                  30
```

( 2 ) INFORMATION FOR SEQ ID NO:35:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

```
Val Thr Ser Ile Thr Leu Asp Leu Val Asn Pro Thr Ala Gly Gln Tyr
1               5                   10                  15

Ser Ser Phe Val Asp Lys Ile Arg Asn Asn Val Lys Asp
            20                  25
```

( 2 ) INFORMATION FOR SEQ ID NO:36:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Val Ile Ile Tyr Glu Leu Asn Leu Gln Gly Thr Thr Lys Ala Gln Tyr
1               5                   10                  15

Ser Thr Ile Leu Lys Gln Leu Arg Asp Asp Ile Lys Asp
            20                  25
```

( 2 ) INFORMATION FOR SEQ ID NO:37:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

```
Val Ser Leu Gly Leu Lys Arg Asp Asn Leu Tyr Val Val Ala Tyr
1               5                   10                  15
```

( 2 ) INFORMATION FOR SEQ ID NO:38:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
Ala  Ile  Gln  Met  Thr  Ala  Glu  Ala  Ala  Arg  Phe  Arg  Tyr  Ile  Gln
 1              5                        10                        15
```

( 2 ) INFORMATION FOR SEQ ID NO:39:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
ACCGTCACCA TGGCCGCGC CGAAATGACC AGGGCCGTCA ACGACCTGGC GAAGAAGAAG      60
AAGGCGGCTG ACCCACAGGC CGACACGAAG AGC                                 93
```

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
CGGATCCAGC AGTAGCGGCA GCGGCAGTAG                                     30
```

( 2 ) INFORMATION FOR SEQ ID NO:41:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

```
ACCGTCACCA TGGCCGCGC CGAAATGACC AGGGCCGTCA ACGACCTGGC GAAGAAGAAG      60
AAGGCGGCCG CCGCTGCAGA CCCACAGGCC GACACGAAG                           99
```

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
CATGCCGGCC AGTGAATTCG G                                              21
```

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (x i) SEQUENCE DESCRIPTION: SEQ ID NO:43:

GATCCGTTAA CGTCGACG                                                                                          18

(2) INFORMATION FOR SEQ ID NO:44:

(i) SEQUENCE CHARACTERISTICS:
  (A) LENGTH: 33 base pairs
  (B) TYPE: nucleic acid
  (C) STRANDEDNESS: single
  (D) TOPOLOGY: linear (x i) SEQUENCE DESCRIPTION: SEQ ID NO:44:

ATATTAGTCG ACAAACCAGA AGTGATCGAT GCG                                                                          33

(2) INFORMATION FOR SEQ ID NO:45:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (x i) SEQUENCE DESCRIPTION: SEQ ID NO:45:

GCAATTGCAG CTGCTTAA                                                                                          18

(2) INFORMATION FOR SEQ ID NO:46:

(i) SEQUENCE CHARACTERISTICS:
  (A) LENGTH: 10 amino acids
  (B) TYPE: amino acid
  (C) STRANDEDNESS: single
  (D) TOPOLOGY: linear (i i) MOLECULE TYPE: protein (x i) SEQUENCE DESCRIPTION: SEQ ID NO:46:

```
Glu Val Asn Trp Lys Lys Ile Ser Thr Ala
1               5                   10
```

(2) INFORMATION FOR SEQ ID NO:47:

(i) SEQUENCE CHARACTERISTICS:
  (A) LENGTH: 15 amino acids
  (B) TYPE: amino acid
  (C) STRANDEDNESS: single
  (D) TOPOLOGY: linear (i i) MOLECULE TYPE: protein (x i) SEQUENCE DESCRIPTION: SEQ ID NO:47:

```
Ile Glu Val Gly Ile Asp Val Thr Asn Ala Tyr Val Val Ala Tyr
1               5                   10                  15
```

(2) INFORMATION FOR SEQ ID NO:48:

(i) SEQUENCE CHARACTERISTICS:
  (A) LENGTH: 15 amino acids
  (B) TYPE: amino acid
  (C) STRANDEDNESS: single
  (D) TOPOLOGY: linear (i i) MOLECULE TYPE: protein (x i) SEQUENCE DESCRIPTION: SEQ ID NO:48:

```
Ile Ile Gln Val Ala Ser Glu Ala Ala Arg Phe Arg Tyr Ile Ser
1               5                   10                  15
```

(2) INFORMATION FOR SEQ ID NO:49:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:49:

```
Leu  Glu  Asn  Asn  Trp  Asp  Asn  Leu  Arg  Gly  Val
1                  5                        10
```

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:50:

```
Met  Ile  Asp  Ser  Gly  Ser  Gly  Asp  Asn  Leu  Phe  Ala  Val  Asp  Val
1                  5                        10                       15
```

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:51:

```
Phe  Val  Thr  Val  Thr  Ala  Glu  Ala  Leu  Arg  Phe  Gln  Ile  Gln  Arg
1                  5                        10                       15
```

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:52:

```
Thr  Leu  Asn  Trp  Gly  Arg  Leu  Ser  Ser  Val
1                  5                        10
```

( 2 ) INFORMATION FOR SEQ ID NO:53:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:53:

```
Asp  Glu  Val  Ala  Leu  Asp  Val  Thr  Asn  Val
1                  5                        10
```

( 2 ) INFORMATION FOR SEQ ID NO:54:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:54:

Tyr Leu Met Gly Tyr
1               5

( 2 ) INFORMATION FOR SEQ ID NO:55:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:55:

Leu Ile Gln Ser Thr Ser Glu Ala Ala Arg Tyr Lys Phe Ile Glu
1               5                   10                  15

( 2 ) INFORMATION FOR SEQ ID NO:56:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:56:

Leu Glu Asn Ser Leu Trp Leu Ala Leu Ser Lys Gln
1               5                   10

( 2 ) INFORMATION FOR SEQ ID NO:57:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:57:

GATCCTCTTG CGCTCGTGTC CGTCGTTCGA GCTGCGGTG                                      39

( 2 ) INFORMATION FOR SEQ ID NO:58:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:58:

GAGAACGCGA GCACAGGCAG CAAGCTCGAC GCCACAGCTG                                     40

( 2 ) INFORMATION FOR SEQ ID NO:59:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:59:

```
Gly Ser Ser Cys Ala Arg Val Arg Arg Ser Ser Cys Gly Val Asp
1               5                   10                  15
```

( 2 ) INFORMATION FOR SEQ ID NO:60:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:60:

```
Tyr Tyr Ser Thr Cys Gly Thr Gln Ile Pro Thr
1               5                   10
```

( 2 ) INFORMATION FOR SEQ ID NO:61:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:61:

```
Ile Ser Phe Phe Arg Ser Gly Gly Asn Asp Asn
1               5                   10
```

( 2 ) INFORMATION FOR SEQ ID NO:62:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:62:

```
Ile Phe His Tyr Asp Ser Thr Ala Ala Ala Ala
1               5                   10
```

( 2 ) INFORMATION FOR SEQ ID NO:63:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

```
Ile Phe His Tyr Asp Ser Thr Ala Ala Ala Ala
1               5                   10
```

( 2 ) INFORMATION FOR SEQ ID NO:64:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:64:

```
Leu  Leu  His  Tyr  Asp  Ser  Thr  Ala  Ala  Ala  Gly
1                   5                        10
```

( 2 ) INFORMATION FOR SEQ ID NO:65:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:65:

```
Thr  Leu  Phe  Tyr  Tyr  Asn  Ala  Asn  Ser  Ala  Ala
1                   5                        10
```

( 2 ) INFORMATION FOR SEQ ID NO:66:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:66:

```
Ile  Ser  Gly  Gln  Gly  Ser  Phe  Thr  Glu  Lys  Ile
1                   5                        10
```

( 2 ) INFORMATION FOR SEQ ID NO:67:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:67:

```
Ile  Tyr  Gly  Lys  Ala  Gly  Asp  Val  Lys  Lys  Gln
1                   5                        10
```

( 2 ) INFORMATION FOR SEQ ID NO:68:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:68:

```
Val  Asn  Lys  Lys  Ala  Arg  Val  Val  Lys  Asp  Glu
1                   5                        10
```

( 2 ) INFORMATION FOR SEQ ID NO:69:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:69:

```
Thr Lys Ala Asp Lys Ala Ser Gly Pro Lys Gln
1               5                   10
```

( 2 ) INFORMATION FOR SEQ ID NO:70:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:70:

```
Asp Gly Val Asn Lys Lys Val Arg Val Val Lys
1               5                   10
```

( 2 ) INFORMATION FOR SEQ ID NO:71:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:71:

```
Glu Asp Arg Pro Ile Lys Phe Ser Thr Glu Gly Ala Thr Ser Gln Ser
1               5                   10                  15

Tyr Lys Gln Phe Ile Glu Ala Leu Arg Glu Arg Leu Arg Gly Gly Leu
                20                  25                  30

Ile His Asp Ile Pro Val Leu Pro Asp Pro Thr Thr Leu Gln Glu Arg
                35                  40                  45

Asn Arg Tyr Ile Thr Val Glu Leu Ser Asn Ser Asp Thr Glu Ser Ile
        50                  55                  60

Glu Val Gly Ile Asp Val Thr Asn Ala Tyr Val Val Ala Tyr Arg Ala
65                      70                  75                  80

Gly Thr Gln Ser Tyr Phe Leu Arg Asp Ala Pro Ser Ser Ala Ser Asp
                85                  90                  95

Tyr Leu Phe Thr Gly Thr Asp Gln His Ser Leu Pro Phe Tyr Gly Thr
                100                 105                 110

Tyr Gly Asp Leu Glu Arg Trp Ala His Gln Ser Arg Gln Gln Ile Pro
                115                 120                 125

Leu Gly Leu Gln Ala Leu Thr His Gly Ile Ser Phe Phe Arg Ser Gly
        130                 135                 140

Gly Asn Asp Asn Glu Glu Lys Ala Arg Thr Leu Ile Val Ile Ile Gln
145                     150                 155                 160

Met Val Ala Glu Ala Ala Arg Phe Arg Tyr Ile Ser Asn Arg Val Arg
                165                 170                 175

Val Ser Ile Gln Thr Gly Thr Ala Phe Gln Pro Asp Ala Ala Met Ile
                180                 185                 190

Ser Leu Glu Asn Asn Trp Asp Asn Leu Arg Gly Val Gln Glu Ser Val
                195                 200                 205

Gln Asp Thr Phe Pro Asn Gln Val Thr Leu Thr Asn Ile Arg Asn Glu
        210                 215                 220

Pro Val Ile Val Asp Ser Leu Ser His Pro Thr Val Ala Val Leu Ala
```

5,646,026
                              113                                                                         114
                                                            -continued 225                              230                           235                               240
      Leu  Met  Leu  Phe  Val  Cys  Asn  Pro  Pro  Asn
                           245                           250

( 2 ) INFORMATION FOR SEQ ID NO:72:

( i ) SEQUENCE CHARACTERISTICS:
            ( A ) LENGTH: 260 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:72:

Val  Thr  Ser  Ile  Thr  Leu  Asp  Leu  Val  Asn  Pro  Thr  Ala  Gly  Gln  Tyr
    1                    5                         10                        15

Ser  Ser  Phe  Val  Asp  Lys  Ile  Arg  Asn  Asn  Val  Lys  Asp  Pro  Asn  Leu
                    20                        25                       30

Lys  Tyr  Gly  Gly  Thr  Asp  Ile  Ala  Val  Ile  Gly  Pro  Pro  Ser  Lys  Glu
               35                         40                        45

Lys  Phe  Leu  Arg  Ile  Asn  Phe  Gln  Ser  Ser  Arg  Gly  Thr  Val  Ser  Leu
         50                        55                        60

Gly  Leu  Lys  Arg  Asp  Asn  Leu  Tyr  Val  Val  Ala  Tyr  Leu  Ala  Met  Asp
    65                        70                        75                         80

Asn  Thr  Asn  Val  Asn  Arg  Ala  Tyr  Tyr  Phe  Arg  Ser  Glu  Ile  Thr  Ser
                        85                        90                         95

Ala  Glu  Ser  Thr  Ala  Leu  Phe  Pro  Glu  Ala  Thr  Thr  Ala  Asn  Gln  Lys
                   100                       105                       110

Ala  Leu  Glu  Tyr  Thr  Glu  Asp  Tyr  Gln  Ser  Ile  Glu  Lys  Asn  Ala  Gln
              115                        120                       125

Ile  Thr  Gln  Gly  Asp  Gln  Ser  Arg  Lys  Glu  Leu  Gly  Leu  Gly  Ile  Asp
         130                       135                       140

Leu  Leu  Ser  Thr  Ser  Met  Glu  Ala  Val  Asn  Lys  Lys  Ala  Arg  Val  Val
    145                       150                       155                       160

Lys  Asp  Glu  Ala  Arg  Phe  Leu  Leu  Ile  Ala  Ile  Gln  Met  Thr  Ala  Glu
                        165                       170                       175

Ala  Ala  Arg  Phe  Arg  Tyr  Ile  Gln  Asn  Leu  Val  Ile  Lys  Asn  Phe  Pro
                   180                       185                       190

Asn  Lys  Phe  Asn  Ser  Glu  Asn  Lys  Val  Ile  Gln  Phe  Glu  Val  Asn  Trp
              195                       200                       205

Lys  Lys  Ile  Ser  Thr  Ala  Ile  Tyr  Gly  Asp  Ala  Lys  Asn  Gly  Val  Phe
         210                       215                       220

Asn  Lys  Asp  Tyr  Asp  Phe  Gly  Phe  Gly  Lys  Val  Arg  Gln  Val  Lys  Asp
    225                       230                       235                       240

Leu  Gln  Met  Gly  Leu  Leu  Met  Tyr  Leu  Gly  Lys  Pro  Lys  Ser  Ser  Asn
                        245                       250                       255

Glu  Ala  Asn  Ser
                   260

( 2 ) INFORMATION FOR SEQ ID NO:73:

( i ) SEQUENCE CHARACTERISTICS:
            ( A ) LENGTH: 315 amino acids
            ( B ) TYPE: amino acid
            ( C ) STRANDEDNESS: single
            ( D ) TOPOLOGY: linear ( i i ) MOLECULE TYPE: protein -continued ( x i ) SEQUENCE DESCRIPTION: SEQ ID NO:73:

```
Met Lys Ile Ile Ile Phe Arg Val Leu Thr Phe Phe Val Ile Phe
1               5                   10                  15

Ser Val Asn Val Val Ala Lys Glu Phe Thr Leu Asp Phe Ser Thr Ala
            20              25                  30

Lys Thr Tyr Val Asp Ser Leu Asn Val Ile Arg Ser Ala Ile Gly Thr
        35              40                  45

Pro Leu Gln Thr Ile Ser Ser Gly Gly Thr Ser Leu Leu Met Ile Asp
    50              55                      60

Ser Gly Ser Gly Asp Asn Leu Phe Ala Val Asp Val Arg Gly Ile Asp
65              70                  75                  80

Pro Glu Glu Gly Arg Phe Asn Asn Leu Arg Leu Ile Val Glu Arg Asn
            85                      90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
            115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
            245                 250                 255

Ser Val Ala Leu Ile Leu Asn Cys His His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315
```

( 2 ) INFORMATION FOR SEQ ID NO:74:

( i ) SEQUENCE CHARACTERISTICS:
        ( A ) LENGTH: 267 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:74:

```
Gly Asp Val Ser Phe Arg Leu Ser Gly Ala Thr Ser Ser Ser Tyr Gly
1               5                   10                  15

Val Phe Ile Ser Asn Leu Arg Lys Ala Leu Pro Asn Glu Arg Lys Leu
            20                  25                  30
```

```
Tyr  Asp  Ile  Pro  Leu  Leu  Arg  Ser  Ser  Leu  Pro  Gly  Ser  Gln  Arg  Tyr
          35                       40                       45

Ala  Leu  Ile  His  Leu  Thr  Asn  Tyr  Ala  Asp  Glu  Thr  Ile  Ser  Val  Ala
     50                       55                       60

Ile  Asp  Val  Thr  Asn  Val  Tyr  Ile  Met  Gly  Tyr  Arg  Ala  Gly  Asp  Thr
65                       70                       75                       80

Ser  Tyr  Phe  Phe  Asn  Glu  Ala  Ser  Ala  Thr  Glu  Ala  Ala  Lys  Tyr  Val
               85                       90                       95

Phe  Lys  Asp  Ala  Met  Arg  Lys  Val  Thr  Leu  Pro  Tyr  Ser  Gly  Asn  Tyr
               100                      105                      110

Glu  Arg  Leu  Gln  Thr  Ala  Ala  Gly  Lys  Ile  Arg  Glu  Asn  Ile  Pro  Leu
          115                      120                      125

Gly  Leu  Pro  Ala  Leu  Asp  Ser  Ala  Ile  Thr  Thr  Leu  Phe  Tyr  Tyr  Asn
130                      135                      140

Ala  Asn  Ser  Ala  Ala  Ser  Ala  Leu  Met  Val  Leu  Ile  Gln  Ser  Thr  Ser
145                      150                      155                      160

Glu  Ala  Ala  Arg  Tyr  Lys  Phe  Ile  Glu  Gln  Gln  Ile  Gly  Lys  Arg  Val
               165                      170                      175

Asp  Lys  Thr  Phe  Leu  Pro  Ser  Leu  Ala  Ile  Ile  Ser  Leu  Glu  Asn  Ser
               180                      185                      190

Trp  Ser  Ala  Leu  Ser  Lys  Gln  Ile  Gln  Ile  Ala  Ser  Thr  Asn  Asn  Gly
          195                      200                      205

Gln  Phe  Glu  Ser  Pro  Val  Val  Leu  Ile  Asn  Ala  Gln  Asn  Gln  Arg  Val
     210                      215                      220

Thr  Ile  Thr  Asn  Val  Asp  Ala  Gly  Val  Val  Thr  Ser  Asn  Ile  Ala  Leu
225                      230                      235                      240

Leu  Leu  Asn  Arg  Asn  Asn  Met  Ala  Ala  Met  Asp  Asp  Asp  Val  Pro  Met
               245                      250                      255

Thr  Gln  Ser  Phe  Gly  Cys  Gly  Ser  Tyr  Ala  Ile
               260                      265
```

( 2 ) INFORMATION FOR SEQ ID NO:75:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:75:

```
Asp  Val  Arg  Phe  Ser  Leu  Ser  Gly  Ser  Ser  Thr  Ser  Tyr  Ser  Lys
1                   5                        10                       15

Phe  Ile  Gly  Asp  Leu  Arg  Lys  Ala  Leu  Pro  Ser  Asn  Gly  Thr  Val  Tyr
               20                       25                       30

Asn  Leu  Thr  Ile  Leu  Leu  Ser  Ser  Ala  Ser  Gly  Ala  Ser  Arg  Tyr  Thr
               35                       40                       45

Leu  Met  Thr  Leu  Ser  Asn  Tyr  Asp  Gly  Lys  Ala  Ile  Thr  Val  Ala  Val
     50                       55                       60

Asp  Val  Ser  Gln  Leu  Tyr  Ile  Met  Gly  Tyr  Leu  Val  Asn  Ser  Thr  Ser
65                       70                       75                       80

Tyr  Phe  Phe  Asn  Glu  Ser  Asp  Ala  Lys  Leu  Ala  Ser  Gln  Tyr  Val  Phe
               85                       90                       95

Lys  Gly  Ser  Thr  Ile  Val  Thr  Leu  Pro  Tyr  Ser  Gly  Asn  Tyr  Glu  Lys
               100                      105                      110
```

```
Leu Gln Thr Ala Ala Gly Lys Ile Arg Glu Lys Ile Pro Leu Gly Phe
    115             120                 125

Pro Ala Leu Asp Ser Ala Leu Thr Thr Ile Phe His Tyr Asp Ser Thr
    130             135                 140

Ala Ala Ala Ala Ala Phe Leu Val Ile Leu Gln Thr Thr Ala Glu Ala
145             150                 155                     160

Ser Arg Phe Lys Tyr Ile Glu Gly Gln Ile Ile Glu Arg Ile Ser Lys
                165                 170                 175

Asn Gln Val Pro Ser Leu Ala Thr Ile Ser Leu Glu Asn Ser Leu Trp
            180                 185                 190

Ser Ala Leu Ser Lys Gln Ile Gln Leu Ala Gln Thr Asn Asn Gly Thr
            195                 200                 205

Phe Lys Thr Pro Val Val Ile Thr Asp Asp Lys Gly Gln Arg Val Glu
    210                 215                 220

Ile Thr Asn Val Thr Ser Lys Val Val Thr Lys Asn Ile Gln Leu Leu
225                 230                 235                 240

Leu Asn Tyr Lys Gln Asn Val Ala
                245
```

( 2 ) INFORMATION FOR SEQ ID NO:76:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:76:

```
Ala Pro Thr Leu Glu Thr Leu Ala Ser Leu Asp Leu Asn Asn Pro Thr
1               5                   10                  15

Thr Tyr Leu Ser Phe Ile Thr Asn Ile Arg Thr Lys Val Val Asp Lys
                20                  25                  30

Thr Glu Gln Cys Thr Ile Gln Lys Ile Ser Lys Thr Phe Thr Gln Arg
            35                  40                  45

Tyr Ser Tyr Ile Asp Leu Ile Val Ser Ser Thr Gln Lys Ile Thr Leu
    50                  55                  60

Ala Ile Asp Met Ala Asp Leu Tyr Val Leu Gly Tyr Ser Asp Ile Ala
65              70                  75                      80

Asn Asn Lys Gly Arg Ala Phe Phe Phe Lys Asp Val Thr Glu Ala Val
                85                  90                  95

Ala Asn Asn Phe Phe Pro Gly Ala Thr Gly Thr Asn Arg Ile Lys Leu
            100                 105                 110

Thr Phe Thr Gly Ser Tyr Gly Asp Leu Glu Lys Asn Gly Gly Leu Arg
    115                 120                 125

Lys Asp Asn Pro Leu Gly Ile Phe Arg Leu Glu Asn Ser Ile Val Asn
    130                 135                 140

Ile Tyr Gly Lys Ala Gly Asp Val Lys Lys Gln Ala Lys Phe Phe Leu
145                 150                 155                 160

Leu Ala Ile Gln Met Val Ser Glu Ala Ala Arg Phe Lys Tyr Ile Ser
                165                 170                 175

Asp Lys Ile Pro Ser Glu Lys Tyr Glu Glu Val Thr Val Gly Glu Tyr
            180                 185                 190

Met Thr Ala Leu Glu Asn Asn Trp Ala Lys Leu Ser Thr Ala Val Tyr
    195                 200                 205

Asn Ser Lys Pro Ser Thr Thr Thr Ala Thr Lys Cys Gln Leu Ala Thr
```

```
                    210                    215                         220
Ser  Pro  Val  Thr  Ile  Ser  Pro  Trp  Ile  Phe  Lys  Thr  Val  Glu  Glu  Ile
225                      230                      235                      240

Lys  Leu  Val  Met  Gly  Leu  Leu  Lys  Ser  Ser
                    245                      250
```

( 2 ) INFORMATION FOR SEQ ID NO:77:

( i ) SEQUENCE CHARACTERISTICS:
      ( A ) LENGTH: 540 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:77:

```
Ile  Phe  Pro  Lys  Gln  Tyr  Pro  Ile  Ile  Asn  Phe  Thr  Thr  Ala  Asp  Ala
1                   5                        10                       15

Thr  Val  Glu  Ser  Tyr  Thr  Asn  Phe  Ile  Arg  Ala  Val  Arg  Ser  His  Leu
               20                       25                      30

Thr  Thr  Gly  Ala  Asp  Val  Arg  His  Glu  Ile  Pro  Val  Leu  Pro  Asn  Arg
          35                        40                            45

Val  Gly  Leu  Pro  Ile  Ser  Gln  Arg  Phe  Ile  Leu  Val  Glu  Leu  Ser  Asn
     50                        55                            60

His  Ala  Glu  Leu  Ser  Val  Thr  Leu  Ala  Leu  Asp  Val  Thr  Asn  Ala  Tyr
65                       70                       75                       80

Val  Val  Gly  Cys  Arg  Ala  Gly  Asn  Ser  Ala  Tyr  Phe  Phe  His  Pro  Asp
               85                       90                            95

Asn  Gln  Glu  Asp  Ala  Glu  Ala  Ile  Thr  His  Leu  Phe  Thr  Asp  Val  Gln
               100                      105                      110

Asn  Ser  Phe  Thr  Phe  Ala  Phe  Gly  Gly  Asn  Tyr  Asp  Arg  Leu  Glu  Gln
          115                      120                      125

Leu  Gly  Gly  Leu  Arg  Glu  Asn  Ile  Glu  Leu  Gly  Thr  Gly  Pro  Leu  Glu
     130                      135                      140

Asp  Ala  Ile  Ser  Ala  Leu  Tyr  Tyr  Tyr  Ser  Thr  Cys  Gly  Thr  Gln  Ile
145                      150                      155                      160

Pro  Thr  Leu  Ala  Arg  Ser  Phe  Met  Val  Cys  Ile  Gln  Met  Ile  Ser  Glu
                    165                      170                      175

Ala  Ala  Arg  Phe  Gln  Tyr  Ile  Glu  Gly  Glu  Met  Arg  Thr  Arg  Ile  Arg
               180                      185                      190

Tyr  Asn  Arg  Arg  Ser  Ala  Pro  Asp  Pro  Ser  Val  Ile  Thr  Leu  Glu  Asn
          195                      200                      205

Ser  Trp  Gly  Arg  Leu  Ser  Thr  Ala  Ile  Gln  Glu  Ser  Asn  Gln  Gly  Ala
     210                      215                      220

Phe  Ala  Ser  Pro  Ile  Gln  Leu  Gln  Arg  Arg  Asn  Gly  Ser  Lys  Phe  Asn
225                      230                      235                      240

Val  Tyr  Asp  Val  Ser  Ile  Leu  Ile  Pro  Ile  Ile  Ala  Leu  Met  Val  Tyr
                    245                      250                      255

Arg  Cys  Ala  Pro  Pro  Pro  Ser  Ser  Gln  Phe  Ser  Leu  Leu  Ile  Arg  Pro
               260                      265                      270

Val  Val  Pro  Asn  Phe  Asn  Ala  Asp  Val  Cys  Met  Asp  Pro  Glu  Pro  Ile
          275                      280                      285

Val  Arg  Ile  Val  Gly  Arg  Asn  Gly  Leu  Cys  Val  Asp  Val  Thr  Gly  Glu
     290                      295                      300

Glu  Phe  Phe  Asp  Gly  Asn  Pro  Ile  Gln  Leu  Trp  Pro  Cys  Lys  Ser  Asn
305                      310                      315                      320
```

```
Thr  Asp  Trp  Asn  Gln  Leu  Trp  Thr  Leu  Arg  Lys  Asp  Ser  Thr  Ile  Arg
               325                      330                      335

Ser  Asn  Gly  Lys  Cys  Leu  Thr  Ile  Ser  Lys  Ser  Ser  Pro  Arg  Gln  Gln
               340                      345                      350

Val  Val  Ile  Tyr  Asn  Cys  Ser  Thr  Ala  Thr  Val  Gly  Ala  Thr  Arg  Trp
               355                      360                      365

Gln  Ile  Trp  Asp  Asn  Arg  Thr  Ile  Ile  Asn  Pro  Arg  Ser  Gly  Leu  Val
          370                      375                      380

Leu  Ala  Ala  Thr  Ser  Gly  Asn  Ser  Gly  Thr  Lys  Leu  Thr  Val  Gln  Thr
385                           390                      395                      400

Asn  Ile  Tyr  Ala  Val  Ser  Gln  Gly  Trp  Leu  Pro  Thr  Asn  Asn  Thr  Gln
                    405                      410                           415

Pro  Phe  Val  Thr  Thr  Ile  Val  Gly  Leu  Tyr  Gly  Met  Cys  Leu  Gln  Ala
               420                      425                           430

Asn  Ser  Gly  Lys  Val  Trp  Leu  Glu  Asp  Cys  Thr  Ser  Glu  Lys  Ala  Glu
               435                      440                      445

Gln  Gln  Trp  Ala  Leu  Tyr  Ala  Asp  Gly  Ser  Ile  Arg  Pro  Gln  Gln  Asn
     450                      455                      460

Arg  Asp  Asn  Cys  Leu  Thr  Thr  Asp  Ala  Asn  Ile  Lys  Gly  Thr  Val  Val
465                      470                      475                           480

Lys  Ile  Leu  Ser  Cys  Gly  Pro  Ala  Ser  Ser  Gly  Gln  Arg  Trp  Met  Phe
                    485                      490                           495

Lys  Asn  Asp  Gly  Thr  Ile  Leu  Asn  Leu  Tyr  Asn  Gly  Leu  Val  Leu  Asp
               500                      505                      510

Val  Arg  Arg  Ser  Asp  Pro  Ser  Leu  Lys  Gln  Ile  Ile  Val  His  Pro  Phe
               515                      520                      525

His  Gly  Asn  Leu  Asn  Gln  Ile  Trp  Leu  Pro  Leu  Phe
               530                      535                 540
```

( 2 ) INFORMATION FOR SEQ ID NO:78:

( i ) SEQUENCE CHARACTERISTICS:
( A ) LENGTH: 250 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:78:

```
Asp  Val  Ser  Phe  Arg  Leu  Ser  Gly  Ala  Asp  Pro  Arg  Ser  Tyr  Gly  Met
1                   5                      10                      15

Phe  Ile  Lys  Asp  Leu  Arg  Asn  Ala  Leu  Pro  Phe  Arg  Glu  Lys  Val  Tyr
               20                      25                      30

Asn  Ile  Pro  Leu  Leu  Leu  Pro  Ser  Val  Ser  Gly  Ala  Gly  Arg  Tyr  Leu
               35                      40                      45

Leu  Met  His  Leu  Phe  Asn  Tyr  Asp  Gly  Lys  Thr  Ile  Thr  Val  Ala  Val
          50                      55                      60

Asp  Val  Thr  Asn  Val  Tyr  Ile  Met  Gly  Tyr  Leu  Ala  Asp  Thr  Thr  Ser
65                       70                      75                           80

Tyr  Phe  Phe  Asn  Gln  Pro  Ala  Ala  Glu  Leu  Ala  Ser  Gln  Tyr  Val  Phe
               85                      90                      95

Arg  Asp  Ala  Arg  Lys  Ile  Thr  Leu  Pro  Tyr  Ser  Gly  Asn  Tyr  Glu  Arg
               100                     105                     110

Leu  Gln  Ile  Ala  Ala  Gly  Lys  Pro  Arg  Glu  Lys  Leu  Pro  Ile  Gly  Leu
          115                     120                     125
```

```
Pro  Ala  Ile  Asp  Ser  Ala  Ile  Ser  Thr  Leu  Leu  His  Tyr  Asp  Ser  Thr
     130                      135                      140

Ala  Ala  Ala  Gly  Ala  Leu  Leu  Val  Leu  Ile  Gln  Thr  Thr  Ala  Glu  Ala
145                      150                      155                      160

Ala  Arg  Phe  Lys  Tyr  Ile  Glu  Gln  Gln  Ile  Gln  Glu  Arg  Ala  Tyr  Arg
                    165                      170                      175

Asp  Glu  Val  Pro  Ser  Ile  Ala  Thr  Leu  Ser  Leu  Glu  Asn  Ser  Leu  Trp
               180                      185                      190

Ser  Gly  Leu  Ser  Lys  Gln  Ile  Gln  Leu  Ala  Gln  Gly  Asn  Asn  Gly  Ile
          195                      200                      205

Phe  Arg  Thr  Pro  Ile  Val  Leu  Val  Asp  Asn  Lys  Gly  Asn  Arg  Val  Gln
     210                      215                      220

Ile  Thr  Asn  Val  Thr  Ser  Lys  Val  Val  Thr  Ser  Asn  Ile  Gln  Leu  Leu
225                      230                      235                      240

Leu  Val  Thr  Arg  Asn  Ile  Ala  Glu  Gly  Asp
               245                      250
```

(2) INFORMATION FOR SEQ ID NO:79:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:79:

```
Ile  Asn  Thr  Ile  Thr  Phe  Asp  Ala  Gly  Asn  Ala  Thr  Ile  Asn  Lys  Tyr
1                        5                        10                       15

Ala  Thr  Phe  Met  Glu  Ser  Leu  Arg  Asn  Glu  Ala  Lys  Asp  Pro  Ser  Leu
               20                       25                       30

Lys  Cys  Tyr  Gly  Ile  Pro  Met  Leu  Pro  Asn  Thr  Asn  Ser  Thr  Ile  Lys
          35                       40                       45

Tyr  Leu  Leu  Val  Lys  Leu  Gln  Gly  Ala  Ser  Leu  Lys  Thr  Ile  Thr  Leu
     50                       55                       60

Met  Leu  Arg  Arg  Asn  Asn  Leu  Tyr  Val  Met  Gly  Tyr  Ser  Asp  Pro  Tyr
65                       70                       75                       80

Asp  Asn  Lys  Cys  Arg  Tyr  His  Ile  Phe  Asn  Asp  Ile  Lys  Gly  Thr  Glu
                    85                       90                       95

Tyr  Ser  Asp  Val  Glu  Asn  Thr  Leu  Cys  Pro  Ser  Ser  Asn  Pro  Arg  Val
               100                      105                      110

Ala  Lys  Pro  Ile  Asn  Tyr  Asn  Gly  Leu  Tyr  Pro  Thr  Leu  Glu  Lys  Lys
          115                      120                      125

Ala  Gly  Val  Thr  Ser  Arg  Asn  Glu  Val  Gln  Leu  Gly  Ile  Gln  Ile  Leu
     130                      135                      140

Ser  Ser  Asp  Ile  Gly  Lys  Ile  Ser  Gly  Gln  Gly  Ser  Phe  Thr  Glu  Lys
145                      150                      155                      160

Ile  Glu  Ala  Lys  Phe  Leu  Leu  Val  Ala  Ile  Gln  Met  Val  Ser  Glu  Ala
                    165                      170                      175

Ala  Arg  Phe  Lys  Tyr  Ile  Glu  Asn  Gln  Val  Lys  Thr  Asn  Phe  Asn  Arg
               180                      185                      190

Asp  Phe  Ser  Pro  Asn  Asp  Lys  Val  Leu  Asp  Leu  Glu  Glu  Asn  Trp  Gly
          195                      200                      205

Lys  Ile  Ser  Thr  Ala  Ile  His  Asn  Ser  Lys  Asn  Gly  Ala  Leu  Pro  Lys
     210                      215                      220

Pro  Leu  Glu  Leu  Lys  Asn  Ala  Asp  Gly  Thr  Lys  Trp  Ile  Val  Leu  Arg
```

```
                  225                         230                         235                         240

Val  Asp  Glu  Ile  Lys  Pro  Asp  Val  Gly  Leu  Leu  Asn  Tyr  Val  Asn  Gly
                                 245                         250                         255

Thr  Cys  Gln  Ala  Thr
                                 260
```

( 2 ) INFORMATION FOR SEQ ID NO:80:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:80:

```
Ala  Asn  Val  Ser  Phe  Ser  Leu  Ser  Gly  Ala  Asp  Ser  Lys  Ser  Tyr  Ser
1                   5                        10                       15

Lys  Phe  Ile  Thr  Ala  Leu  Arg  Lys  Ala  Leu  Pro  Ser  Lys  Glu  Lys  Val
               20                       25                       30

Ser  Asn  Ile  Pro  Leu  Leu  Leu  Pro  Ser  Ala  Ser  Gly  Ala  Ser  Arg  Tyr
               35                       40                       45

Ile  Leu  Met  Gln  Leu  Ser  Asn  Tyr  Asp  Ala  Lys  Ala  Ile  Thr  Met  Ala
          50                       55                       60

Ile  Asp  Val  Thr  Asn  Val  Tyr  Ile  Met  Gly  Tyr  Leu  Val  Asn  Ser  Thr
65                       70                       75                       80

Ser  Tyr  Phe  Ala  Asn  Glu  Ser  Asp  Ala  Lys  Leu  Ala  Ser  Gln  Tyr  Val
                    85                       90                       95

Phe  Lys  Gly  Ser  Thr  Leu  Val  Thr  Ile  Pro  Tyr  Ser  Gly  Asn  Tyr  Glu
               100                      105                      110

Arg  Leu  Gln  Asn  Ala  Ala  Gly  Lys  Ile  Arg  Glu  Lys  Ile  Pro  Leu  Gly
               115                      120                      125

Phe  Arg  Ala  Leu  Asp  Ser  Ala  Leu  Thr  Ser  Ile  Phe  His  Tyr  Asp  Ser
          130                      135                      140

Thr  Ala  Ala  Ala  Ala  Ala  Phe  Leu  Val  Ile  Leu  Gln  Thr  Thr  Ala  Glu
145                      150                      155                      160

Ala  Ser  Arg  Phe  Lys  Tyr  Ile  Glu  Gly  Gln  Ile  Ile  Glu  Arg  Ile  Pro
                    165                      170                      175

Lys  Asn  Glu  Val  Pro  Ser  Pro  Ala  Ala  Leu  Ser  Leu  Glu  Asn  Glu  Ala
               180                      185                      190

Trp  Ser  Leu  Leu  Ser  Lys  Gln  Ile  Gln  Leu  Ala  Gln  Thr  Asn  Asn  Gly
               195                      200                      205

Ala  Phe  Arg  Thr  Pro  Val  Val  Ile  Ile  Asp  Asn  Lys  Gly  Gln  Arg  Val
          210                      215                      220

Glu  Ile  Thr  Asn  Leu  Ala  Ser  Lys  Val  Gln  Ile  Lys  Asp  Val  Asn  Ser
225                      230                      235                      240

Lys  Leu  Leu  Leu  Asn  Lys  Gln  Asn  Ile  Ala
                    245                      250
```

( 2 ) INFORMATION FOR SEQ ID NO:81:

( i ) SEQUENCE CHARACTERISTICS:
        ( A ) LENGTH: 292 amino acids
        ( B ) TYPE: amino acid
        ( C ) STRANDEDNESS: single
        ( D ) TOPOLOGY: linear ( i i ) MOLECULE TYPE: protein (x i) SEQUENCE DESCRIPTION: SEQ ID NO:81:

```
Lys Ile Tyr Leu Val Ala Ala Ile Ala Trp Ile Leu Phe Gln Ser Ser
 1               5                   10                  15

Ser Trp Thr Thr Asp Ala Ala Thr Ala Tyr Thr Leu Asn Leu Ala Asn
            20                  25                  30

Pro Ser Ala Ser Gln Tyr Ser Ser Phe Leu Asp Gln Ile Arg Asn Asn
        35                  40                  45

Val Arg Asp Thr Ser Leu Ile Tyr Gly Gly Thr Asp Val Glu Val Ile
    50                  55                  60

Gly Ala Pro Ser Thr Thr Asp Lys Phe Leu Arg Leu Asn Phe Gln Gly
65                      70                  75                  80

Pro Arg Gly Thr Val Ser Leu Gly Leu Arg Arg Glu Asn Leu Tyr Val
                85                  90                  95

Val Ala Tyr Leu Ala Met Asp Asn Ala Asn Val Asn Arg Ala Tyr Tyr
            100                 105                 110

Phe Lys Asn Gln Ile Thr Ser Ala Glu Leu Thr Ala Leu Phe Pro Glu
        115                 120                 125

Val Val Val Ala Asn Gln Lys Gln Leu Glu Tyr Gly Glu Asp Tyr Gln
    130                 135                 140

Ala Ile Glu Lys Asn Ala Lys Ile Thr Thr Gly Asp Gln Ser Arg Lys
145                 150                 155                 160

Glu Leu Gly Leu Gly Ile Asn Leu Leu Ile Thr Met Ile Asp Gly Val
                165                 170                 175

Asn Lys Lys Val Arg Val Val Lys Asp Glu Ala Arg Phe Leu Leu Ile
            180                 185                 190

Ala Ile Gln Met Thr Ala Glu Ala Ala Arg Phe Arg Tyr Ile Gln Asn
        195                 200                 205

Leu Val Thr Lys Asn Phe Pro Asn Lys Phe Asp Ser Glu Asn Lys Val
    210                 215                 220

Ile Gln Phe Gln Val Ser Trp Ser Lys Ile Ser Thr Ala Ile Phe Gly
225                 230                 235                 240

Asp Cys Lys Asn Gly Val Phe Asn Lys Asp Tyr Asp Phe Gly Phe Gly
                245                 250                 255

Lys Val Arg Gln Ala Lys Asp Leu Gln Met Gly Leu Leu Lys Tyr Leu
            260                 265                 270

Gly Arg Pro Lys Ser Ser Ser Ile Glu Ala Asn Ser Thr Asp Asp Thr
        275                 280                 285

Ala Asp Val Leu
    290
```

We hereby claim:

1. An isolated DNA encoding a protein, said protein having an amino acid sequence of SEQ ID NO:2 termed a pro-Ribosome Inactivating Protein (proRIP), wherein the proRiP has a selectively removable, internal peptide linker sequence that has from about 9 to 25 amino acids which is at least 70% homologous to residues 162 through 186 of SEQ ID NO;2 and is incapable of substantially inactivating eukaryotic ribosomes, but which can be converted by removal of the linker into a protein having α and β fragments and being capable of substantially inactivating eukaryohic ribosomes, wherein the α fragment has the amino acid sequence of residues 17 to 161 of SEQ ID NO:2 and the β fragment has the amino acid sequence of residues 187 to 287 of SEQ ID NO;2.

2. An isolated DNA sequence encoding a protein being capable of substantially inactivating eukaryotic ribosomes, said protein having an amino acid sequence selected from the group consisting of SEQ ID NOS: 7, 9, 11, 13, 15 17, 19, 21, 23, and 25.

3. An isolated DNA comprising a DNA sequence selected from the group consisting of SEQ ID NOS:6, 8, 10, 12, 14, 16, 18, 20, 22, and 24.

4. A DNA isolate encoding a protein, termed a pro-Ribosome Inactivating Protein (proRIP), comprising a selectively removable, internal peptide linker sequence and is incapable of substantially inactivating eukaryotic ribosomes, but it can be converted by removal of the linker into a protein having α and β fragments, termed a RIP, that is capable of substantially inactivating eukaryotic ribosomes, said proRIP wherein (1) the RIP is selected from the group consisting of Barley Translation Inhibitor (SEQ ID NO:26), Ricin A-chain RIP (SEQ ID NO:27), Abrin-A A-chain (SEQ ID NO:71), Saporin (SEQ ID NO:72), SLT-1

RIP (SEQ ID NO:73), Trichosanthin (SEQ ID NO:74), Luffin-A (SEQ ID NO:75), MAP (SEQ ID NO:76), Ricinus commahis agglutinin (SEQ ID NO:77), Momordin (SEQ ID NO:78), PAP-S (SEQ ID NO:79), buffin-B (SEQ ID NO:80), and Dianthin 30 (SEQ ID NO:81), (2) a removable, internal peptide linker sequence that inhibits RIP activity and is at least 70% homologous to residues 162–186 of SEQ ID NO:2, (3) the proRIP is generated by inserting the linker peptide of (2) into a selected sequence of (1), and is inserted into said selected sequence of (1) in between any two amino acid residues within the following sequences: amino acid residues 148–158 of Barley Translation Inhibitor (SEQ ID NO:26), amino acid residues 152–162 of Ricin A-chain RIP (SEQ ID NO:27), amino acid residues 138–148 of Abrin-A A-chain (SEQ ID NO:71), amino acid residues 153–163 of Saporin (SEQ ID NO:72), amino acid residues 145–155 of SLT 1 RIP (SEQ ID NO:73), antino acid residues 139–149 of Trichosanthin (SEQ ID NO:74), amino acid residues 138–148 of Luffin-A (SEQ ID NO:75), amino acid residues 145–155 of MAP (SEQ. ID NO:76), amino acid residues 152–162 of Rioinus communis agglutinin (SEQ ID NO:77), amino acid residues 138–148 of Momordin (SEQ ID NO:78), amino acid residues 151–161 of PAP-S (SEQ ID NO:79), amino acid residues 139–149 of Luffin-B (SEQ ID NO:80), and amino acid residues 174–184 of Dianthin 30 (SEQ ID NO:81).

5. A biologically functional expression vehicle containing the DNA isolate of claim 1.

6. A host cell transformed with a biologically functional expression vehicle of claim 5.

7. The transformed host cell of claim 6, wherein the host cell is a eukaryotic cell.

8. The host cell of claim 7, wherein the host cell is maize.

9. A method of making a protein incapable of substantially inactivating eukaryotic ribosomes, termed a proRIP, said method comprising the steps (a) providing a first DNA sequence encoding a RIP having at least one restriction site engineered therein, (b) cleaving the first DNA with a restriction enzyme to form first DNA subsequences, (c) providing a second DNA isolate encoding a polypeptide of nucleic acid coding sequence for amino acid residues 162–186 of SEQ ID:2 or a 70% homologous sequence that displays inhibition activity, and having ends ligatable with the cleaved ends of the first DNA subsequences, (d) ligating the first DNA subsequences and the second DNA to form a third DNA sequence capable of expressing a proRIP, and (e) expressing the proRIP.

* * * * *

UNITED STATES PATENT AND TRADEMARK OFFICE
CERTIFICATE OF CORRECTION

PATENT NO. : 5,646,026
DATED : Jul. 8, 1997
INVENTOR(S) : Terence A. Walsh; Timothy D. Hey, both of Zionsville, Ind.;
Alice E. R. Morgan, Midland, Mich.

It is certified that error appears in the above-indentified patent and that said Letters Patent is hereby corrected as shown below:

Col. 129, line 58, ";" should read -- : -- ; line 62, "eukaryohic" should read -- eukaryotic -- ; line 65, ";" should read -- : -- .
Col. 131, line 3, "commahis" should read --communis-- ; line4, "buffin-B" should read -- Luffin-B -- ; line 21, "Rioinus" should read -- Ricinus -- .
Col. 132, line 18, -- RIP -- should be inserted after displays.

Signed and Sealed this

Second Day of December,1997

Attest:

BRUCE LEHMAN

Attesting Officer

Commissioner of Patents and Trademarks